(12) United States Patent
Carrese et al.

(10) Patent No.: US 11,970,692 B2
(45) Date of Patent: Apr. 30, 2024

(54) MAGNET ASSEMBLY TO PREVENT EXTRACTION PARTICLE CARRYOVER

(71) Applicant: BECTON, DICKINSON AND COMPANY, Franklin Lakes, NJ (US)

(72) Inventors: Edward Carrese, Glen Arm, MD (US); Alexandre Daviet, Mungret (IE); Rohini Rao, Baltimore, MD (US); Alyssa Shedlosky, Reisterstown, MD (US); Ben Hopwood, Salt Lake City, UT (US); Dwight Livingston, Fallston, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 525 days.

(21) Appl. No.: 17/117,471

(22) Filed: Dec. 10, 2020

(65) Prior Publication Data

US 2021/0180043 A1   Jun. 17, 2021

Related U.S. Application Data

(60) Provisional application No. 62/948,003, filed on Dec. 13, 2019.

(51) Int. Cl.
  *C12N 15/10* (2006.01)
  *B03C 1/28* (2006.01)
  *C12Q 1/6806* (2018.01)
(52) U.S. Cl.
  CPC .......... *C12N 15/1013* (2013.01); *B03C 1/288* (2013.01); *C12Q 1/6806* (2013.01); *B03C 2201/18* (2013.01); *B03C 2201/26* (2013.01)

(58) Field of Classification Search
  CPC ............................. C12N 15/1013; B03C 1/12
  See application file for complete search history.

(56) References Cited

U.S. PATENT DOCUMENTS

| 6,672,458 | B2 | 1/2004 | Hansen et al. |
| 7,329,488 | B2 | 2/2008 | Roh et al. |
| 9,694,368 | B2 | 7/2017 | Tajima |
| 9,765,383 | B2 | 9/2017 | Park et al. |
| 2002/0014443 | A1* | 2/2002 | Hansen ............... C12N 15/1013 536/25.4 |
| 2007/0092403 | A1* | 4/2007 | Wirbisky ................. G01N 1/34 422/65 |

(Continued)

OTHER PUBLICATIONS

International Search Report and Written Opinion for International Application No. PCT/US2020/064190 dated Mar. 10, 2021 in 24 pages.

*Primary Examiner* — Samuel C Woolwine
(74) *Attorney, Agent, or Firm* — Knobbe, Martens, Olson & Bear LLP

(57) ABSTRACT

Disclosed herein are embodiments of a fixed magnet assembly that can be implemented into automated platforms for performing polynucleotide extraction from biological samples and preparing the polynucleotides into an amplification-ready form. The fixed magnet assembly can be used to provide magnetic energy to a container containing magnetic particles and a reaction mixture of polynucleotides, in order to bring about a separation of the magnetic particles from the reaction mixture. This can prevent or reduce magnetic particle carryover in the prepared amplification-ready sample, thereby improving amplification results.

17 Claims, 47 Drawing Sheets

(56) References Cited

U.S. PATENT DOCUMENTS

| | | | |
|---|---|---|---|
| 2008/0159915 A1* | 7/2008 | Yu | G01N 35/0098 |
| | | | 345/173 |
| 2009/0176308 A1* | 7/2009 | Griebel | G01N 35/0098 |
| | | | 422/400 |
| 2010/0288395 A1* | 11/2010 | Hagen | B01L 3/561 |
| | | | 141/234 |
| 2011/0031168 A1 | 2/2011 | Ellis et al. | |
| 2011/0198293 A1 | 8/2011 | Ellis et al. | |
| 2012/0269702 A1 | 10/2012 | Safar et al. | |
| 2013/0209995 A1* | 8/2013 | Andrulat | C12N 15/1013 |
| | | | 435/6.1 |
| 2017/0199107 A1* | 7/2017 | Guckenberger | B01L 3/502 |
| 2017/0283888 A1* | 10/2017 | Fiss | C12Y 207/07049 |
| 2018/0017184 A1 | 1/2018 | Handique | |
| 2019/0056415 A1* | 2/2019 | Lai | C12N 15/1013 |
| 2019/0239975 A1 | 8/2019 | Bernet et al. | |
| 2022/0090166 A1* | 3/2022 | Huang | C12N 15/1013 |

\* cited by examiner

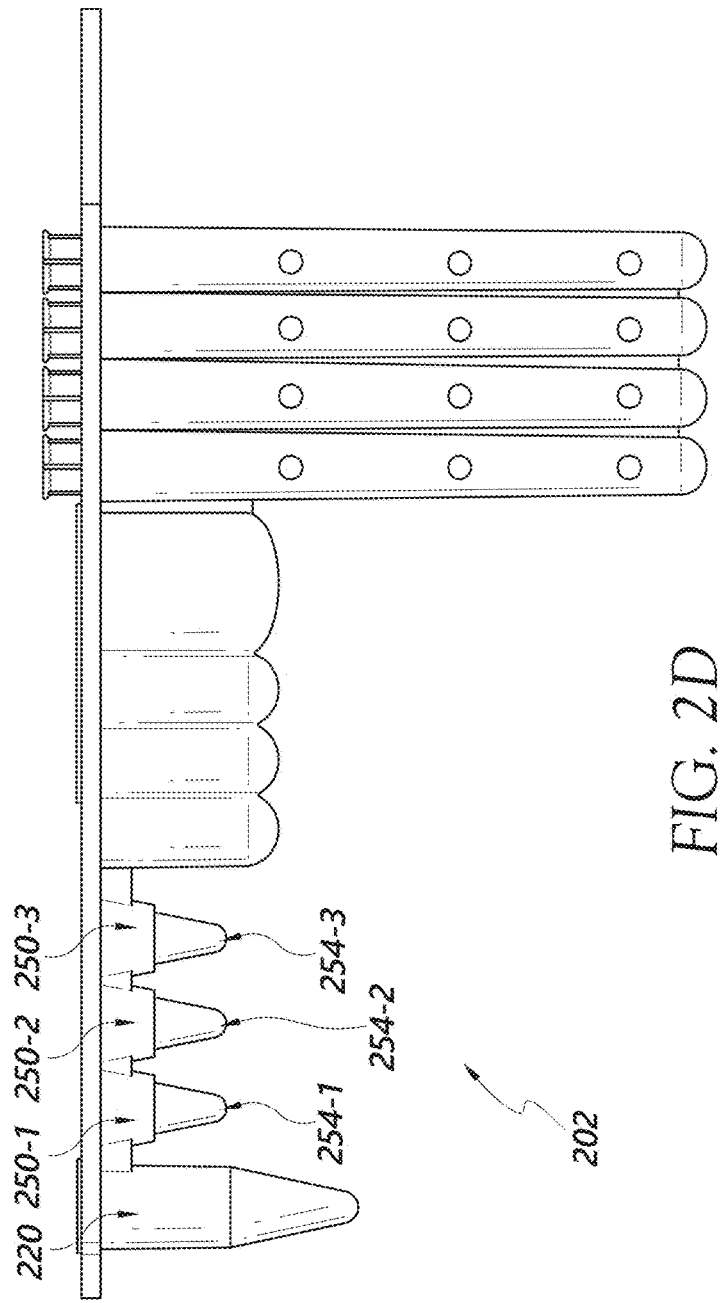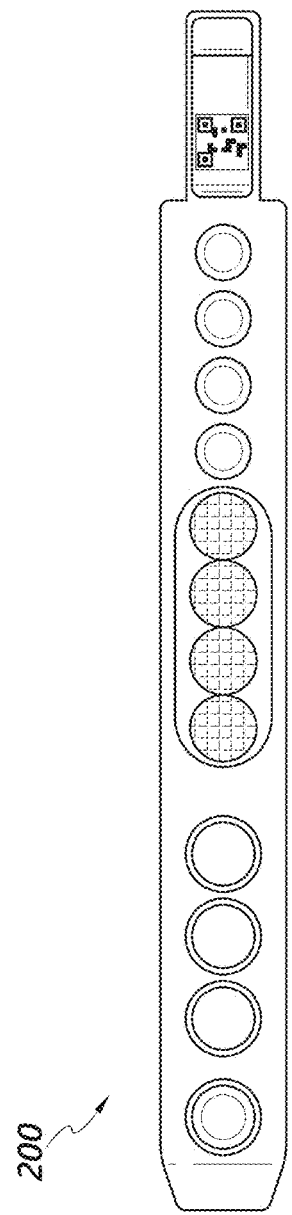

MAGNET ASSEMBLY TO PREVENT EXTRACTION PARTICLE CARRYOVER

CROSS-REFERENCE TO RELATED APPLICATIONS

This application claims the benefit of U.S. Provisional Application No. 62/948,003, filed Dec. 13, 2019, which is hereby incorporated by reference in its entirety.

TECHNICAL FIELD

The present disclosure generally relates to automated platforms for performing polynucleotide extraction from biological samples and preparing the polynucleotides into a PCR-ready form. More specifically, the present disclosure relates to a fixed magnet assembly usable with such automated platforms in order to provide magnetic energy to a container containing magnetic particles and a reaction mixture of polynucleotides, in order to bring about a separation of the magnetic particles from the reaction mixture.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using an amplification method, including but not limited to polymerase chain reaction (PCR), TMA, SDA, NASBA, LCR, and Rolling-Cycle Amplification, to amplify a vector of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because most samples must be heated at one or more stages, and in part because target polynucleotides are typically captured by some kind of retention member which must then be effectively isolated from the surrounding milieu. Thus, even where various liquid transfer operations can be optimized, and even automated, there is still a need for controlled application of heat, and efficient capture of extracted polynucleotides in situ.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The systems, methods, and devices described herein each have several aspects, no single one of which is solely responsible for its desirable attributes. Without limiting the scope of this disclosure, several non-limiting features will now be discussed briefly.

Disclosed herein are embodiments of a fixed magnet assembly that can be implemented into automated platforms for performing polynucleotide extraction from biological samples and preparing the polynucleotides into a PCR-ready form. The fixed magnet assembly can be used to provide magnetic energy to a container containing magnetic particles and a reaction mixture of polynucleotides, in order to bring about a separation of the magnetic particles from the reaction mixture. This can prevent or reduce magnetic particle carryover in the prepared PCR-ready sample, thereby improving PCR results.

In various embodiments, a system for analyzing nucleic acids is contemplated, and the system may include a receiving bay configured to receive a plurality of lysing tubes aligned along a lysing axis and a plurality of mixing tubes aligned along a mixing axis generally parallel to the lysing axis. The receiving bay may include: one or more first magnets aligned along a first magnet axis (which is generally parallel to the lysing and the mixing axes) and one or more second magnets aligned along a second magnet axis (which is generally parallel to the first magnet axis). The one or more first magnets may be configured to move between a position below the plurality of lysing tubes to a position adjacent to the plurality of lysing tubes when the plurality of lysing tubes are received in the receiving bay. The one or more first magnets may be configured to apply a first magnetic force to contents of the plurality of lysing tubes when the plurality of lysing tubes are received in the receiving bay and the one or more first magnets are positioned adjacent to the plurality of lysing tubes. The one or more second magnets may be configured to remain stationary when the plurality of mixing tubes are received in the receiving bay, the one or more second magnets configured to apply a second magnetic force to contents of the plurality of mixing tubes when the plurality of mixing tubes are received in the receiving bay.

In some embodiments, the one or more second magnets are included in a fixed magnet assembly, which may include a mounting plate, a support plate having a height relative to the mounting plate, and a first plurality of fasteners mechanically coupling the support plate to the mounting plate. The first plurality of fasteners may enable the height of the support plate relative to the mounting plate to be user-adjustable. In some cases, each of the first plurality of fasteners may include a jack screw.

In some embodiments, when the plurality of lysing tubes and the plurality of mixing tubes are received in the receiving bay, the first magnetic force is applied to contents of each of the plurality of lysing tubes along a direction that is generally perpendicular to the lysing axis, and the second magnetic force is applied to contents of each of the plurality of mixing tubes along a direction that is generally parallel to the mixing axis. In some embodiments, when the plurality of lysing tubes and the plurality of mixing tubes are received in the receiving bay, the first magnetic force is applied to contents of each of the plurality of lysing tubes along a direction that is generally perpendicular to the lysing axis, and the second magnetic force is applied to contents of each of the plurality of mixing tubes along a direction that is generally perpendicular to the mixing axis. In some embodiments, the receiving bay is further configured to receive a processing device comprising the plurality of lysing tubes and the plurality of mixing tubes. In some embodiments, the first magnet axis is spatially separate from the second magnet axis a distance such that the one or more first magnets do not exert the first magnetic force on contents of the plurality of mixing tubes when the plurality of mixing tubes are received in the receiving bay, and the one or more second magnets do not exert the second magnetic force on contents of the plurality of lysing tubes when the plurality of lysing tubes are received in the receiving bay.

In some embodiments, the system may further include a plurality of second magnets enclosed within a plurality of housings aligned along the second magnet axis, with each housing of the plurality of housings enclosing two of the plurality of second magnets. In some embodiments, when the plurality of mixing tubes are received in the receiving bay, a first of the two magnets in each housing is configured to apply the second magnetic force to contents of a first mixing tube at a first position of the first mixing tube, and wherein a second of the two magnets in each housing is configured to apply the second magnetic force to contents of a second mixing tube that is adjacent to the first mixing tube, the second of the two magnets configured to apply the second magnetic force at a second position of the second mixing tube that is about 180 degrees or less than 180 degrees from a first position of the second mixing tube. In some embodiments, when the plurality of mixing tubes is received in the receiving bay, the ratio of mixing tubes to housings is two-to-one.

In some embodiments, the system may further include a plurality of first magnets aligned along the first magnet axis, and when the plurality of lysing tubes is received in the receiving bay, the ratio of lysing tubes to first magnets is one-to-one. In some embodiments, each housing may include two faces that are each angled a different angle relative to the second magnet axis, and each of the two second magnets (enclosed in the housing) is positioned adjacent to an interior wall of one angled face of the housing.

In some embodiments, the system may further include a unitary structure that includes the plurality of housings. In some embodiments, the plurality of housings are separated by a plurality of connectors.

In some embodiments, the system may include one second magnet formed of a magnetic material, with the second magnet including a plurality of magnet structures aligned along the second magnet axis. Each magnet structure may include two angled magnet faces that are each angled a different angle relative to the second magnet axis. In some embodiments, when the plurality of mixing tubes are received in the receiving bay, a first angled magnet face of each magnet structure is configured to apply the second magnetic force to contents of a first mixing tube at a first position of the first mixing tube, and a second angled magnet face of each magnet structure is configured to apply the second magnetic force to contents of a second mixing tube that is adjacent to the first mixing tube. The second angled magnet face may be configured to apply the second magnetic force at a second position of the second mixing tube that is about 180 degrees or less than 180 degrees from a first position of the second mixing tube.

In some embodiments, when the plurality of mixing tubes is received in the receiving bay, the ratio of mixing tubes to magnet structures is two-to-one. In some embodiments, the system may further include a plurality of first magnets aligned along the first magnet axis, and, when the plurality of lysing tubes is received in receiving bay, the ratio of lysing tubes to first magnets is one-to-one. In some embodiments, the receiving bay may further include a support plate positioned between the one or more second magnets and a cover of the receiving bay. In some embodiments, the support plate includes a plurality of recesses each configured to receive a bottom portion of one mixing tube when the plurality of mixing tubes are received in the receiving bay.

In some embodiments, the system may further include a plurality of second magnets enclosed within a plurality of housings aligned along the second magnet axis, and the plurality of housings are movable relative to the support plate when the plurality of mixing tubes are not received in the receiving bay. In some embodiments, the system may further include the plurality of lysing tubes and the plurality of mixing tubes received in the receiving bay.

In various embodiments, a system for analyzing nucleic acids is contemplated, and the system may include: a receiving bay configured to receive a device having a lysing tube and a mixing tube aligned along each of a plurality of parallel processing axes. The receiving bay may include one or more first magnets aligned along a first magnet axis generally perpendicular to the plurality of processing axes, and may also include one or more second magnets aligned along a second magnet axis generally perpendicular to the first magnet axis. The one or more first magnets may be configured to move between a position below the plurality of lysing tubes to a position adjacent to the plurality of lysing tubes when the device is received in the receiving bay. The one or more first magnets may be configured to apply a first magnetic force to contents of the plurality of lysing tubes when the device is received in the receiving bay and the one or more first magnets are positioned adjacent to the plurality of lysing tubes. The one or more second magnets may be configured to remain stationary when the plurality of mixing tubes are received in the receiving bay. The one or more second magnets may be configured to apply a second magnetic force to contents of the plurality of mixing tubes when the device is received in the receiving bay.

In some embodiments, when the device is received in the receiving bay, the first magnetic force is applied along the respective processing axis of each of the plurality of lysing tubes, and the second magnetic force is applied at a point offset from the respective processing axis of each of the plurality of mixing tubes. In some embodiments, when the device is received in the receiving bay, the first magnetic force is applied along the respective processing axis of each of the plurality of lysing tubes, and the second magnetic force is applied along the respective processing axis of each of the plurality of mixing tubes.

In some embodiments, the first magnet axis is spatially separate from the second magnet axis a distance such that the one or more first magnets do not exert the first magnetic force on contents of the plurality of mixing tubes when the device is received in the receiving bay, and the one or more second magnets do not exert the second magnetic force on contents of the plurality of lysing tubes when the device is received in the receiving bay.

In some embodiments, the system may further include a plurality of second magnets enclosed within a plurality of housings aligned along the second magnet axis, and each housing of the plurality of housings encloses two of the plurality of second magnets. In some embodiments, when the device is received in the receiving bay, a first of two magnets in each housing is configured to apply the second magnetic force to contents of a first mixing tube at a first position of the first mixing tube. A second of the two magnets in each housing may be configured to apply the second magnetic force to contents of a second mixing tube that is adjacent to the first mixing tube, and the second of the two magnets may be also configured to apply the second magnetic force at a second position of the second mixing tube that is about 180 degrees or less than 180 degrees from a first position of the second mixing tube.

In some embodiments, when the device is received in the receiving bay, the ratio of mixing tubes to housings is two-to-one. In some embodiments, the system may further include a plurality of first magnets aligned along the first magnet axis, and, when the device is received in the receiving bay, the ratio of lysing tubes to first magnets is one-to-one. In some embodiments, each housing includes two faces that are each angled relative to an adjacent processing axis, and each of the two second magnets is positioned adjacent to an interior wall of one angled face.

In some embodiments, the system may further include a unitary structure that includes the plurality of housings. In some embodiments, the receiving bay further includes a support plate positioned between the one or more second magnets and a cover of the receiving bay. In some embodiments, the support plate includes a plurality of recesses each configured to receive a bottom portion of one mixing tube when the device is received in the receiving bay. In some embodiments, the system may further include a plurality of second magnets enclosed within a plurality of housings aligned along the second magnet axis, and wherein the plurality of housings are movable relative to the support plate before the device is received in the receiving bay. In some embodiments, the system may further include the device received in the receiving bay.

Additional embodiments of the disclosure are described below in reference to the appended claims, which may serve as an additional summary of the disclosure.

BRIEF DESCRIPTION OF THE DRAWINGS

FIG. 2D illustrates a side profile view of an exemplary reagent holder, in accordance with embodiments disclosed herein.

FIG. 2E illustrates a top-down view of an exemplary reagent holder, in accordance with embodiments disclosed herein.

DETAILED DESCRIPTION

Automated platforms (which can be alternatively referred to as an automated diagnostic or preparatory apparatus) exist for processing biological samples for diagnostic or preparatory purposes. For instance, these automated platforms can be used for performing polynucleotide extraction from biological samples and preparing polynucleotides into a PCR-ready form.

Some embodiments of these automated platforms perform polynucleotide extraction and preparation by mixing the cells in a biological sample with a lysing reagent in a process tube and heating the process tube, which lyses the cells and releases the polynucleotides contained in the cells. In order to isolate the polynucleotides from the rest of the mixture, magnetic extraction particles (e.g., surface-modified magnetic beads) configured to bind to those polynucleotides can be added to the mixture. Magnetic extraction particles are also referred to herein as magnetic substrates or magnetic binding particles. The magnetic extraction particles can include, for example, beads modified with PAMAM, dendritic polyamines, poly(allylamine) (PAA), polypropylenimine tetramine dendrimer (DABAM), or any other suitable material. Once the polynucleotides bind to the magnetic extraction particles, magnets can be used to apply a magnetic force for holding the magnetic extraction particles in place and separating them from the rest of the mixture. Some embodiments of these automated platforms may have a magnetic separator that can be moved up and down relative to the process tube, in order to raise the magnetic extraction particles out of the rest of the mixture and remove the rest of the mixture.

Once the magnetic extraction particles have been isolated in the process tube, chemical eluents can be added to the process tube in order to detach the polynucleotides from the magnetic extraction particles. Some embodiments of the automated platforms may use the magnetic separator again to capture and hold the magnetic extraction particles in place while the polynucleotides are extracted from the process tube and transferred to a separate mixing tube. The polynucleotides can then be added to a mixture of primers and probes used in PCR amplification, which can then be loaded into a device (e.g., a microfluidics cartridge) for PCR amplification.

Figure 1A:
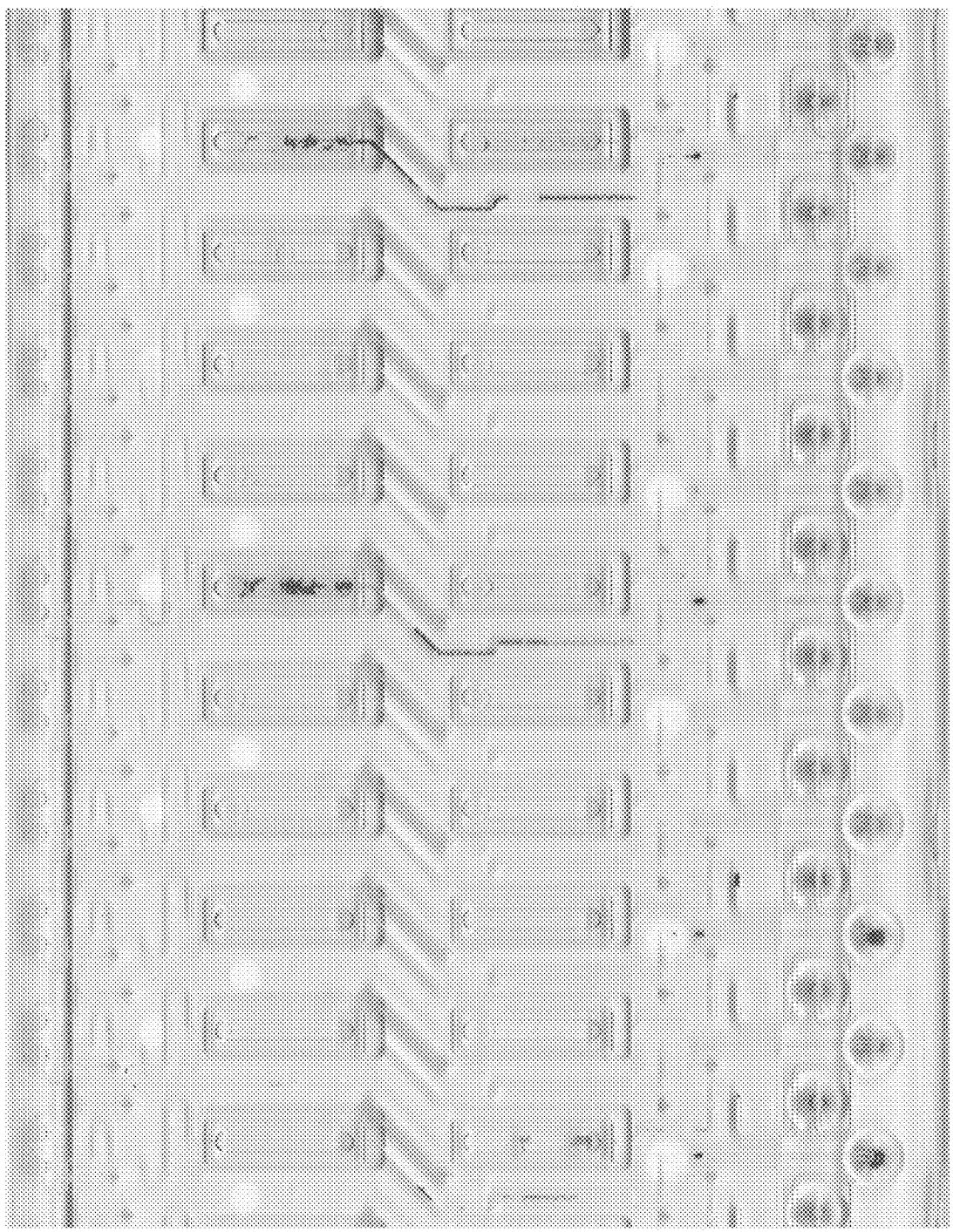
FIG. 1A illustrates an image of a device for PCR amplification (e.g., a microfluidics cartridge) that is mechanically clogged by carried over magnetic extraction particles, in accordance with embodiments disclosed herein.

However, there can be some chemical components present, either within a sample's cellular matrix or other substances present during sample collection, which can prevent sufficient magnetic capture of the magnetic extraction particles to separate them from the rest of the contents in the process tube. Some examples of substances present during sample collection may include medical lubricants, antifungal creams, antibacterial creams, contraceptive gels and foams, vaginal moisturizing creams, and so forth. Any of the chemical components present may interact with the modified surface of the magnetic extraction particles, the cellular matrix, captured polynucleotides, or a combination of any of these, and interrupt magnetic capture of the magnetic extraction particles. As a result, when the polynucleotides are extracted from the process tube and transferred to the mixing tube, there may be magnetic extraction particles that carry over to the mixing tube and, from there, end up in the device used for PCR amplification (e.g., microfluidics cartridge). This magnetic extraction particle "carryover" can cause either mechanical or chemical failures of PCR amplification that trigger assay failures, such as non-reportables (NRs). Mechanically, the carryover particles can clog the loading ports or microfluidics in the PCR amplification device (e.g., the microfluidics cartridge). An example of this is shown in FIG. 1A, which illustrates an image of a device for PCR amplification (e.g., a microfluidic cartridge) that is mechanically clogged by carried-over magnetic extraction particles. Chemically, the problematic components of the cellular matrix or other interfering substances, which bind to the carried-over magnetic extraction particles, can interfere with or inhibit the PCR reaction and subsequent detection of the amplification products.

In order to reduce and prevent this undesired magnetic extraction particle carryover, various embodiments of a fixed magnet assembly are contemplated and disclosed herein that can be implemented with these automated platforms. In some embodiments, the fixed magnet assembly may include a set of angled magnets within a housing positioned in close proximity to the mixing tubes. In some of such embodiments, the individual magnets may be 0.25×0.25×0.0625" NdFeB, Grade N52 square magnets, that have a pull force of 1.77 lbs and field strength of 3032 Gauss. However, for other embodiments, suitable magnets may include magnets of various different materials, sizes, and/or strengths, as long as the selected magnet configuration combined with the positioning of the magnets by the mixing tubes enable the magnets to capture some or all of the magnetic extraction particles that have been carried over to the mixing tubes. The magnets may be positioned close enough to the mixing tubes to generate a magnetic field of sufficient strength to retain or "trap" carried-over magnetic extraction particles in the mixing tube, and in particular against an interior wall of the mixing tube. Thus, the fixed magnet assembly of the disclosed technology may provide a secondary set of magnets (in addition to the first set of magnets in the magnetic separator), which can be positioned in fixed locations near mixing tubes to provide a secondary magnetic capture for any undesired magnetic extraction particles that are carried over to the mixing tube (e.g., extraction particles not captured during earlier steps in the workflow), in order to prevent those magnetic extraction particles from being carried over into the PCR amplification device.

Embodiments of the disclosed technology can be advantageously implemented in any apparatus that receives a holder for processing and manipulating magnet substrates within a container of the holder. Implementations of the fixed magnet assembly according to the disclosed technology can be placed in a very small, predefined volume or envelope that exists between a cover of a receiving bay and a processing device received in the bay. As a result, existing diagnostic or preparatory apparatuses with a particular receiving bay configured to receive a particular processing device can be retrofitted with the fixed magnet assembly without having to re-design the processing device (such as a reagent holder or processing plate) or components that snap-in to the device (such as reagent tubes or containers). Despite being retrofitted into apparatuses that have been implemented across numerous sites and that have some variation in components, magnets of the fixed magnet assembly still effectively and consistently apply a magnetic force to the contents of the processing devices received by these field-deployed systems. Further significant advantages of the disclosed technology is that it can be implemented in field-deployed systems very quickly, with minimal down time to the customer or the laboratory employing the apparatus.

Installation of fixed magnet assemblies according to the disclosed technology can be adjusted for site-specific characteristics and constraints. As will be described in detail below, a fixed magnet assembly can be installed with a shim between the assembly and the cover of the receiving bay, where the height of the shim is selected based on site-specific considerations. This can be particularly advantageous when a fixed magnet assembly is retrofitted into existing preparatory and diagnostic apparatuses in the field, in view of very slight differences in the dimensions and tight tolerances associated with receiving bays and processing devices implemented in the apparatuses.

As another example of the advantageous adjustability and versatility of the disclosed technology, some embodiments of the fixed magnet assembly include a spring-mounted support plate that is movable in a z-direction relative to a mounting plate that is fixed to the cover of the receiving bay. The mounting plate can be fixed using any suitable mechanism, including but not limited to screws or adhesive tape (including double-sided tape). The support plate can move upward or downward in the z-direction in the receiving bay before and during insertion of a processing device in the receiving bay. This feature may allow for tubes or containers of a processing device to be accurately and consistently positioned relative to magnets in the fixed magnet assembly, without requiring that exact magnet positioning (e.g., via designing, building, and positioning the fixed magnet assembly with very tight tolerances) be accurately and consistently reproduced across each of a plurality of apparatuses in which a fixed magnet assembly is installed.

As yet another example of the advantageous adjustability and versatility of the disclosed technology, some embodiments of the fixed magnet assembly include a support plate that is mechanically coupled to a mounting plate using a plurality of adjustable fasteners, which allows the support plate to be movable in the z-direction relative to the mounting plate by adjusting the fasteners. The support plate can be mechanically coupled to the mounting plate using any suitable fastener that can be adjusted to modify the distance between the support plate and the mounting plate. For instance, the support plate can be mechanically coupled to the mounting plate with a plurality of jack screws, which can be threaded clockwise or counter-clockwise in order to increase or decrease the distance between the support plate and the mounting plate (e.g., raise or lower the height of the support plate in the z-direction), respectively. The mounting plate may be fixed to the cover of the receiving bay using any suitable mechanism, including but not limited to screws or adhesive tape (including double-sided tape). This feature may allow for an installer of the fixed magnet assembly (e.g., including but not limited to a user of the system) to manually adjust the height of the support plate based on the particular apparatus the fixed magnet assembly is installed in, such that tubes or containers of a processing device are accurately and consistently positioned relative to magnets in the fixed magnet assembly, without requiring the fixed magnet assembly to be pre-configured with that exact magnet positioning be (e.g., via designing, building, and positioning the fixed magnet assembly with very tight tolerances) and thereby enabling the fixed magnet assembly to be used with various apparatuses that may have inconsistent dimensions.

Embodiments of fixed magnet assemblies according to the disclosed technology can include a plurality of magnet housings or structures. As will be described in detail below, the magnet housings and structures can include faces that are advantageously oriented to align very closely with (for example, within 1-2 mm of) a tube or container containing magnetic structures while also avoiding interference with the tube (or features surrounding the tube) when the tube is inserted into the receiving bay. The faces can be angled relative to a processing axis on which the tube lies, while still maintaining very close proximity to the tube. In the case of magnet housings, magnets that are coupled to inner walls of the faces can be advantageously oriented. In the case of magnet structures formed of a magnetic material, angled faces can be advantageously oriented. The shape and dimensions of the magnet housings/structures and the shape and dimensions of connecting structures that connect the magnet housings/structures can be advantageously tailored, such that they do not interfere with a skirt or flange on the underside of a processing device that receives a snap-in reagent tube or container. The magnet housings/structures can thus avoid undesirable physical interference with a tube containing magnetic substrates as well as nearby tubes that do not contain magnetic substrates, while still positioning a magnet in very close physical proximity to the tube containing magnetic substrates.

Embodiments of fixed magnet assemblies according to the disclosed technology can include magnet housings/structures that are configured to simultaneously apply a magnetic force to two different tubes or containers that are arranged on parallel processing axes. For example, in the case of a magnet housing enclosing two magnets, one magnet housed in the magnet housing can apply a magnetic force to one side of a first container of a processing device, and another magnet housed in the magnet housing can apply a magnetic force to an opposing side of a second container of the processing device, where the first and second containers are positioned on parallel processing axes. In other words, the magnets in a magnet housing may apply magnetic force to opposite sides of the containers of adjacent processing axes. In a non-limiting example, in which reagents holders are received in a rack that is inserted into a receiving bay, magnets within a single magnet housing can apply magnetic force to opposite sides of snap-in containers of adjacent reagent holders. Although magnetic force is applied to different sides of snap-in containers depending on which magnet is in close proximity to the snap-in containers, the problem of magnetic extraction particle carry-over is effectively and consistently addressed for each of the reagent holders. Advantageously, this implementation can avoid having to place the magnets in a very tight space (e.g., between the snap-in container that includes magnetic particles and another snap-in container aligned along the same processing axis). Instead, the magnets of the disclosed technology can be Advantageously arranged at an oblique angle relative to the processing axis of each reagent holder, rather than being arranged on the processing axis.

As described above, the fixed magnet assembly may be designed to be quickly and efficiently implemented, even into existing automated diagnostic or preparatory apparatuses without any hardware modifications to the apparatus. Different embodiments of the fixed magnet assembly of the disclosed technology may be designed, configured, and tailored for use with a specific embodiment of an automated diagnostic or preparatory apparatus. Some specific examples of the various embodiments of the fixed magnet assembly are shown and discussed herein.

For instance, FIGS. 1B, 2A-2E, 3A-3C, 4A-4B, 5A-5B provide context for a first embodiment of an automated diagnostic or preparatory apparatus. FIGS. 6A-6C provide a conceptual overview of how a fixed magnet assembly can be configured, positioned, and implemented with respect to this first embodiment of the automated diagnostic or preparatory apparatus, in order to reduce or prevent magnetic extraction particle carryover. FIGS. 7A-7B, 8A-8B, 9, 10A-10B, and 16A-16F illustrate various different embodiments of a fixed magnet assembly that demonstrate additional features and concepts outlined in connection with FIGS. 6A-6C. The example fixed magnet assemblies described with reference to FIGS. 6A-6C can be implemented in the first embodiment of the automated diagnostic or preparatory apparatus in order to prevent magnetic extraction particle carryover. It will be understood that these are non-liming examples and other suitable configurations and implementations are also consistent with the disclosed technology.

Additionally, FIGS. 11, 12A-12B, and 13A-13B provide context for a second embodiment of an automated diagnostic or preparatory apparatus in which a fixed magnet assembly of the disclosed technology can be implemented. FIGS. 14A-14C provide a conceptual overview of how a fixed magnet assembly can be configured, positioned, and implemented with respect to this second embodiment of the automated diagnostic or preparatory apparatus, in order to prevent magnetic extraction particle carryover. FIGS. 15A-15D illustrate an embodiment of a fixed magnet assembly that demonstrate additional features and concepts outlined in connection with FIGS. 14A-14C. The example fixed magnet assemblies described with reference to FIGS. 15A-15D can be implemented with the second embodiment of the automated diagnostic or preparatory apparatus in order to prevent magnetic extraction particle carryover. It will be understood that these are non-liming examples and other suitable configurations and implementations are also consistent with the disclosed technology.

Figure 1B:
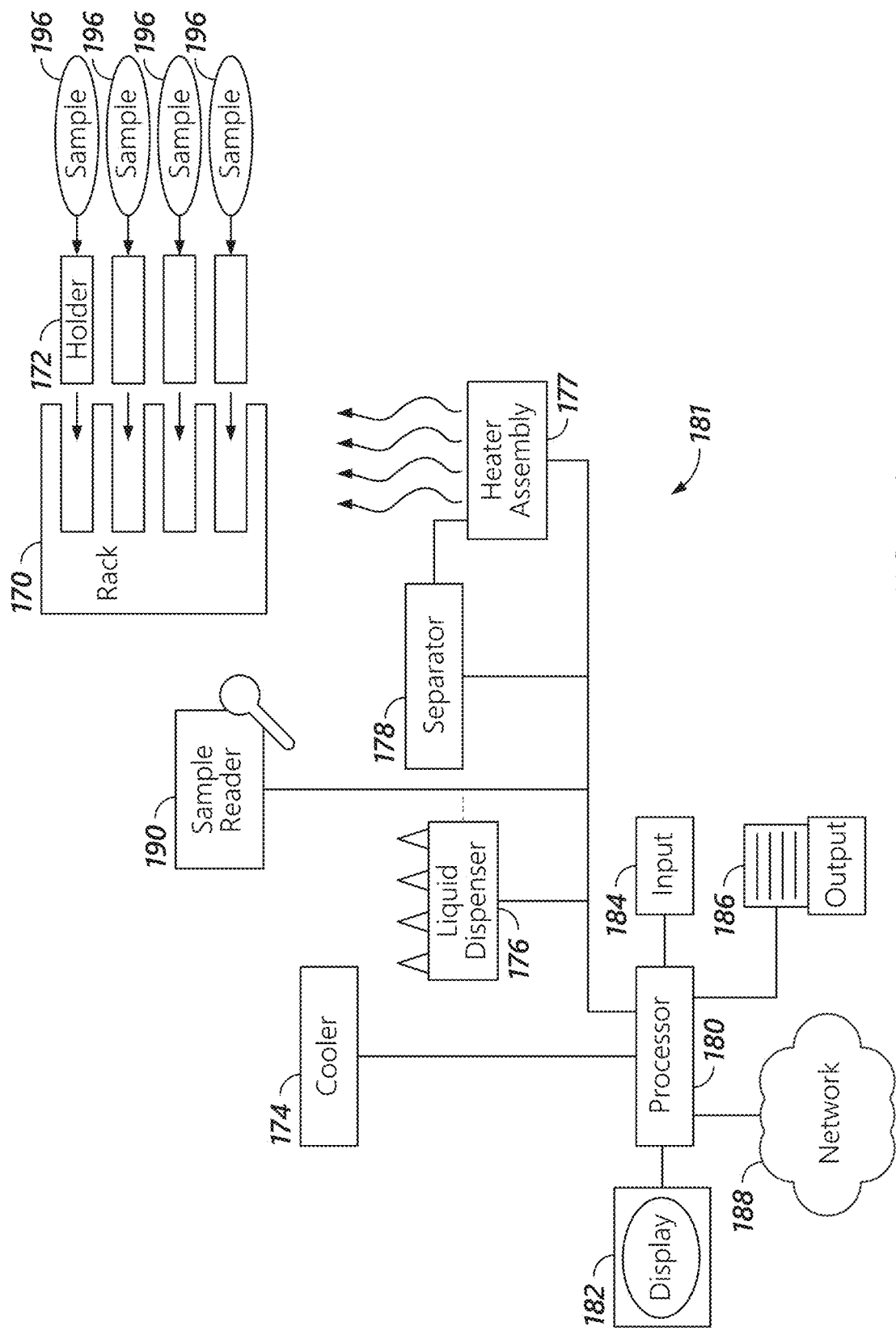
FIG. 1B illustrates a schematic overview of an automated diagnostic or preparatory apparatus for carrying out automated sample preparation on multiple samples in parallel, in accordance with embodiments disclosed herein.

Example Automated Apparatus, Reagent Holder, and Rack of the Disclosed Technology FIG. 1B illustrates a schematic overview of an apparatus 181 for carrying out automated sample preparation on multiple samples in parallel, according to steps exemplified elsewhere herein. The geometric arrangement of the components of system 181 is exemplary and not intended to be limiting. The apparatus may additionally include (not shown in FIG. 1B) a device, in a receiving bay, and configured to carry out a diagnostic test on the sample, such as by detecting presence of an amplified polynucleotide in the cartridge. The device can include, for example, a microfluidic cartridge, configured to receive polynucleotides that have placed into a PCR-ready form. Such additional features are also described in U.S. patent application Ser. No. 12/173, 023, filed on Jul. 14, 2008 (and entitled "Integrated Apparatus for Performing Nucleic Acid Extraction and Diagnostic Testing on Multiple Biological Samples", in the name of Williams, et al.). Unless specifically made clear to the contrary, where the term PCR is used herein, any variant of PCR including but not limited to real-time and quantitative, and any other form of polynucleotide amplification is intended to be encompassed.

A processor 180, such as a microprocessor, is configured to control functions of various components of the system as shown, and is thereby in communication with each such component requiring control. It is to be understood that many such control functions can optionally be carried out manually, and not under control of the processor. Furthermore, the order in which the various functions are described, in the following, is not limiting upon the order in which the processor executes instructions when the apparatus is operating. Thus, processor 180 can be configured to receive data about a sample to be analyzed, e.g., from a sample reader 190, which may be a barcode reader, an optical character reader, or an RFID scanner (radio frequency tag reader).

Processor 180 can be configured to accept user instructions from an input device 184, where such instructions may include instructions to start analyzing the sample, and choices of operating conditions. Processor 180 can be also configured to communicate with a display 182, so that, for example, information about an analysis is transmitted to the display and thereby communicated to a user of the system. Such information includes but is not limited to: the current status of the apparatus; progress of PCR thermocycling; and a warning message in case of malfunction of either system or cartridge. Additionally, processor 180 may transmit one or more questions to be displayed on display 182 that prompt a user to provide input in response thereto. Thus, in certain embodiments, input 184 and display 182 are integrated with one another. Processor 180 can be optionally further configured to transmit results of an analysis to an output device 186 such as a printer, a visual display, a display that utilizes a holographic projection, or a speaker, or a combination thereof. Processor 180 can be still further optionally connected via a communication interface such as a network interface to a computer network 188.

Processor 180 can be further configured to control various aspects of sample preparation and diagnosis, as follows in overview. In FIG. 1B, the apparatus 181 is configured to operate in conjunction with a complementary rack 170. Apparatus 181 may be capable of receiving multiple racks, such as 1, 2, 3, 4, or 6 racks.

Embodiments of rack 170 are further described in U.S. patent application Ser. No. 12/173,023, filed on Jul. 14, 2008 (entitled "Integrated Apparatus for Performing Nucleic Acid Extraction and Diagnostic Testing on Multiple Biological Samples", in the name of Williams, et al.), and U.S. patent application Ser. No. 12/178,584, filed on Jul. 23, 2008 (entitled "Rack For Sample Tubes And Reagent Holders", in the name of Duffy, et al.), both of which are incorporated herein by reference in their entireties. A rack 170 is itself configured to receive a number of biological samples 196 in a form suitable for work-up and diagnostic analysis, and a number of holders 172—as further described herein, such as in connection with FIGS. 2A-2C, that are equipped with various reagents, pipette tips and receptacles. The rack is configured so that, during sample work-up, samples are processed in the respective holders, the processing including being subjected, individually, to heating and cooling via heater assembly 177.

The heating functions of the heater assembly 177 can be controlled by the processor 180. Heater assembly 177 operates in conjunction with a separator 178, such as a magnetic separator, that also can be controlled by processor 180 to move into and out of close proximity to one or more processing chambers associated with the holders 172, wherein particles such as magnetic particles are present. Assembly 177 and separator 178 are further described herein.

Liquid dispenser 176, which similarly can be controlled by processor 180, is configured to carry out various suck and dispense operations on respective sample, fluids and reagents in the holders 172, to achieve extraction of nucleic acid from the samples. Liquid dispenser 176 can carry out such operations on multiple holders simultaneously.

Sample reader 190 is configured to transmit identifying indicia about the sample, and in some instances the holder, to processor 180. In some embodiments a sample reader is attached to the liquid dispenser and can thereby read indicia about a sample above which the liquid dispenser is situated. In other embodiments the sample reader is not attached to the liquid dispenser and is independently movable, under control of the processor. Liquid dispenser 176 is also configured to take aliquots of fluid containing nucleic acid extracted from one or more samples and direct them to storage area 174, which may be a cooler. The storage area 174 contains, for example, a PCR tube corresponding to each sample. Additionally, or as an alternative, liquid dispenser 126 can be configured to take aliquots of fluid containing nucleic acid extracted from one or more samples and direct them to a device configured to receive and amplify the nucleic acid. The device can include, for example, a microfluidic cartridge received in a receiving bay of the apparatus 181 (not illustrated).

Embodiments of the apparatus shown in outline in FIG. 1B, as with other exemplary embodiments described herein, are advantageous because they do not require locations within the apparatus suitably configured for storage of reagents. Therefore, the apparatus in FIG. 1B is self-contained and operates in conjunction with holders 172, wherein the holders are pre-packaged with reagents, such as in locations within it dedicated to reagent storage.

The apparatus of FIG. 1B may be configured to carry out operation in a single location, such as a laboratory setting, or may be portable so that they can accompany, e.g., a physician, or other healthcare professional, who may visit patients at different locations. The apparatus is typically provided with a power-cord so that they can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 1B may further be configured, in other embodiments, for multiplexed sample analysis and/or analysis of multiple batches of samples, where, e.g., a single rack holds a single batch of samples. Each component shown in FIG. 1B may therefore be present as many times as there are batches of samples, though the various components may be configured in a common housing.

The apparatuses as described herein find application to analyzing any nucleic acid containing sample for any purpose, including but not limited to genetic testing, and clinical testing for various infectious diseases in humans.

The apparatus herein can be configured to run on a laboratory benchtop, or similar environment, and can test approximately 45 samples per hour when run continuously throughout a normal working day. Results from individual raw samples are typically available in less than 1 hour.

Figure 2A:
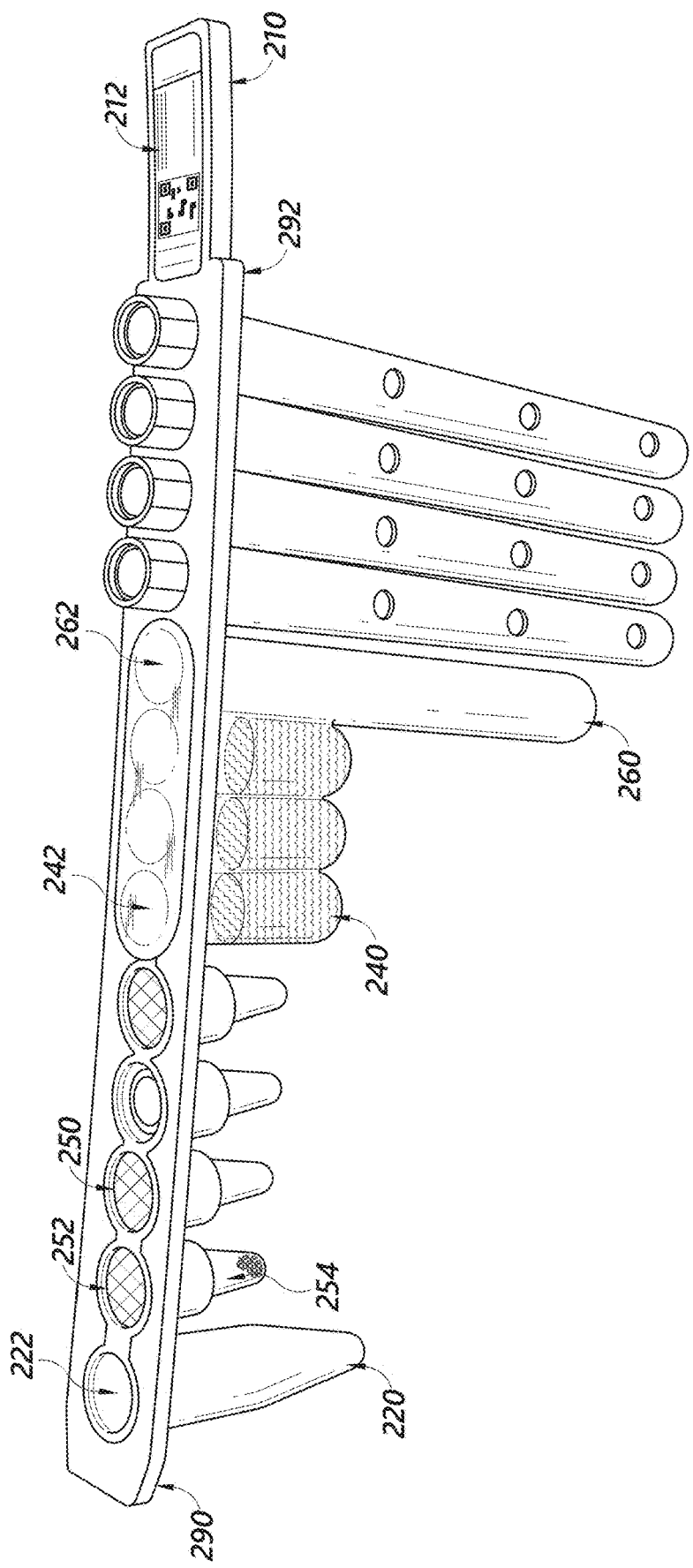
FIG. 2A illustrates an isometric view of an exemplary reagent holder, in accordance with embodiments disclosed herein.

FIG. 2A shows an isometric view of an exemplary holder (e.g., holder 172 shown in FIG. 1B) as described herein. The holders described herein are reagent holders for holding and transporting reagents for various purposes, including but not limited to sample preparation in a clinical context, and configured to be received by a rack as described herein. The reagent holders also typically provide a container in which various reagents can be mixed one with another and/or with a sample. The holders are also configured for use in an automated apparatus that can carry out sample preparation on samples in more than one holder simultaneously.

This exemplary holder, as well as others consistent with the written description herein though not shown as specific embodiments, are now described. Further details of reagent holders can be found in U.S. patent application Ser. No. 12/218,416, filed on Jul. 14, 2008 in the name of Wilson, et al., (entitled "Reagent Tube, Reagent Holder, and Kits Containing Same"), which is incorporated herein by reference.

The exemplary holder 200 of FIG. 2A includes a connecting member 210 having one or more characteristics as follows. Connecting member 210 serves to connect various components of the holder together. Connecting member 210 has an upper side 212 and, opposed to the upper side, an underside (not shown).

The reagent holder 200 will now be described in order to illustrate certain features of the disclosed technology, it will be understood that the disclosed technology can be implemented with any suitable holder that receives magnetic substrates, such as magnetic binding particles. The reagent holder 200 of FIG. 2A of this particular, non-limiting embodiment includes a process tube 220 having an aperture 222 located in the connecting member; two or more reagent tubes 240 disposed on the underside of the connecting member, each of the reagent tubes having an inlet aperture 242 located in the connecting member; and one or more receptacles 250, located in the connecting member, wherein the one or more receptacles 250 are each configured to receive a complementary container 254, such as a reagent tube, inserted from the upper side 212 of the connecting member. In the illustrated embodiment of FIGS. 2A-2C, the reagent holder 200 includes 4 receptacles 250, each configured to receive a snap-in container 254. In another non-limiting embodiment described below with reference to FIGS. 2D and 2E, the reagent holder includes 3 receptacles 250, each configured to receive a snap-in container 254. Implementations of the disclosed technology can be implemented in holders having any suitable number of receptacles, as well as in holders having containers 254 integrally formed with, rather than snapped into, the connecting member. The reagent holder 200 can optionally include at least one socket, located in the connecting member, the socket configured to accept a disposable pipette tip, and at least one pipette sheath. In this non-limiting embodiment, the reagent holder includes 4 sockets and 4 pipette sheaths. The lanes of the rack described herein are designed to have sufficient depth and width to accommodate the various reagent tubes, receptacles, process tube, and pipette sheath of a given reagent holder, and to position the process tube in communication with a heater/separator unit.

The containers 254 have been inserted into their corresponding receptacles 250. The one or more receptacles 250 are configured to accept reagent tubes that contain quantities of one or more reagents for carrying out extraction of nucleic acids from a sample that is associated with the holder. The reagents can be in solid form, such as in lyophilized form. The receptacles can be all of the same size and shape, or may be of different sizes and shapes from one another. Receptacles 250 are shown as having open bottoms, but are not limited to such topologies, and may be closed other than the inlet 252 in the upper side of connecting member 210. Preferably the receptacles 250 are configured to accept commonly used containers in the field of laboratory analysis, or containers suitably configured for use with the holder herein. For example, the containers 254 may be 0.3 ml tubes.

The embodiment of a reagent holder 200 is shown configured with a waste chamber 260, having an inlet aperture 262 in the upper side of the connecting member 210. Waste chamber 260 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed.

Process tube 220 can be configured as a snap-in tube, similar to containers 254, or it can be integrally formed in the connecting member 210. Process tube 220 can be used for various mixing and reacting processes that occur during sample preparation. For example, cell lysis can occur in process tube 220, as can extraction of nucleic acids, such as DNA or RNA of a patient, and DNA or RNA of a pathogen. Process tube 220 can be advantageously positioned in a location that minimizes, overall, pipette head moving operations involved with transferring liquids to process tube 220. Process tube 220 is also located in the holder in such a position that, when the holder is inserted in a rack as further described herein, the process tube is exposed and accessible to a heater and separator, as further described herein.

Some of the reagents contained in the holder are provided as liquids, and others may be provided as solids. In some embodiments, a different type of container or tube is used to store liquids from those that store the solids.

Reagent wells 240 are typically configured to hold liquid reagents, one per well. For example, in reagent holder embodiment 200, three reagent wells are shown, containing respectively wash buffer, release buffer, and neutralization buffer, each of which is used in a sample preparation protocol. Other numbers and configurations of reagent wells can be suitably implemented in embodiments of the disclosed technology.

The reagent holder 200 has a connecting member that is configured so that the at least one socket, the one or more receptacles, and the respective apertures of the process tube, and the two or more reagent tubes, are all arranged linearly with respect to one another (i.e., their midpoints lie on the same axis). As will be described in more detail below with reference to FIGS. 6A-6B, this axis can be a processing axis along which features of the holder are aligned. It will be understood that, in embodiments of the disclosed technology, features of the holder can be aligned in a substantially linear arrangement, such that the midpoints of the features do not lie precisely on a common processing axis. Further, the holders herein are not limited to particular configurations of receptacles, process tube, sockets, reagent tubes, and waste chamber if present. For example, a holder may be made shorter, if some apertures are staggered with respect to one another and occupy 'off-axis' positions. The various receptacles, etc., also do not need to occupy positions with respect to one another that are the same as those shown in FIG. 2A.

It would be understood that alternative configurations of the various parts of the holder 200 give rise only to variations of form and can be accommodated within other variations of the apparatus as described, including but not limited to alternative instruction sets for a liquid dispensing pipette head, heater assembly, and magnetic separator, as further described herein. Each such configuration of the reagent holder can be accommodated by a corresponding variation in form of the rack described herein that receives one or more such holders.

In some embodiments, the holder 200 includes a registration member such as a mechanical key. Typically such a key is part of the connecting member 210. A mechanical key ensures that the holder is accepted by a complementary member in, for example, a supporting rack as described herein (e.g., the rack 170 of FIG. 1B) or a receiving bay of an apparatus that controls pipetting operations on reagents in the holder. Thus, embodiment 200 has a mechanical key 292 that includes a pair of rectangular-shaped cut-outs on one end of the connecting member. This feature as shown additionally provides for a tab by which a user may gain a suitable purchase when inserting and removing the holder into a rack or another apparatus. The illustrated embodiment of the holder 200 also has a mechanical key 290 at the other end of connecting member 210. Key 290 is an angled cutout that eases insertion of the holder into a rack, as well as ensures a good registration therein when abutting a complementary angled cut out in a recessed area configured to receive the holder.

A reagent holder for use with a rack as described herein is typically made of a plastic such as polypropylene. The plastic is such that it has some flexibility to facilitate placement into a rack, as further described herein. The plastic is typically sufficiently rigid, however, so that the holder will not significantly sag or flex under its own weight and will not easily deform during routine handling and transport, and thus will not permit reagents to leak out from it.

The holder 200 is typically such that the connecting member 210, process tube 220, the two or more reagent tubes 240, and the waste chamber 260 (if present) are made from a single piece, made from a material such as polypropylene. It will be understood that other configurations of holder 200 can be suitable implemented in the disclosed technology.

Figure 2B:
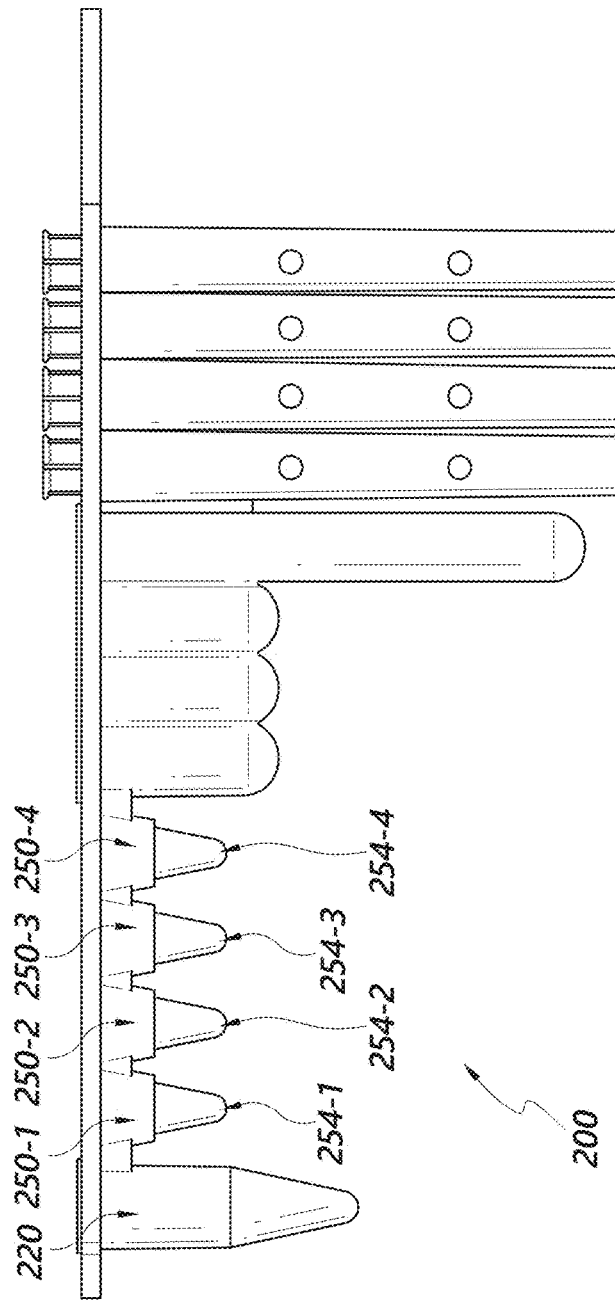
FIG. 2B illustrates a side profile view of an exemplary reagent holder, in accordance with embodiments disclosed herein.
Figure 2C:
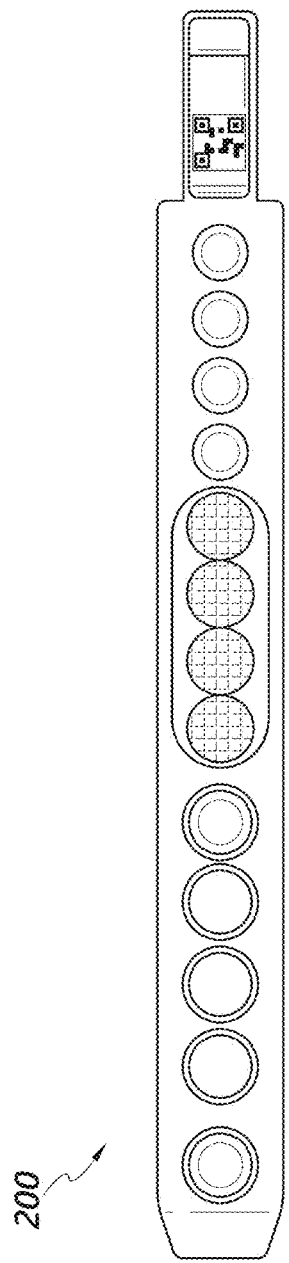
FIG. 2C illustrates a top-down view of an exemplary reagent holder, in accordance with embodiments disclosed herein.

The illustrated embodiment of the reagent holder 200 has four receptacles 250 and corresponding containers 254. FIG. 2B illustrates a side profile view of this embodiment of the reagent holder 200, and FIG. 2C illustrates a top-down view of this embodiment of the reagent holder 200. It can be seen that the four receptacles 250 (e.g., receptacles 250-1, 250-2, 250-3, and 250-4) are configured to accept corresponding containers 254 (e.g., containers 254-1, 254-2, 254-3, 254-4). Some of the containers 254 may contain quantities of one or more reagents typically in solid form, such as in lyophilized form, for carrying out extraction of nucleic acids from a sample that is associated with the holder.

In other embodiments, such as the embodiment of the holder 202 illustrated in FIGS. 2D and 2E, there may be a different number of receptacles 250 and containers 254. For instance, FIG. 2D illustrates a side profile view of an embodiment of the holder 202, with FIG. 2E illustrating a corresponding top-down view of the embodiment of the holder 202. In this embodiment of the reagent holder 202, there are three receptacles 250 (e.g., receptacles 250-1, 250-2, and 250-3) which are configured to accept corresponding containers 254 (e.g., containers 254-1, 254-2, and 254-3). Some of the containers 254 may contain quantities of one or more reagents typically in solid form, such as in lyophilized form, for carrying out extraction of nucleic acids from a sample that is associated with the holder. Although example holders 200 and 202 are described as containing reagents for carrying out extraction of nucleic acids from a sample, it will be understood that the disclosed technology is not limited to holders that contain such reagents and can be suitably implemented on any holders in which magnetic substrates, such as magnetic binding particles, in solution are manipulated or processed.

Figure 3A:
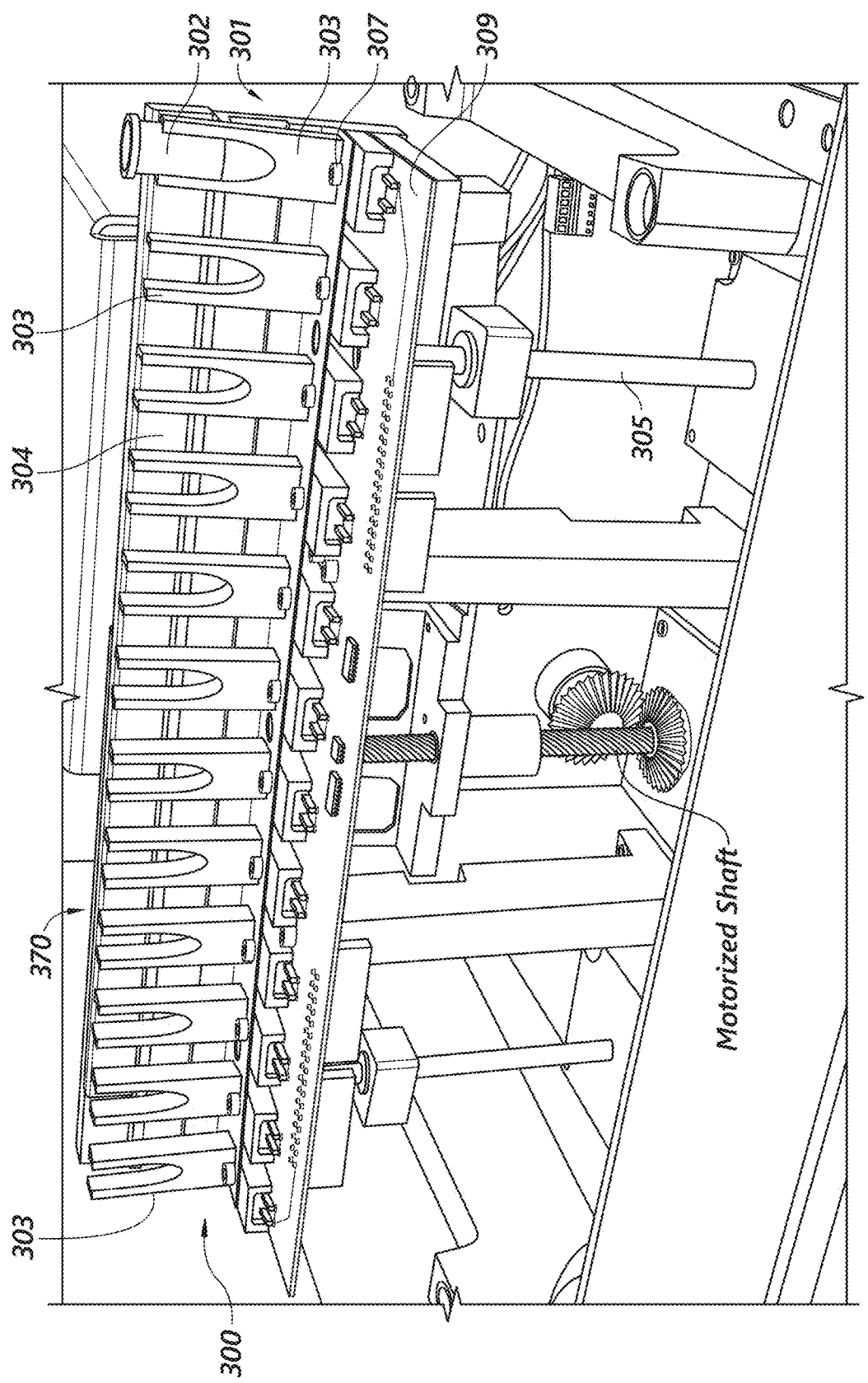
FIG. 3A illustrates an isometric view of an exemplary heater assembly and a magnetic separator, in accordance with embodiments disclosed herein.
Figure 3B:
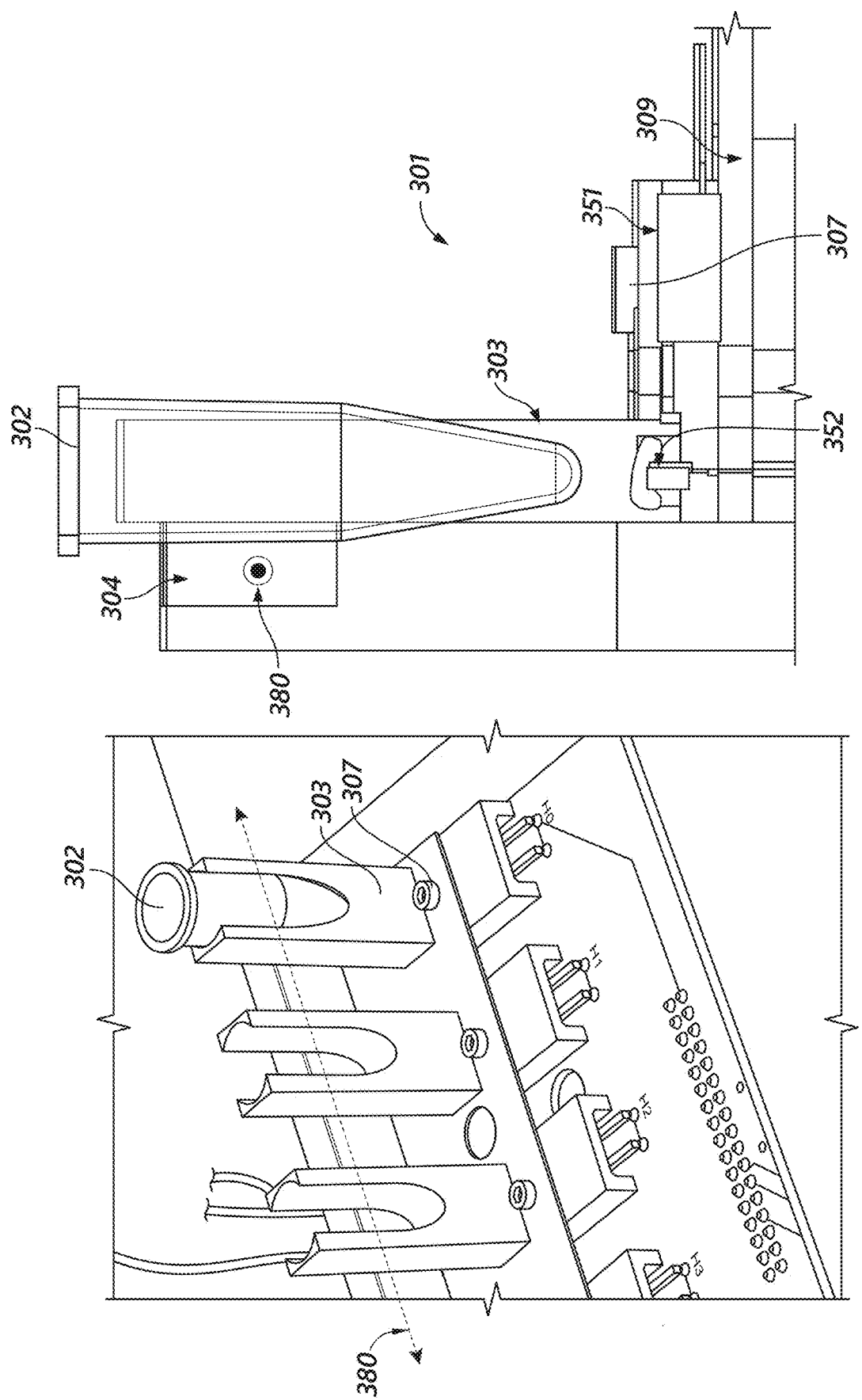
FIG. 3B illustrates an isometric and side profile view of an independently-controllable heater unit of a heater assembly, in accordance with embodiments disclosed herein.
Figure 3C:
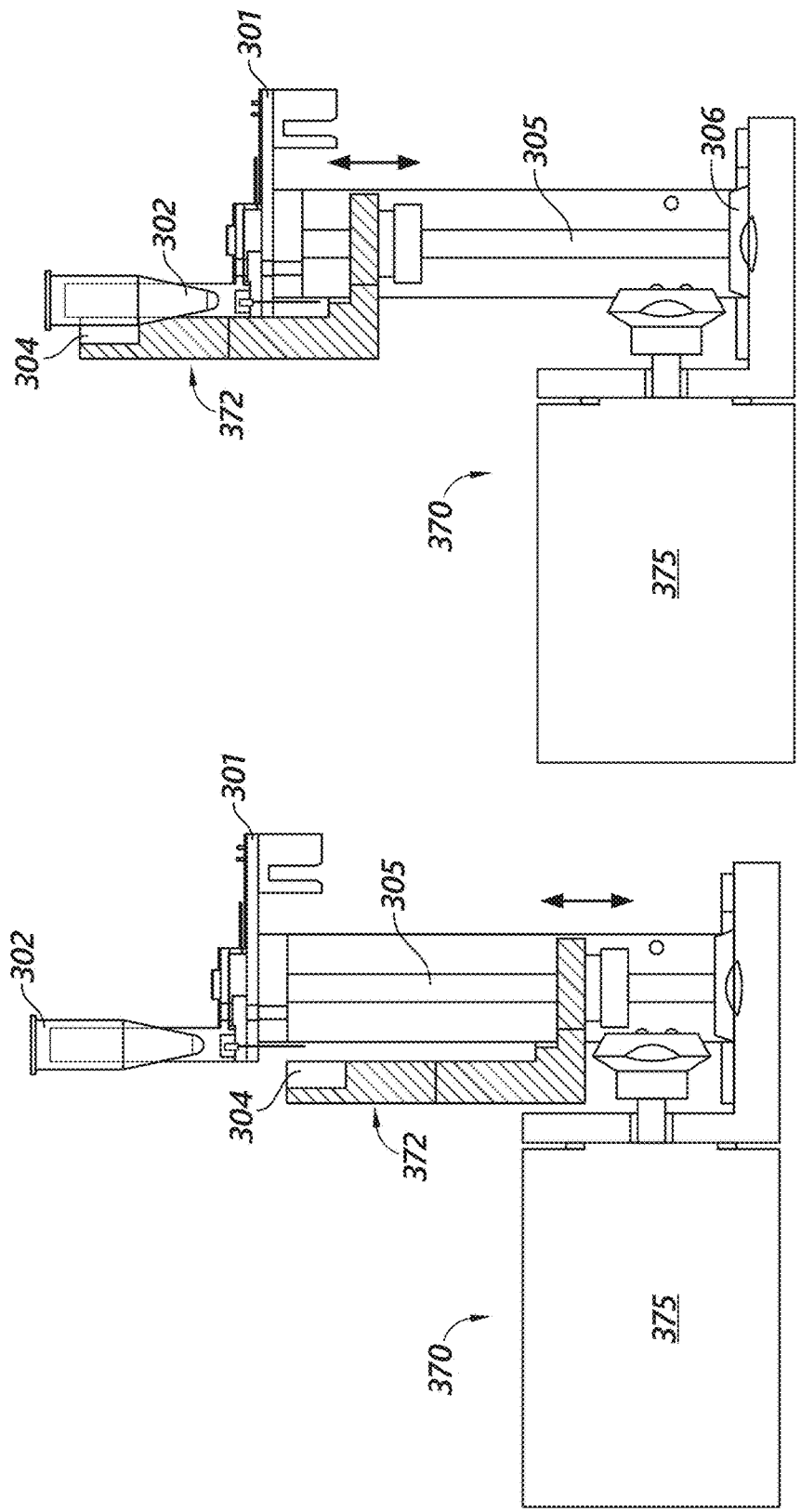
FIG. 3C illustrates a side profile view of a magnetic separator and an independently-controllable heater unit of a heater assembly, which shows the interaction between the magnetic separator and the heater unit, in accordance with embodiments disclosed herein.

Example heater and magnetic separator assemblies that can apply thermal and magnetic energy to the process tube of a plurality of holders will now be described with reference to FIGS. 3A-3C. It will be understood that embodiments of the disclosed technology can be suitably implemented in other heater and magnetic separator assemblies. FIG. 3A illustrates an isometric view of an exemplary heater assembly 300 having independently controllable heater units and a magnetic separator 370. FIG. 3B provides an isometric and side profile view of one of these independently-controllable heater units 301. FIG. 3C provides a side profile view of the interaction of the magnetic separator 370 with the independently-controllable heater units of the heater assembly 300.

More specifically, the heater assembly 300 shown in FIG. 3A may include one or more independently-controllable heater units 301, each of which comprises a heat block 303. Each of the heat blocks 303 is configured to align with and to deliver heat to a process tube 302. Each heat block 303 can be optionally secured and connected to the rest of the apparatus using one or more fasteners, such as one or more screws 307 or other adhesive device(s). This securing mechanism is not limited to such a configuration.

In certain embodiments there are 2, 3, 4, 5, 6, 8, 10, 12, 16, 20, 24, 25, 30, 32, 36, 40, 48, or 50 heater units in a heater assembly 300. Still other numbers of heater units, such as any number between 6 and 100 are consistent with the description herein. The one or more heat blocks 303 may be fashioned from a single piece of metal or other material, or may be made separately from one another and mounted independently of one another or connected to one another in some way. Thus, the term heater assembly connotes a collection of heater units but does not require the heater units or their respective heat blocks to be attached directly or indirectly to one another. The heater assembly 300 can be configured so that each heater unit 301 independently heats each of the one or more process tubes 302 (e.g., the process tube of a reagent holder, such as process tube 220 of the holder 200 shown in FIG. 2A), for example by permitting each of the one or more heat blocks to be independently controllable, as further described herein.

In certain embodiments, there may be a magnetic separator 370. The magnetic separator 370 may be configured to move one or more magnets 304 relative to the one or more process tubes 302 and separate magnetic particles in the process tubes 302. In some embodiments, the magnets 304 may be moved into close proximity to the process tubes 302 (e.g., with each magnet 304 having a face less than 2 mm, between 2 mm and 1 mm, or less than 1 mm away from the exterior surface of a corresponding process tube 302 without being in contact with the process tube 302). The magnets 304 of the magnetic separator 370 may be aligned on a common axis (e.g., a common axis may pass through the midpoints of each of the magnets 304). This common axis may be located behind the process tubes 302 and run parallel to the process tubes 302 (more specifically, run parallel to a common axis passing through all the process tubes 302 when they are disposed in the heat blocks 303). In some cases, this common axis passing through the magnets 304 of the magnetic separator 370 may be referred to as a first magnet axis, such as the example of the first magnet axis 380 shown in FIG. 3B. The magnetic particles may be microparticles, beads, or microspheres capable of binding one or more biomolecules, such as polynucleotides, and commonly available as retention members. Separating the particles, while in solution, typically comprises collecting and concentrating, or gathering, the particles into one location in the inside of the one or more process tubes 302.

Structurally, the magnetic separator 370 may include: one or more magnets 304 affixed to a supporting member; a motorized mechanism configured to move the supporting member in such a manner that the one or more magnets move backwards and forwards along a fixed axis, and during at least a portion of the motion, the one or more magnets maintain close proximity to one or more receptacles which contain the magnetic particles in solution; and control circuitry to control the motorized mechanism. The supporting member and motorized mechanism are not shown in FIG. 3A, but are described in further detail in connection to FIG. 3C.

The magnetic separator 370 may operate together with the heater assembly 300 to permit successive heating and separation operations to be performed on liquid materials in the one or more process tubes without transporting either the liquid materials or the process tubes to different locations to perform either heating or separation. Such operation is also advantageous because it means that the functions of heating and separation which, although independent of one another, are both utilized in sample preparation, may be performed with a compact and efficient apparatus.

In some embodiments, the heater assembly 300 and the magnetic separator 370 can be controlled by electronic circuitry such as on printed circuit board 309. The electronic circuitry can be configured to cause the heater assembly 300 to apply heat independently to the process tubes 302 to minimize the cost of heating and sensing. It can also be configured to cause the magnetic separator 370 to move repetitively relative to the process tubes 302. The electronic circuitry can be integrated into a single printed circuit board (PCB).

In some cases, the magnetic separator 370 can be integrated with the heater assembly 300, and they may be collectively referred to as an integrated magnetic separator and heater assembly. Thus, an integrated magnetic separator and heater may include: a heater assembly, wherein the heater assembly includes a plurality of independently-controllable heater units, each of which has a heat block configured to accept and to heat one of a plurality of process tubes; one or more magnets affixed to a supporting member; a motorized mechanism configured to move the supporting member in such a manner that the one or more magnets move backwards and forwards along a fixed axis, and during at least a portion of the motion the one or more magnets maintain close proximity to one or more of the process tubes in the heater assembly, wherein the one or more process tubes contain magnetic particles; and control circuitry to control the motorized mechanism and to control heating of the heater units.

Although not shown in FIG. 3A, an enclosure can cover the magnetic separator 370 and the heater assembly 300 for protection of sub-assemblies below and aesthetics. The enclosure can also be designed to keep the heat blocks 303 spaced apart from one another to ensure efficiency of heating and cooling. The enclosure can be configured to enable sufficient air flow around the process tubes 302 so as not to significantly inhibit rate of cooling. The enclosure can have a gap between it and the heat blocks 303 to facilitate cooling. The magnetic separator 370 and heater assembly 300 can, alternatively, be enclosed by separate enclosures. For instance, the heater assembly 300 can be optionally contained in an enclosure that surrounds the heater units 301 and heat blocks 303. The one or more enclosures can be made of plastic, but is not so limited. The one or more enclosures may be configured to appear aesthetic to a user.

In the specific configuration shown in FIG. 3A, the heater assembly 300 comprises twelve heat blocks 303 aligned parallel to one another. Each heat block 303 is made from aluminum, and has an L-shaped configuration having a U-shaped inlet for accepting a process tube 302. The magnetic separator 370 comprises twelve magnets 304 aligned parallel to one another. Each magnet 304 may be a rectangular block of Neodymium (or other permanent rare earth materials with magnetic fields) disposed behind each heat block 304 and mounted on a supporting member. The magnets 304 may be configured to move up and down relative to the process tubes 302 in the heater assembly 300. This mechanism is described in further detail in connection with FIG. 3C.

Certain embodiments of the automated diagnostic or preparatory apparatus described herein have more than one independently-controlled heater unit 301 in a single heater assembly 300, as further described herein. For example, a single heater assembly 300 may be configured to independently heat 6 or 12 process tubes, and an apparatus may be configured with two or four such heater assemblies 300. It will be understood that embodiments of the disclosed technology can be implemented in a heater assembly that does not independently heat each process tube, or that applies heat to a subset of a plurality of process tubes received in the heater assembly.

Although a cross-sectional view of one heat block 303 is shown in the right-hand panel of FIG. 3B, it should be understood that this is consistent with having multiple heat blocks aligned in parallel to one another and such that their geometric midpoints all lie on a single linear axis (e.g., as in FIG. 3A), though it is not so limited in configuration. Thus, the one or more heat blocks may be positioned at different heights from one another, in groups or, alternately, individually, or may be staggered with respect to one another from left to right, in groups or alternately, or individually. Additionally, and in other embodiments, the heat blocks are not aligned parallel to one another but are disposed at angles relative to one another, the angles being other than 180°. Furthermore, although the heat block 303 shown in FIG. 3B may be one of several that are identical in size, it is consistent with the technology herein that one or more heat blocks may be configured to accept and to heat process tubes of different sizes.

The exemplary heat block 303 in FIG. 3B (right hand panel) is configured to have an internal cavity that partially surrounds a lower portion of process tube 302. In the heat block 303, the internal cavity surrounds the lower portion of process tube 302 on two sides but not the front side (facing away from magnet 304) and not the rear side (adjacent to magnet 304). In other embodiments, heat block 303 is configured to surround the bottom of process tube 302 on three sides, including the front side. Still other configurations of heat block 303 are possible, consistent with the goals of achieving rapid and uniform heating of the contents of process tube 302. In certain embodiments, the heat block is shaped to conform closely to the shape of process tube 302 so as to increase the surface area of the heat block that is in contact with the process tube during heating of the process tube. Thus, although exemplary heat block 303 is shown having a conical, curve-bottomed cavity in which a complementary process tube is seated, other embodiments of heat block 303 have, for example, a cylindrical cavity with a flat bottom. Still other embodiments of heat block 303 may have a rectilinear internal cavity such as would accommodate a cuvette.

Moreover, although heat block 303 is shown as an L-shape in FIG. 3B, which aids in the transmittal of heat from heating element 351 and in securing the one or more heat blocks to the rest of the apparatus, it need not be so, as further described herein. For example, in some embodiments heating element 351 may be positioned directly underneath process tube 302.

In one embodiment, the heat block 303 has a mass of ~10 grams and is configured to heat up liquid samples having volumes between 1.2 ml and 10 µl. Heating from room temperature to 65° C. for a 1 ml biological sample can be achieved in less than 3 minutes, and 10 µl of an aqueous liquid such as a release buffer up to 85° C. (from 50° C.) in less than 2 minutes. The heat block 303 can cool down to 50° C. from 85° C. in less than 3 minutes. The heat block 303 can be configured to have a temperature uniformity of 65±4° C. for heating up 1 ml of sample and 85±3° C. for heating up 10 µl of release buffer. These ranges are exemplary, and the heat block can be suitably scaled to heat other volumes of liquid at rates that are slower and faster than those described. This aspect of the technology is one aspect that contributes to achieving rapid nucleic acid extraction of multiple samples by combination of liquid processing steps, rapid heating for lysis, DNA capture and release and magnetic separation, as further described herein and elsewhere, such as U.S. patent application Ser. Nos. 12/172,208 and 12/172,214, both of which are incorporated herein by reference.

As shown in FIG. 3B, an independently-controller heater unit 301 can also include one or more heating elements (e.g., a power resistor) 351 each of which is configured to thermally interface to a heat block 303 and dissipate heat to it. For example, in one embodiment, a power resistor can dissipate up to 25 Watts of power. Although the heating element 351 is shown placed at the bottom of the heat block 303, it would be understood that other configurations are consistent with the assembly described herein: for example, the heating element 351 might be placed at the top or side of each heat block 303, or directly underneath process tube 302. In other embodiments, the heating element has other shapes and is not rectangular in cross section but may be curved, such as spherical or ellipsoidal. Additionally, the heating element may be molded or shaped so that it conforms closely or approximately to the shape of the bottom of the process tube.

In the embodiment shown in FIG. 3B, the independently-controlled heater unit 301 may further comprise one or more temperature sensors 352, such as resistive temperature detectors, to sense the respective temperatures of each heat block 303. Although a temperature sensor 352 is shown placed at the bottom of the heat block 303, it would be understood that other configurations are consistent with the assembly described herein: for example, the temperature sensor might be placed at the top or side of each heat block 303, or closer to the bottom of process tube 302 but not so close as to impede uniform heating thereof.

Also shown is the printed circuit board (PCB) 309, which enables the heater assembly 300 to apply heat independently to each process tube 302 upon receipt of appropriate instructions.

FIG. 3C provides a cutaway profile view of an independently-controllable heater unit 301 and a magnet 304 of the magnetic separator 370, in order to demonstrate the interaction of the magnetic separator 370 with the independently-controllable heater units of the heater assembly 300.

While the magnet 304 shown in FIG. 3C is shown as a rectangular block, it is not so limited in shape. Moreover, the configuration of FIG. 3C is consistent with either having a single magnet that extends across all the heat blocks 303 in the heater assembly 300, or having multiple magnets operating in concert and aligned to span a subset of the heat blocks 303, for example, aligned collinearly on the supporting member. The magnet 304 can be made of neodymium and can have a magnetic strength of 5,000-15,000 Gauss (Brmax). An example magnet is from K & J Magnetics, Inc. Other suitable magnets can be implemented. The poles of the magnets 304 can be arranged such that one pole faces the heat blocks 303 and the other pole faces away from the heat blocks 303.

The magnet 304 is mounted on a supporting member 372 that can be raised up and down along a fixed axis using a motorized shaft 305. The fixed axis can be vertical. The magnetic separator 370 may have gears 306 that communicate rotational energy from a motor 375 to cause the motorized shaft 304 to raise and lower the magnet 304 relative to the heat block. This geared arrangement may enable the motor 375 to be placed perpendicular to the shaft 305, thereby saving space in the apparatus in which magnetic separator 370 is situated. In other embodiments, the motor 375 is placed underneath shaft 305. It would be understood that other configurations are consistent with the movement of the magnet 304 relative to the process tubes 302, including, but not limited to, moving the magnet 304 from side-to-side, or bringing the magnet 304 down from above.

The motor 375 can be computer controlled to run at a particular speed; for example at a rotational speed that leads to vertical motion of the magnet 304 in the range 1-20 mm/s. The magnetic separator 370 can thus be configured to move repetitively, e.g., up and down, from side to side, or backwards and forwards, along the same axis several times. In some embodiments there is more than one shaft 305 that operates under motorized control. The presence of at least a second shaft has the effect of making the motion of the separator 370 more smooth and acting as a guiding member. In some embodiments, the supporting member 372 rides on one more guiding members to ensure that the supporting member 372 does not, for example, tip, twist, or yaw, or undergo other internal motions while moving (other than that of controlled motion along the axis) and thereby reduce efficacy of the separation.

The supporting member 372 can also be configured to move the magnets 304 between a first position, situated away from the process tubes 302 (e.g., as in the left-hand side of FIG. 3C), and a second position situated in close proximity to the process tubes 302 (e.g., as in the right-hand side of FIG. 3C), and is further configured to move at an amplitude about the second position where the amplitude is smaller than a distance between the first position and the second position as measured along the shaft 305.

Figure 4A:
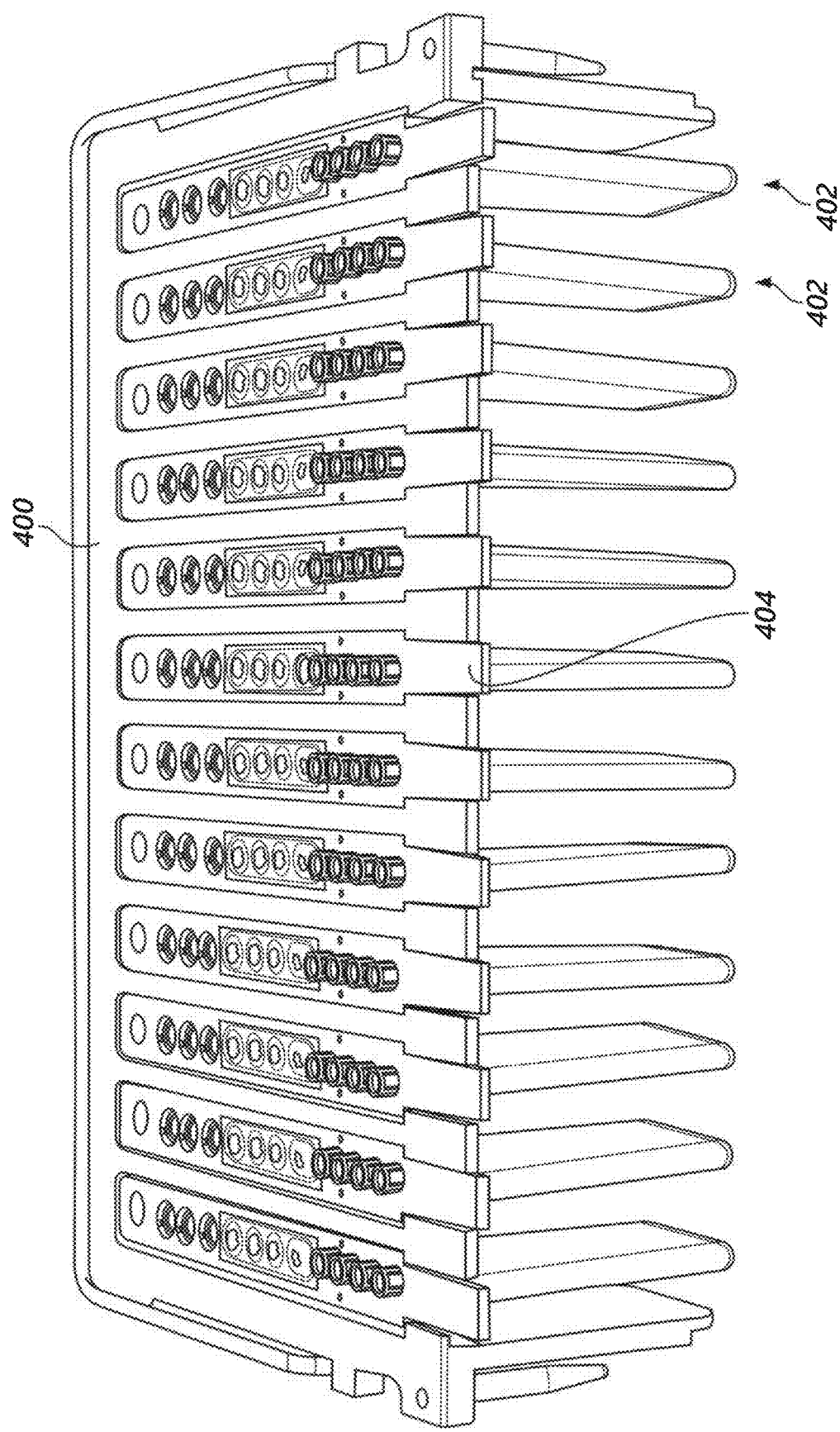
FIG. 4A illustrates a perspective view of a rack for holding reagent holders, in accordance with embodiments disclosed herein.
Figure 4B:
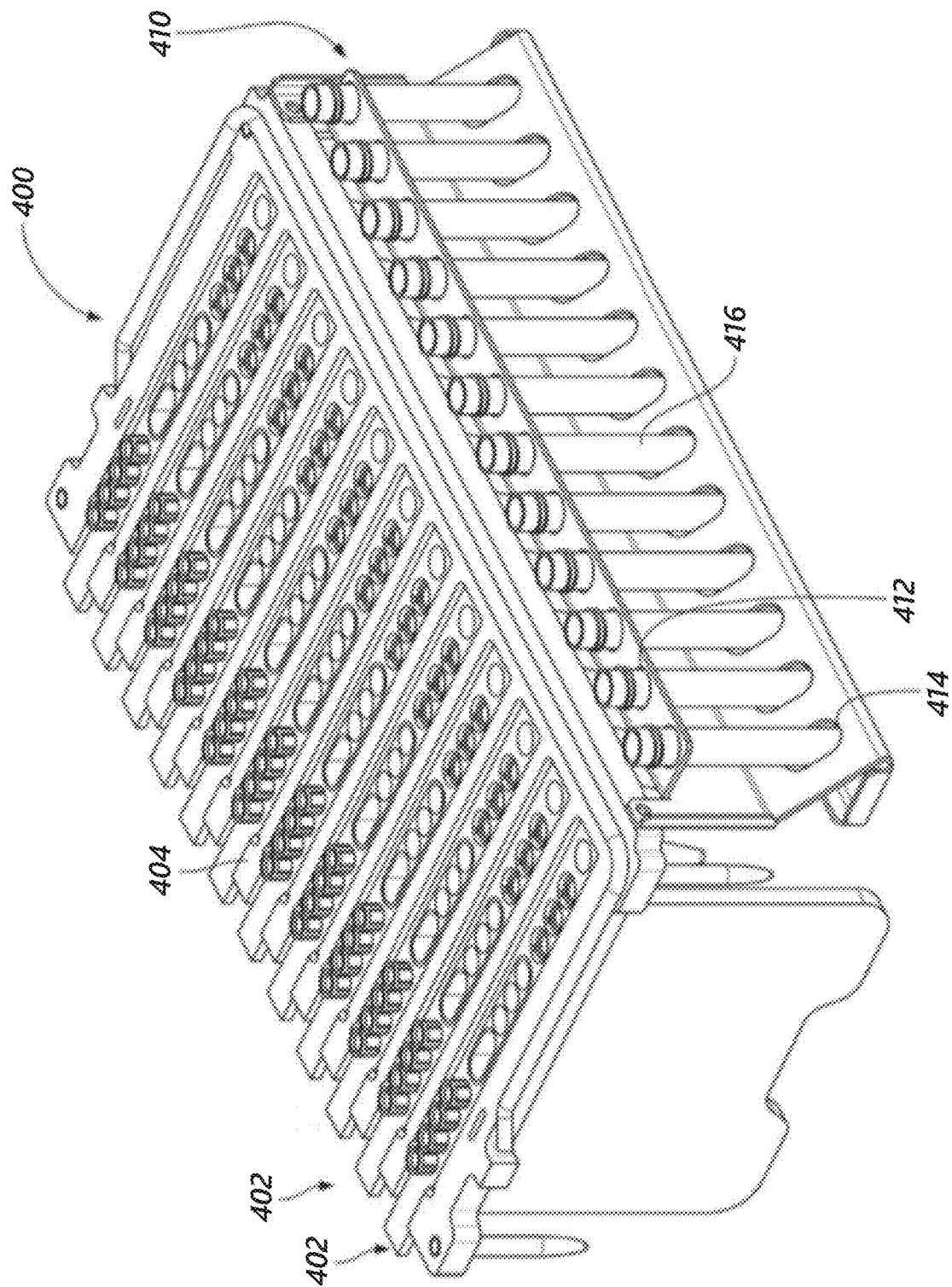
FIG. 4B illustrates an isometric view of a rack for holding reagent holders, in accordance with embodiments disclosed herein.
Figure 5A:
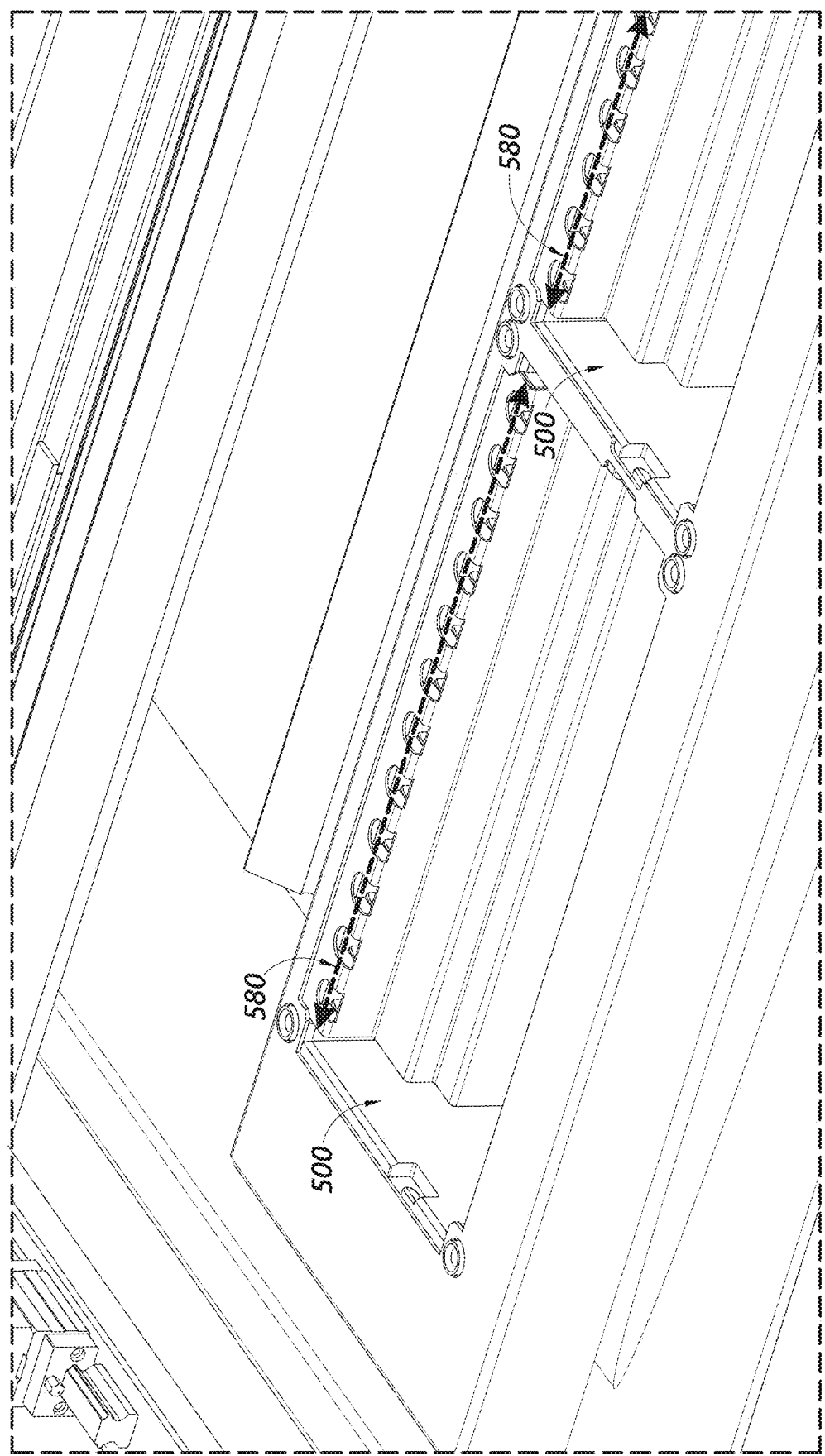
FIG. 5A illustrates an isometric view of an empty loading bay (or receiving bay) of an automated diagnostic or preparatory apparatus, in accordance with embodiments disclosed herein.

FIGS. 4A and 4B illustrate various views of a rack, which can hold multiple reagent holders (e.g., holder 200 shown in FIG. 2A) in pre-defined positions to ensure that the process tubes of the reagent holders (e.g., process tube 220 of the holder 200 shown in FIG. 2A) are precisely disposed in the heater blocks of the heater assembly (e.g., the heater blocks 303 of the heater assembly 300 shown in FIG. 3A) when the rack is loaded into the automated diagnostic or preparatory apparatus described herein. More specifically, FIG. 4A illustrates a perspective view of the back of the rack, while FIG. 4B illustrates an isometric view of the rack. FIGS. 4A and 4B are described together.

An embodiment of a rack 400 is shown, which is configured to be insertable into, and removable from, a loading bay (alternatively, a receiving bay) of an automated apparatus, such as an automated diagnostic apparatus or an automated preparatory apparatus as described herein. An example of a loading bay of an automated apparatus is shown in FIG. 5A. Additional details for such an apparatus are provided in U.S. patent application Ser. No. 12/173,023, filed on Jul. 14, 2008 (entitled "Integrated Apparatus for Performing Nucleic Acid Extraction and Diagnostic Testing on Multiple Biological Samples", in the name of Williams, et al.), and incorporated by reference herein. The automated apparatus may have multiple loading bays, which allows processing of samples in multiple racks at the same time.

Each rack may be configured to receive a plurality of reagent holders. In some examples the rack is also configured to receive a plurality of sample tubes. The apparatus is configured to receive the plurality of reagent holders and the plurality of samples tubes such that the reagent holders are in one-to-one correspondence with the sample tubes, and wherein the reagent holders each contain sufficient reagents to extract polynucleotides from a sample and place the polynucleotides into a PCR-ready form. In implementations in which the rack receives a plurality of sample tubes, the rack may accept any number of sample tubes (e.g., 2, 4, 6, 8, 10, 12, 16, or 20 sample tubes) containing samples and a corresponding number of reagent holders. The rack may be configured to hold the reagent holders in place, either permitting access on a laboratory benchtop to reagents stored in the holders, or situated in a dedicated region of the apparatus permitting the holders to be accessed by one or more other functions of the apparatus, such as automated pipetting, heating of the process tubes, and magnetic separating of affinity beads. The reagent holders may have at least one process tube and one or more containers for reagents. The reagent holders are described in further detail herein (e.g., in connection to FIGS. 2A-2E), and additional details for reagent holders are further provided in U.S. patent application Ser. No. 12/218,416, filed on Jul. 14, 2008 (entitled "Reagent Tube, Reagent Holder, and Kits Containing Same", in the name of Wilson, et al.) and incorporated herein by reference.

For instance, in the embodiment shown in FIGS. 4A and 4B, the rack 400 is configured to accept 12 sample tubes 416 and 12 corresponding reagent holders 404, in 12 lanes 402. A lane 402, as used herein in the context of the rack 400, is a dedicated region of the rack 400 designed to receive a sample tube and corresponding reagent holder 404. In some cases, the reagent holders 404 may be the reagent holders 200 shown in FIG. 2A, which have a process tube 220 at one end. The lanes 402 of the rack 400 may be configured to receive the reagent holders 404 in a certain orientation. For instance, in order to slide each reagent holder 404 into a lane 402, the end of the reagent holder 404 with the process tube may have to be directed towards the lane 402.

For example, in the embodiments shown here, at least the first lane and the second lane are parallel to one another, a configuration that increases pipetting efficiency. Typically, when parallel to one another, pairs of adjacent sample lanes 402 are separated by 24 mm at their respective midpoints. Other distances are possible, such as 18 mm apart, or 27 mm apart. The distance between the midpoints in dependent on the pitch of the nozzles in the liquid dispensing head, as further described herein. Keeping the spacing in multiples of 9 mm enables easy loading from the rack into a 96 well plate (where typically wells are spaced apart by 9 mm). Typically, also, the rack is such that the plurality of reagent holders in the plurality of lanes are maintained at the same height relative to one another.

A lane 402 of the rack 400 may be configured to accept a given reagent holder 404 in such a way that the reagent holder 404 snaps or locks reversibly into place, and thereby remains steady while reagents are accessed in it, and while the rack 400 is being carried from one place to another or is being inserted into, or removed from, a diagnostic or preparatory apparatus. The lanes 402 of the rack 400 can be configured so that the reagent holders 404, when positioned in the rack 400, are aligned for proper pipette tip pick-up using a liquid dispenser as further described herein. Furthermore, in examples where the reagent holder houses one or more pipette tips, the second location of each lane can be deep enough to accommodate one or more pipette tips, such as contained in a pipette tip sheath.

The rack 400 may include a sample tube holder 410 configured to accept a number of sample tubes 416, one for each lane 402. Thus, in the embodiment shown in FIGS. 4A and 4B, the sample tube holder 410 may be configured to accept up to 12 sample tubes 416. For each sample tube 416 that the sample tube holder 410 is configured to hold, the sample tube holder 410 may have a first slot 412 and a second slot 414 that the sample tube 416 is inserted through. Each first slot 412 may have a corresponding second slot 414, and each first slot 412 and its corresponding second slot 414 may be positioned to receive and hold a sample tube 416 at a location adjacent to one of the lanes 402 (e.g., in the same axis as the lane 402, such that the holder 404 inserted in that lane 402 is aligned with the sample tube 416). It will be understood that implementations of the disclosed technology are not limited to racks that include sample tube holders 410 as illustrated in FIGS. 4A-4B, and that implementations of the disclosed technology can be suitably implemented with racks that do not include a sample tube holder 410 and that do not receive sample tubes 416.

FIG. 5A illustrates an isometric view of an empty loading bay 500 (or receiving bay) of an automated diagnostic or preparatory apparatus.

The loading bay 500 may be a recessed area of the apparatus, which is configured to accept a rack such as the exemplary rack 400 of FIGS. 4A and 4B. The apparatus may have any number of loading bays 500 for receiving the corresponding number of racks 400. For instance, FIG. 5A illustrates an embodiment of an apparatus that has two loading bays 500 that are located side-by-side, which allows two separate racks 400 to be simultaneously loaded. Also illustrated in FIG. 5A is a first magnet axis 580, which may be a common axis on which the magnets of the magnetic separator are aligned (e.g., the common axis that passes through the magnets of the magnetic separator). This first magnet axis 580 (similar to the first magnet axis 380 shown in FIG. 3B) may be located behind the process tubes of the reagent holders in the rack 400 when the rack 400 is inserted into the loading bay 500 and run parallel to those process tubes (more specifically, run parallel to a common axis passing through the process tubes).

Figure 5B:
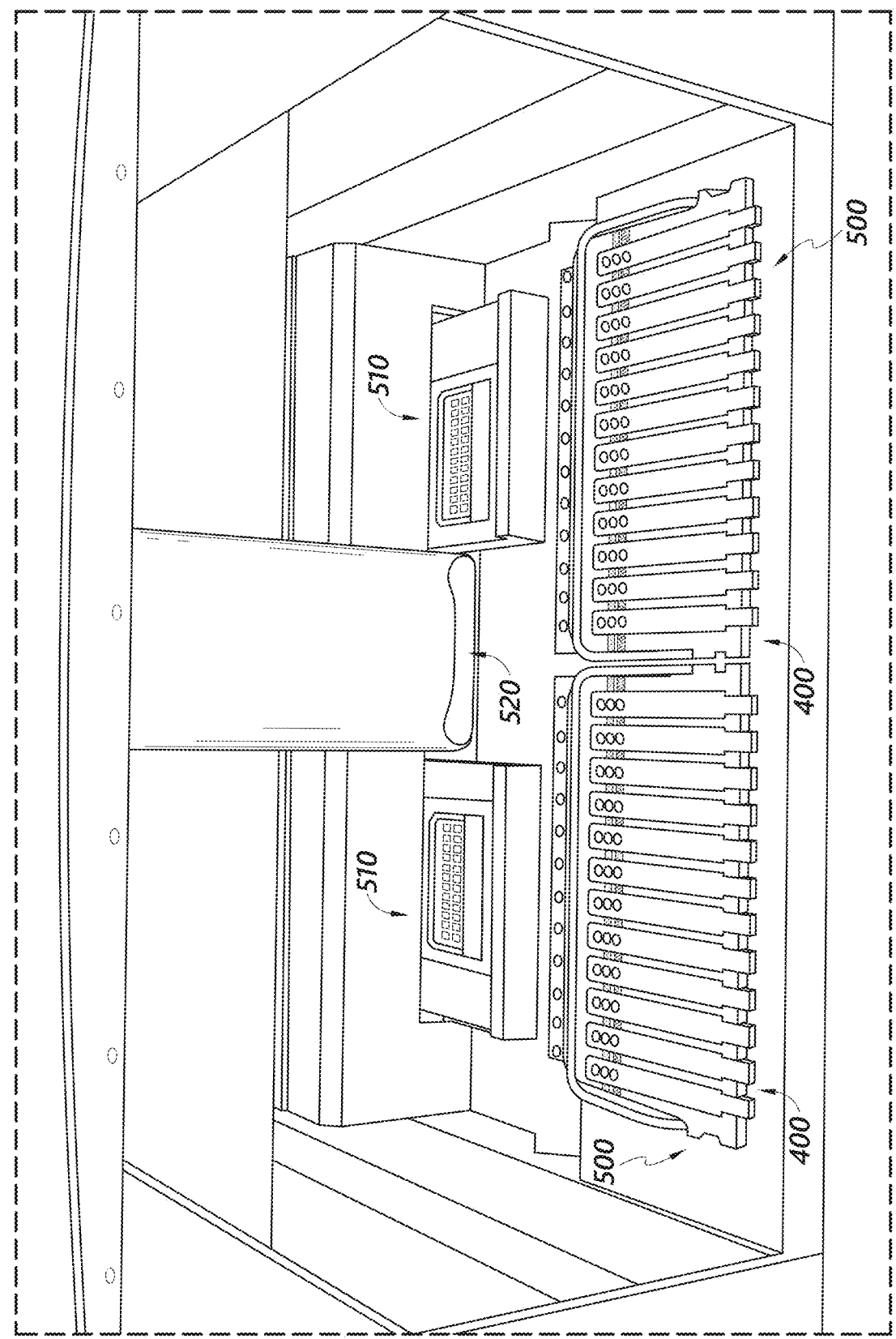
FIG. 5B illustrates a front perspective view of an example automated diagnostic apparatus having two loading bays occupied with corresponding sample racks, in accordance with embodiments disclosed herein.
Figure 6A:
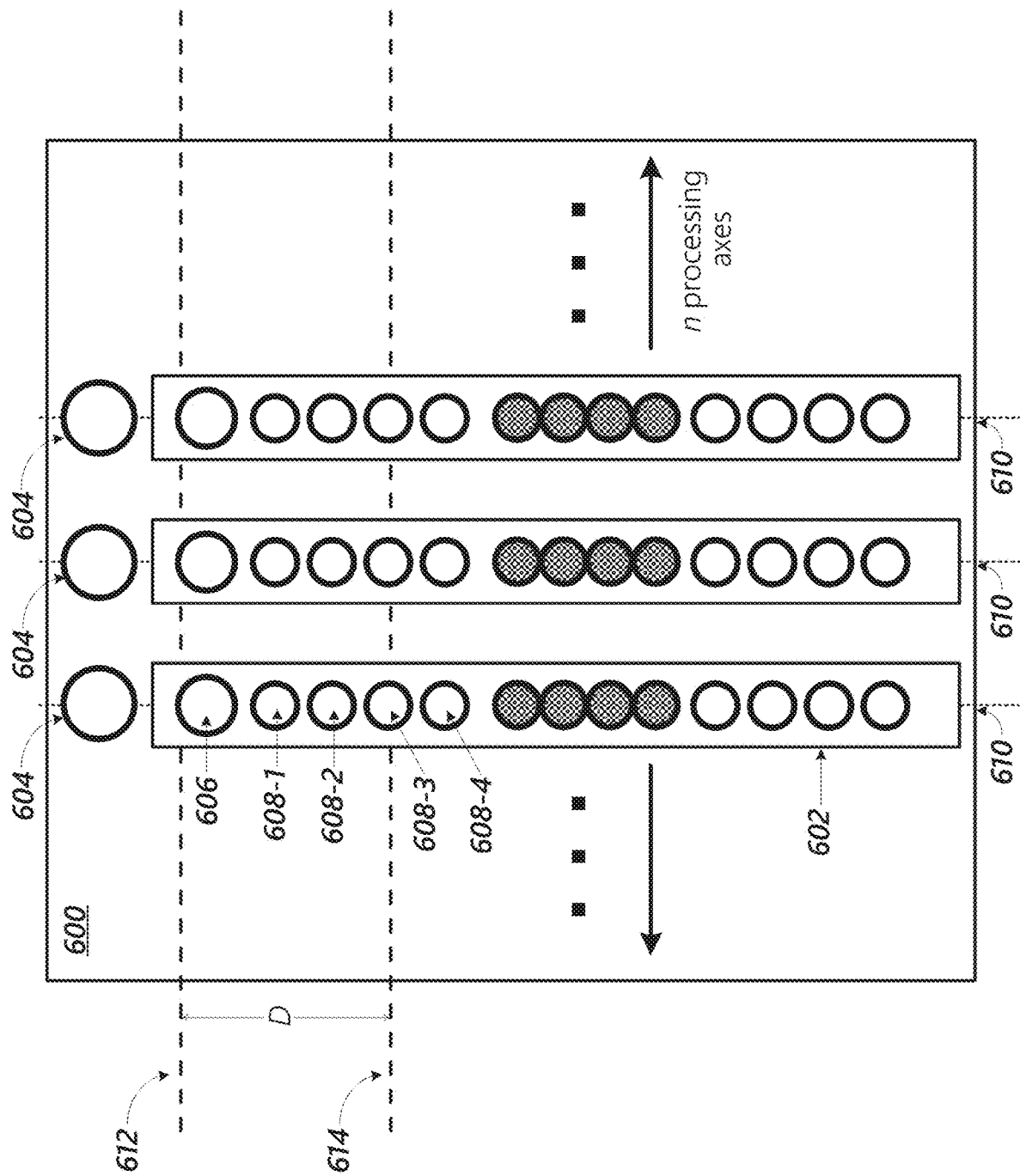
FIG. 6A illustrates a top-down conceptual view of a set of reagent holders in a loading bay or receiving bay of a diagnostic or preparatory apparatus, in accordance with embodiments disclosed herein.
Figure 6B:
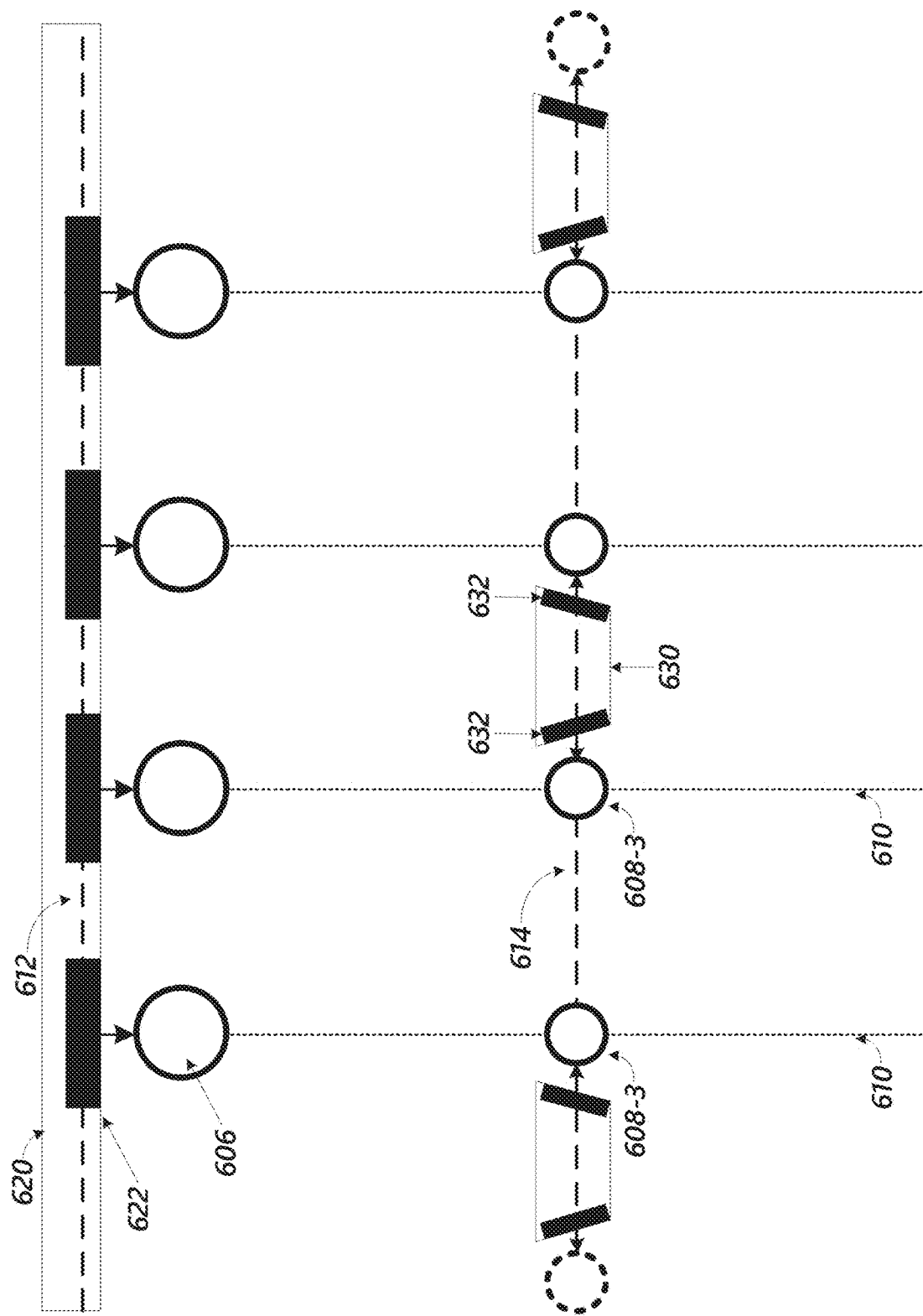
FIG. 6B illustrates a top-down conceptual view of the positions of certain components of the reagent holders of FIG. 6A relative to magnets in a diagnostic or preparatory apparatus, in accordance with embodiments disclosed herein.
Figure 6C:
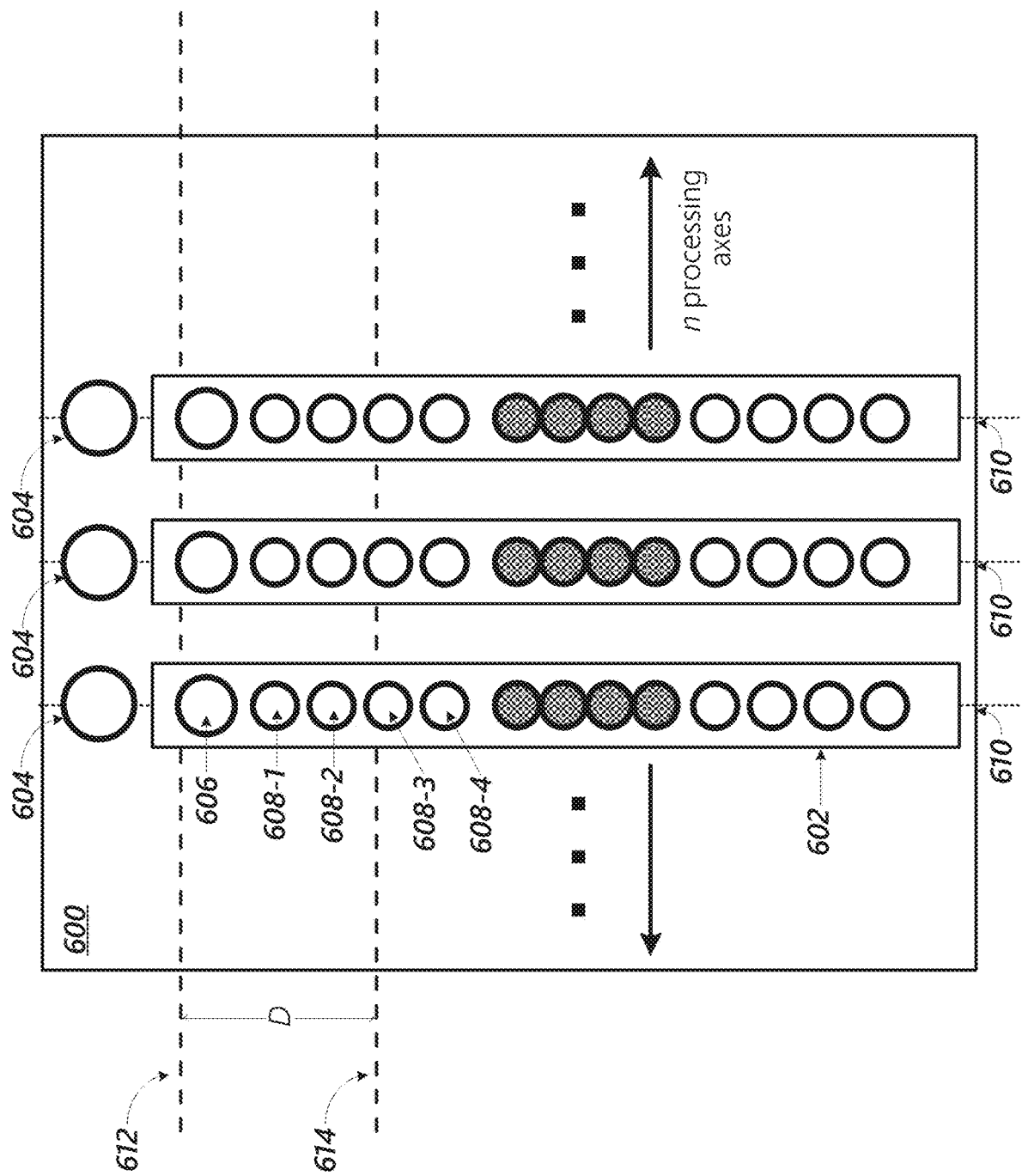
FIG. 6C illustrates a top-down conceptual view of another set of reagent holders in a loading bay or receiving bay of a diagnostic or preparatory apparatus, in accordance with embodiments disclosed herein.

FIG. 5B illustrates a front perspective view of an example automated diagnostic apparatus having two loading bays 500 occupied with corresponding sample racks 400. These loading bays 500 are shown in relation to two microfluidic cartridges 510, which can be configured to carry out an amplification on a suitably prepared sample, as further described in U.S. patent application Ser. No. 12/173,023, filed on Jul. 14, 2008 (entitled "Integrated Apparatus for Performing Nucleic Acid Extraction and Diagnostic Testing on Multiple Biological Samples", in the name of Williams, et al.). Other suitably configured recessed areas for receiving other racks differing in shape, appearance, and form, rather than function, are consistent with the description herein.

Also shown is a liquid dispensing head 520, which may be an automated pipette head used to perform liquid processing operations. An exemplary automated pipette head is described in U.S. patent application Ser. No. 12/173,023, filed Jul. 14, 2008 (entitled "Integrated Apparatus for Performing Nucleic Acid Extraction and Diagnostic Testing on Multiple Biological Samples", in the name of Williams, et al.).

The liquid dispensing head 520 can pick up pipette tips (for example, from the one or more sockets in a reagent holder, such as one of the reagent holders 404 in the racks 400) and return pipette tips (for example, to such sockets in a reagent holder after use); strip and discard a pipette tip from a pipette head after use or upon encountering an error; and move a pipette tip with precision from one location of a given holder to another so that, for example, liquid reagents can be located and added to solid reagents to make up solutions, and various liquid reagents can be mixed with one another during a sample preparation protocol. Furthermore, it is desirable that such a liquid dispensing head 520 can operate on several holders (e.g., 2, 3, 4, or 6) in a rack 400 simultaneously, and thereby perform certain operations in parallel. The liquid dispensing head 520 can move in three degrees of freedom.

Example Fixed Magnet Assemblies According to the Disclosed Technology

FIGS. 6A-6E illustrate various conceptual views associated with implementing a fixed magnet assembly for preventing extraction particle carryover in accordance with the disclosed technology. These conceptual views provide contextual details helpful for understanding how the addition of a fixed magnet assembly prevents extraction particle carryover in implementations of the disclosed technology.

FIG. 6A is a top-down conceptual view of a set of 3 reagent holders 602 in a loading bay or receiving bay 600 of a diagnostic or preparatory apparatus. FIG. 6A illustrates how the reagent holders 602 are arranged relative to a first magnet axis 612 (e.g., off a magnetic separator) and a second magnet axis 614 (of a fixed magnet assembly according to the disclosed technology). As will be described below, one or a plurality of magnets of a magnetic separator described above with reference to FIGS. 3A-3C can be aligned along the first magnet axis 612. A set of 3 sample tubes 604 in associated with the reagent holders 602 are also shown adjacent to the reagent holders 602. In practice, there could be more than 3 reagent holders 602 (and more than 3 corresponding sample tubes 604) in the receiving bay 600, such as the 12 reagent holders held in the rack 400. For each reagent holder 602, some of its associated components are shown, including a process tube 606 (e.g., the process tube 220 shown in FIG. 2A) and a set of containers 608 (e.g., containers 254 shown in FIG. 2A). Each reagent holder 602 and its corresponding sample tube 604 may be aligned along a processing axis 610, with the diagnostic or preparatory apparatus configured to perform processing and operations (e.g., the transfer of liquids) along each processing axis 610. Accordingly, a total of n processing axes 610 may be conceptualized—one for each reagent holder 602 and its corresponding sample tube 604.

It will be understood that in some embodiments, the processing axes 610 does not include a sample tube 604 (for example if the sample tube 604 is received in a different part of the apparatus that is not in association with a reagent holder 602). In such an example, the processing axis 610 may be defined by the location of the process tube 606 and a location of a container that receives magnetic energy from magnets aligned along the second magnet axis 614 (in the illustrated embodiment, container 608-3).

In some embodiments, each of the reagent holders 602 may be similar to the reagent holder 200 shown in FIGS. 2A-2C. In other words, the reagent holders 602 may be an embodiment with four snap-in containers 608 (e.g., containers 254 in FIG. 2A), which include container 608-1, 608-2, 608-3, and 608-4 (numbered in order from nearest to furthest away from the process tube 606). In such cases, the process tube 606 may be alternatively referred to as either a reaction tube or a lysis tube, container 608-1 may be alternatively referred to as an extraction tube, and container 608-3 may be alternatively referred to as a mixing tube. It will be understood that alternative reagent holders 602 can be implemented in embodiments of the disclosed technology. For example, a plurality of reagent holders 602 may be joined or formed as a single, monolithic processing device that is configured to be received in the receiving bay. For another example, a unitary device including a plurality of the reagent holders 602 may be received in the receiving bay.

A first magnet axis 612 may run horizontally behind the process tubes 606 of the reagent holders 602. The first magnet axis 612 may be an axis on which the magnets of a magnetic separator (e.g., the magnets 304 of the magnetic separator 370 shown in FIGS. 3A and 3C) reside. The first magnet axis 612 may be positioned, such that, when the magnetic separator is raised, the magnets of the magnetic separator come into close proximity with the process tubes 606 (e.g., within 2 mm of the process tubes 606).

In accordance with embodiments of the fixed magnet assembly of the disclosed technology, a second magnet axis 614 may run horizontally through the containers 608-3 of the reagent holders 602. Alternatively, the second magnet axis 614 can run behind or in front of the containers 608-3, in either case in close enough proximity to impart a magnetic force on the contents of the container 608-3. The second magnet axis 614 may be an axis on which the magnets of a fixed magnet assembly reside. The second magnet axis 614 may be positioned, such that the magnets of the fixed magnet assembly are in sufficiently close proximity with the containers 608-3 (e.g., the mixing tubes) of the reagent holders 602, so as to impart a magnetic force on the contents of the containers 608-3. The magnetic force can be of a sufficient strength to hold magnetic binding particles in solution in the container 608-3 against an interior wall of the container 608-3, for example while the solution is being transferred out of the container 608-3 during a pipetting operating. Additionally, the second magnet axis 614 may be spaced far enough apart from the first magnet axis 612 such that the magnets of the fixed magnet assembly do not interfere with the magnet of the magnetic separator. For example, the first magnet axis 612 can be spatially separated from the second magnet axis 614 a distance "D" such that the one or more magnets aligned along the first magnet axis 612 do not exert a magnetic force on contents of the containers 608-3, and one or more magnets aligned along the second magnet axis 614 do not exert a magnetic force on contents of the process tubes 606.

The first magnet axis 612 and the second magnet axis 614 are further shown in FIG. 6B, which is a top-down conceptual view of the positioning of certain components of the reagent holders 602 relative to magnets on the first magnet axis 612 and magnets on the second magnet axis 614.

More specifically, FIG. 6B shows for 4 reagent holders, including the positions of the process tube 606, the snap-in container 608-3, and the processing axis 610 associated with each reagent holder. It can be seen that the magnetic separator 620 includes multiple magnets 622 that are aligned on the first magnet axis 612, and each magnet 622 is positioned adjacent to the process tube 606 of a reagent holder. In this example implementation, the magnets 622 are in one-to-one correspondence with the process tubes 606. In practice, when the magnetic separator 620 is raised to bring the magnets 622 into close proximity to the process tubes 606, the magnets 622 exert a magnetic force (shown as vertical vectors in FIG. 6B) on the contents of the process tubes 606.

Also shown in FIG. 6B are the magnets 632 of a fixed magnet assembly according to the disclosed technology. In this example implementation, a single magnet 632 exerts a magnetic force on two containers 608-3, such that the magnets 632 are not in one-to-one correspondence with the containers 608-3. In some embodiments, the magnets 632 of the fixed magnet assembly can be arranged in pairs. Each pair of magnets 632 can be located within a housing or structure 630. A fixed magnet assembly may include multiple housings 630. In one non-limiting embodiment, a plurality of housings 630 are formed in a unitary structure and each housing is configured to house or enclose two magnets 632. In another non-limiting embodiment, the fixed magnet assembly includes a unitary structure formed of a magnetic material, the unitary structure including a plurality of magnet structures 630 configured to exert a magnetic force on containers 608-3. The pairs of magnets 632 can be positioned within the diagnostic or preparatory apparatus, such that each pair of magnets 632 is located between the containers 608-3 of two adjacent reagent holders (in the manner shown in the figure) when the reagent holders are in the receiving bay of the diagnostic or preparatory apparatus. There may be a magnet 632 for each reagent holder and when the reagent holders are in the receiving bay of the diagnostic or preparatory apparatus, each magnet 632 may be in close proximity with the container 608-3 of a reagent holder. All of the magnets 632 of the fixed magnet assembly may be aligned on (or substantially aligned on) the second magnet axis 612. Each of the magnets 632 may exert a magnetic force (shown as horizontal vectors in FIG. 6B) on the contents of adjacent containers 608-3.

Implementations of fixed magnet assemblies according to the disclosed technology can include any suitably configured magnet. In one non-limiting example, the individual magnets 632 are 0.25×0.25×0.0625" NdFeB, Grade N52 square magnets, that have a pull force of 1.77 lbs and field strength of 3032 Gauss. It will be understood that the material, dimensions, and pull force is not limited to this particular example of the disclosed technology. Suitable magnets may include magnets of various different materials, sizes, and/or strengths, as long as the selected magnet configuration combined with the positioning of the magnets by the mixing tubes enable the magnets to sufficiently capture the magnetic extraction particles in the mixing tubes.

FIG. 6C is similar to FIG. 6A, in that FIG. 6C illustrates a top-down conceptual view of a set of 3 reagent holders 602 in a loading bay or receiving bay 600 of a diagnostic or preparatory apparatus is shown. However, in the embodiment illustrated in FIG. 6C, the second magnet axis 614 does not run through the midpoints of the containers 608-3 of each of the reagent holders 602. Instead, the second magnet axis 614 lies on an off-center chord of each the containers 608-3. This may correspond, for instance, with the embodiment that is shown in FIG. 6D.

Figure 6D:
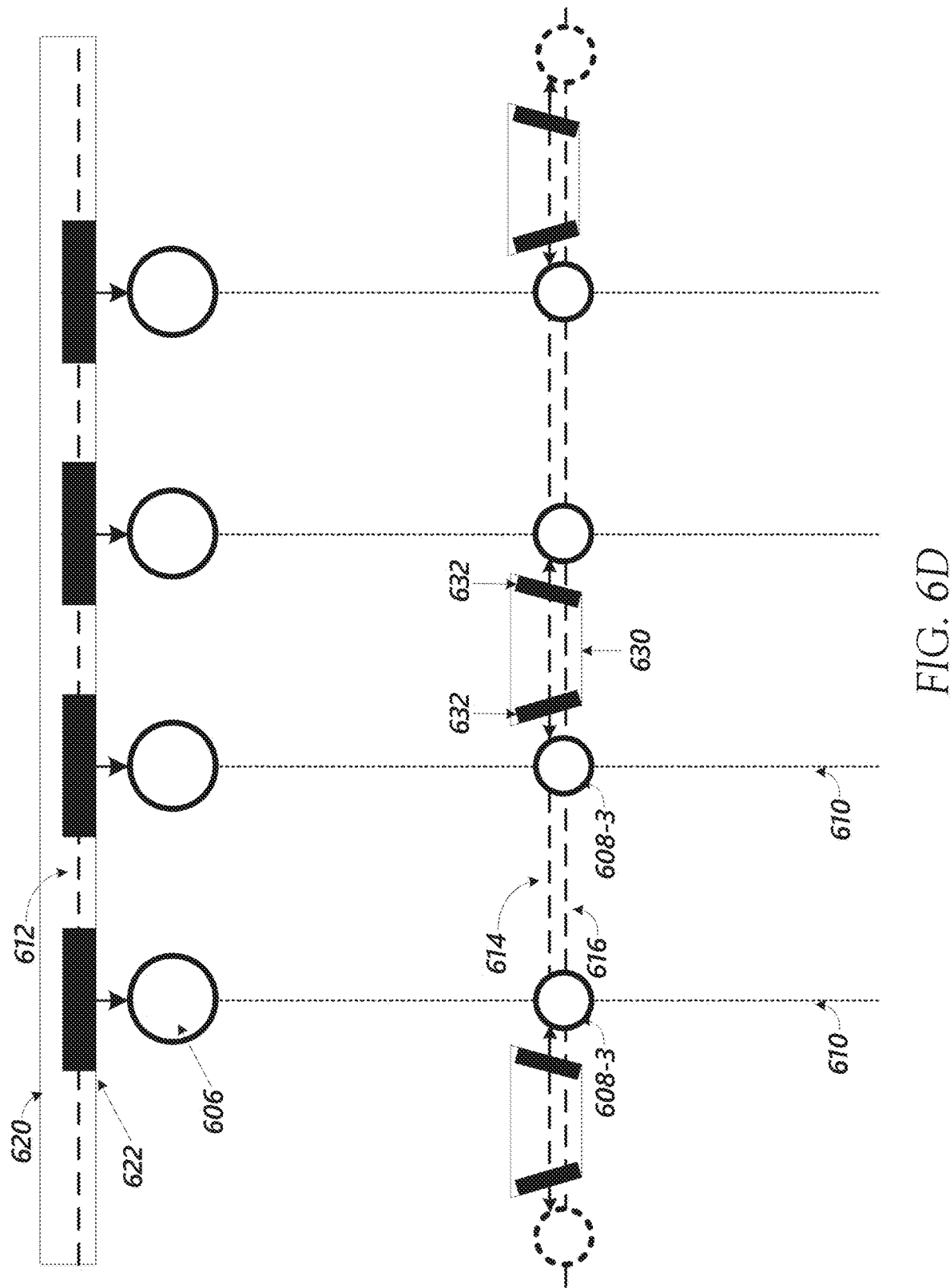
FIG. 6D illustrates a top-down conceptual view of the positions of certain components of the reagent holders of FIG. 6C relative to magnets in a diagnostic or preparatory apparatus, in accordance with embodiments disclosed herein.

FIG. 6D is similar to FIG. 6B, in that FIG. 6D illustrates a top-down conceptual view of the positions of certain components of the reagent holders 602 relative to magnets on the first magnet axis 612 and magnets on the second magnet axis 614. However, in the embodiment illustrated in FIG. 6D, the second magnet axis 614 does not run through the midpoints of the containers 608-3 of each of the reagent holders 602. This second magnet axis 614 is distinct from a mixing axis 616, which passes through the midpoints of the containers 608-3 of each of the reagent holders 602. The magnets 632 are aligned along the second magnet axis 614 that is generally parallel to the first magnet axis 612 and also generally parallel to the mixing axis 616 (but does not coincide with the mixing axis 616). However, the second magnet axis 614 may be close enough to the mixing axis 616, such that the magnets 632 (residing on the second magnet axis 614) may be considered as applying a magnetic force to the contents of each of the containers 608-3 along a direction that is generally parallel to the mixing axis 616. The functions of the magnets 622 of the magnetic separator 620 and the magnets 632 of the fixed magnet assembly may be better understood with additional context provided by FIG. 6E, which is a side profile conceptual view illustrating the positions of a reagent holder 602 and corresponding sample tube 604 in relation to a first magnet 622 (e.g., from the magnetic separator) and a second magnet 632 (e.g., from the fixed magnet assembly) when the reagent holder 602 and corresponding sample tube 604 are in the receiving bay of the diagnostic or preparatory apparatus.

Figure 6E:
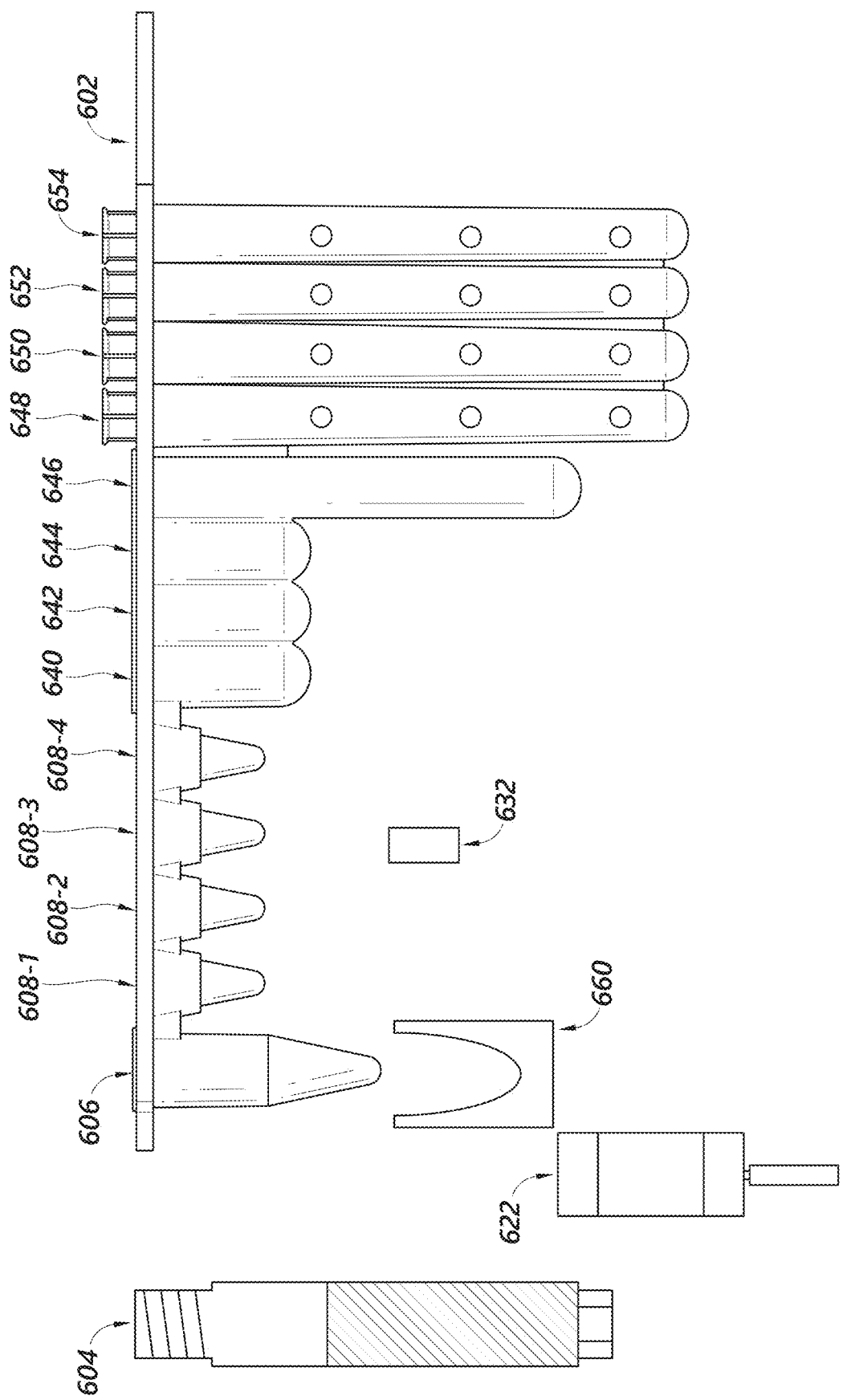
FIG. 6E illustrates a side profile conceptual view of the positions of certain components of a reagent holder relative to magnets in a diagnostic or preparatory apparatus, in accordance with embodiments disclosed herein.

More specifically, FIG. 6E shows a reagent holder 602 having a process tube 606, a set of 4 snap-in containers 608 (e.g., containers 608-1, 608-2, 608-3, and 608-4), a set of reagent tubes (e.g., reagent tubes 640, 642, and 644), a waste chamber 646, and a set of pipette tips disposed within pipette sheaths (e.g., pipette tips 648, 650, 652, and 654). Although the illustrated embodiment of the reagent holder 602 has 4 snap-in containers 608, it should be noted that embodiments of the disclosed technology can be suitable implemented with the reagent holders with 3 snap-in containers 608 described with reference to FIGS. 2D-2E (e.g., without the container 608-4).

Process tube 606 (similar to process tube 220 shown in FIG. 2A) may typically be used during sample preparation for cell lysis and extraction of nucleic acids, such as DNA or RNA of a patient, and DNA or RNA of a pathogen. The process tube 606 may be positioned at the distal end of the reagent holder 602 in a location that minimizes, overall, pipette head moving operations involved with transferring liquids to the process tube 606 when the reagent holder 602 is in the receiving bay of the diagnostic or preparatory apparatus. The process tube 606 is also positioned in a location such that the process tube 606 is disposed within a heater block 660 of a heater assembly (e.g., as shown in FIGS. 3A and 3B) when the reagent holder 602 is in the receiving bay of the diagnostic or preparatory apparatus. The first magnet 622 of the magnetic separator may be raised to be in close proximity to the process tube 606 in order to exert a magnetic force on the contents of the process tube 606.

Some of the containers 608 may contain lyophilized reagents (e.g., dried reagents) to which fluid may be added. In some embodiments, container 608-1 may be alternatively referred to as an extraction tube. In some embodiments, container 608-3 may be alternatively referred to as a mixing tube. In some embodiments, containers 608-2 and 608-4 may be alternatively referred to as master mix tubes. The reagent tubes 640, 642, and 644 may contain liquid reagents, one per tube. In some embodiments, the reagent tube 640 may contain a wash buffer. In some embodiments, the reagent tube 642 may contain an elution buffer. In some embodiments, the reagent tube 644 may contain a neutralization buffer. The wash buffer, release buffer, and neutralization buffer may each be used in a sample preparation protocol. Spent liquid reagents can be transferred to the waste chamber 646, where they can be later disposed of.

The set of 4 pipette tips (e.g., pipette tips 648, 650, 652, and 654) may be disposed within pipette sheaths. The pipette tips may be used by the diagnostic or preparatory apparatus (e.g., via the liquid dispensing head 520) to perform processing and operations (e.g., the transfer of liquids). The pipette sheaths may serve to catch drips from used pipette tips, and thereby prevent cross-sample contamination, from use of one holder to another in a similar location, and/or to any supporting rack in which the holder is situated. The pipette sheaths may be permanently or removably affixed to the reagent holder 602, or may be formed, e.g., molded, as a part of a single piece assembly for the holder 602.

Preparation of a sample with the additional fixed magnet assembly may proceed as follows. It should be noted that the following description of an example workflow is provided to provide context for understanding the role of the fixed magnet assembly and the steps are not applicable to all assays, which may use other workflows that have different process steps or order of operations. In some embodiments, the liquid dispensing head of the diagnostic or preparatory apparatus may first pick up the first pipette tip 648 and use it to pierce (e.g., obtain access) to various components of the reagent holder 602, including the container 608-1, the waste chamber 646, and the reagent tubes 640, 642, and 644 (containing the wash buffer, release buffer, and neutralization buffer, respectively).

The liquid dispensing head of the diagnostic or preparatory apparatus may use the first pipette tip 648 to transfer some raw sample from the sample tube 604 and add it to the process tube 606. The amount of raw sample transferred may depend on the type of assay or procedure. Some of the sample (e.g., the remainder of the sample not transferred into the process tube 606) may be added to the container 608-1 (e.g., the extraction tube), which may contain magnetic particles (e.g., beads), a lyophilized extraction reagent (e.g., dried lysis reagent), and internal controls. The magnetic particles may be configured to bind to specific molecules (e.g., DNA/RNA) in the sample. The contents of the container 608-1 are rehydrated using the added sample and given time to dissolve into solution. The liquid dispensing head may then use the first pipette tip 648 to transfer the contents of the container 608-1 into the process tube 606 (which contains the rest of the transferred sample from the sample tube 604) and mix the contents of the process tube 606. Afterwards, the liquid dispensing head may return the first pipette tip 648 to its pipette sheath.

The contents of process tube 606, which is disposed in the heater block 660 (e.g., the process tube 606 is received within the heater block 660) of a heater unit of a heater assembly of the diagnostic or preparatory apparatus, are heated by the heater block 660. The temperature and duration of the heating is determined by the type of assay or procedure. The heating and lysis reagent causes the cells from the sample to break open, and some of the target nucleic acid (for example, DNA or RNA) contained in the cells and the internal controls may attach or bind to the magnetic particles (e.g., magnetic binding particles or beads).

The first magnet 622 of the magnetic separator may be raised until it is in close proximity to the process tube 606. The magnet 622 may exert a magnetic force on the magnetic particles in the process tube 606, drawing the magnetic particles and the attached nucleic acid to the side of the process tube 606. The liquid dispensing head may use the first pipette tip 648 to extract the liquid from the process tube 606 while the magnet 622 is still drawing the magnetic particles and attached nucleic acid to the side of the process tube 606. Ideally under normal operating, this liquid should not contain the magnetic particles and attached nucleic acid, which are held against the inner side wall of the process tube 606 as the liquid is extracted. The liquid dispensing head may dispense the extracted liquid to the waste chamber 646 and return the first pipette tip 648 to its pipette sheath.

The first magnet 622 of the magnetic separator may be lowered, thereby removing the magnetic force holding the magnetic particles and the attached nucleic acid to the side of the process tube 606. The liquid dispensing head may use the second pipette tip 648 to transfer wash buffer from the reagent tube 640 to the process tube 606. The second pipette tip 650 can also be used to mix the added wash buffer with the magnetic particles bound to nucleic acid in the process tube 606. Afterwards, the first magnet 622 of the magnetic separator may be raised against until it is in close proximity to the process tube 606. The magnet 622 may exert a magnetic force on the magnetic particles in the process tube 606, again drawing the magnetic particles and the attached nucleic acid to the side of the process tube 606.

With the magnetic particles moved to the side of the process tube 606, the liquid dispensing head may use the second pipette tip 650 to extract the liquid contents (e.g. primarily the added wash buffer) of the process tube 606 and transfer the liquid to the waste chamber 646. Ideally under normal operating conditions, this liquid should not contain the magnetic particles and attached nucleic acid, which are held against the inner side wall of the process tube 606 as the liquid is extracted. Afterwards, the liquid dispensing head may return the second pipette tip 650 back to its pipette sheath and the first magnet 622 of the magnetic separator may be lowered, thereby removing the magnetic force holding the magnetic particles and the attached nucleic acid to the side of the process tube 606.

The liquid dispensing head may then use the third pipette tip 652 to transfer release buffer from the reagent tube 642 to the process tube 606 containing the magnetic particles and attached nucleic acid. The release buffer may cause the magnetic particles to separate from the nucleic acid and internal controls. The liquid dispensing head may then use the third pipette tip 652 to transfer neutralizing buffer from the reagent tube 644 to the snap-in container 608-3 (e.g., mixing tube), which is empty at this point. Afterwards, the liquid dispensing head may return the third pipette tip 652 back to its pipette sheath. At this point, the process tube 606 will contain the magnetic particles, the extracted nucleic acid (e.g., DNA/RNA extracted from the cells and attached to the magnetic particles), and internal controls. The snap-in container 608-3 (e.g., mixing tube) contains neutralizing buffer.

The heater block 660 is activated a second time to heat the contents of the process tube 606. The temperature and duration of the heating will be dependent on the assay or procedure performed. The first magnet 622 of the magnetic separator may be raised yet again, until it is in close proximity to the process tube 606. The magnet 622 may exert a magnetic force on the magnetic particles in the process tube 606, drawing the magnetic particles to the inner side wall of the process tube 606 (but not the nucleic acid, e.g., DNA/RNA molecules, which are no longer attached to the magnetic particles). While the magnetic particles are drawn to and held against the inner side wall of the process tube 606 by the magnet 622, the liquid dispensing head may use the third pipette tip 652 to extract the liquid contents (e.g. the nucleic acid mixture) from the process tube 606 without extracting the magnetic particles. The nucleic acid mixture can be transferred to container 608-3 (e.g., the mixing tube) now containing the neutralizing buffer. The neutralizing buffer is configured to lower the pH of the nucleic acid mixture to a neutral pH. The third pipette tip 652 may be returned to its pipette sheath and the first magnet 622 of the magnetic separator may be lowered.

At this point, for the embodiment of the reagent holder 602 with 4 snap-in containers 608, the liquid dispensing head may use the fourth pipette tip 654 to puncture (e.g., gain access) container 608-2 and/or container 608-4. The containers 608-2 and 608-4 may be alternatively referred to as master mix tubes, and which of these containers are used may depend on the assay or procedure performed. The first master mix tube (e.g., container 608-2) may contain primers and probes to test for a first analyte of interest, and the second master mix tube (e.g., container 608-4) may contain primers and probes to test for a second analyte of interest.

As a very specific example, in some embodiments, the reagent holder 602 may be used to perform an assay of enteric bacteria, and both container 608-2 and container 608-4 may be used. In such cases, the container 608-2 may be referred to as an enteric bacterial panel master mix tube containing enteric bacterial panel master mix for identifying one set or panel of enteric bacteria, and the container 608-4 may be referred to as an extended bacterial panel master mix tube containing extended bacterial panel master mix for identifying a second set or panel of enteric bacteria. Thus, some of the neutralized DNA/RNA mixture from container 608-3 could be transferred to both master mix tubes.

In some embodiments, the reagent holder 602 may be used to extract polynucleotides (e.g., DNA or RNA) from a sample and place the polynucleotides into a PCR-ready form. In such cases, either the snap-in container 608-4 or the snap-in container 608-2 may serve as a PCR master mix tube, which contains PCR master mix (e.g., primers, probes, and other PCR reagents for the PCR reaction). For example, if the snap-in container 608-2 is the PCR master mix tube containing PCR master mix, the liquid dispensing head may first use the fourth pipette tip 654 to puncture (e.g., obtain access to) container 608-2. The liquid dispensing head can then extract the neutralized nucleic mixture in container 608-3 (e.g., the mixing tube) and transfer it to container 608-2. This container 608-3 may be in close proximity with the second magnet 632 (e.g., of a fixed magnet assembly) when the reagent holder 602 is inserted for processing by the diagnostic or preparatory apparatus. Additional context for the possible positions and orientations of the second magnet 632 is provided in FIG. 6B. The second magnet 632 may exert a magnetic force on the contents of the container 608-3 as the liquid dispensing head extracts the neutralized nucleic acid mixture from the container 608-3. In particular, there may be some magnetic particles (e.g., beads) that were transferred into the container 608-3 from the process tube 606 despite efforts to prevent this from occurring (e.g., using the first magnet 622 to keep the magnetic particles in the process tube 606). The second magnet 632 may be used as part of an additional filtering step to remove any leftover magnetic particles carried over from the process tube 606 (e.g., "carryover" magnetic particles) from the neutralized nucleic mixture as it is extracted from container 608-3.

The extracted neutralized nucleic mixture is then transferred to the container 608-2 (e.g., PCR master mix tube). In some embodiments, the PCR master mix in the container 608-2 may be in the form of a lyophilized pellet. Adding the neutralized RNA/DNA mixture may dissolve the PCR master mix pellet. The PCR master mix pellet may be allowed to dissolve, and the liquid dispensing head may use the fourth pipette tip 654 to mix together the contents of the container 608-2. The liquid dispensing head may then use the fourth pipette tip 654 to withdraw the mixed solution (now an amplification-ready sample) from the container 608-2 and transfer it to a device, including a storage device where the sample is stored or a microfluidic cartridge where it is amplified (e.g., the microfluidic cartridges 510 shown in FIG. 5B).

It should be noted that this sample preparation process for extracting and preparing polynucleotides into PCR-ready form can be used with other embodiments of the reagent holder, such as reagent holders with only 3 snap-in containers (e.g., similar to the reagent holder 202 shown in FIGS. 2D and 2E). Without the fourth snap-in container available (e.g., container 608-4), the second snap-in container (e.g., container 608-2) is used as the master mix tube, which will hold the prepared PCR-ready solution that will be transferred to the storage device or the microfluidic cartridge.

Figure 7A:
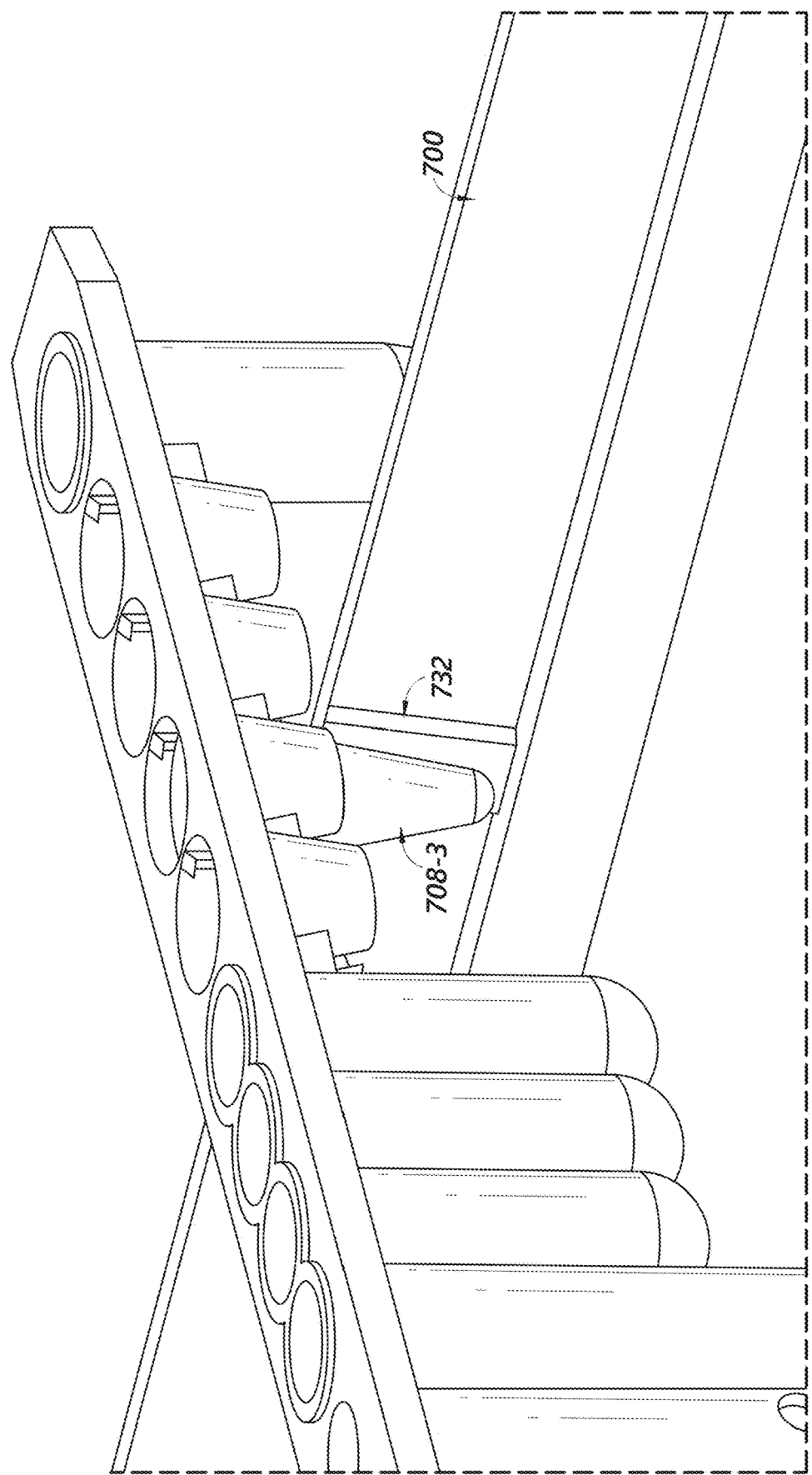
FIGS. 7A-7B illustrate perspective views of an embodiment of a fixed magnet assembly that can be implemented into an automated diagnostic or preparatory apparatus, in accordance with embodiments disclosed herein.
Figure 7B:
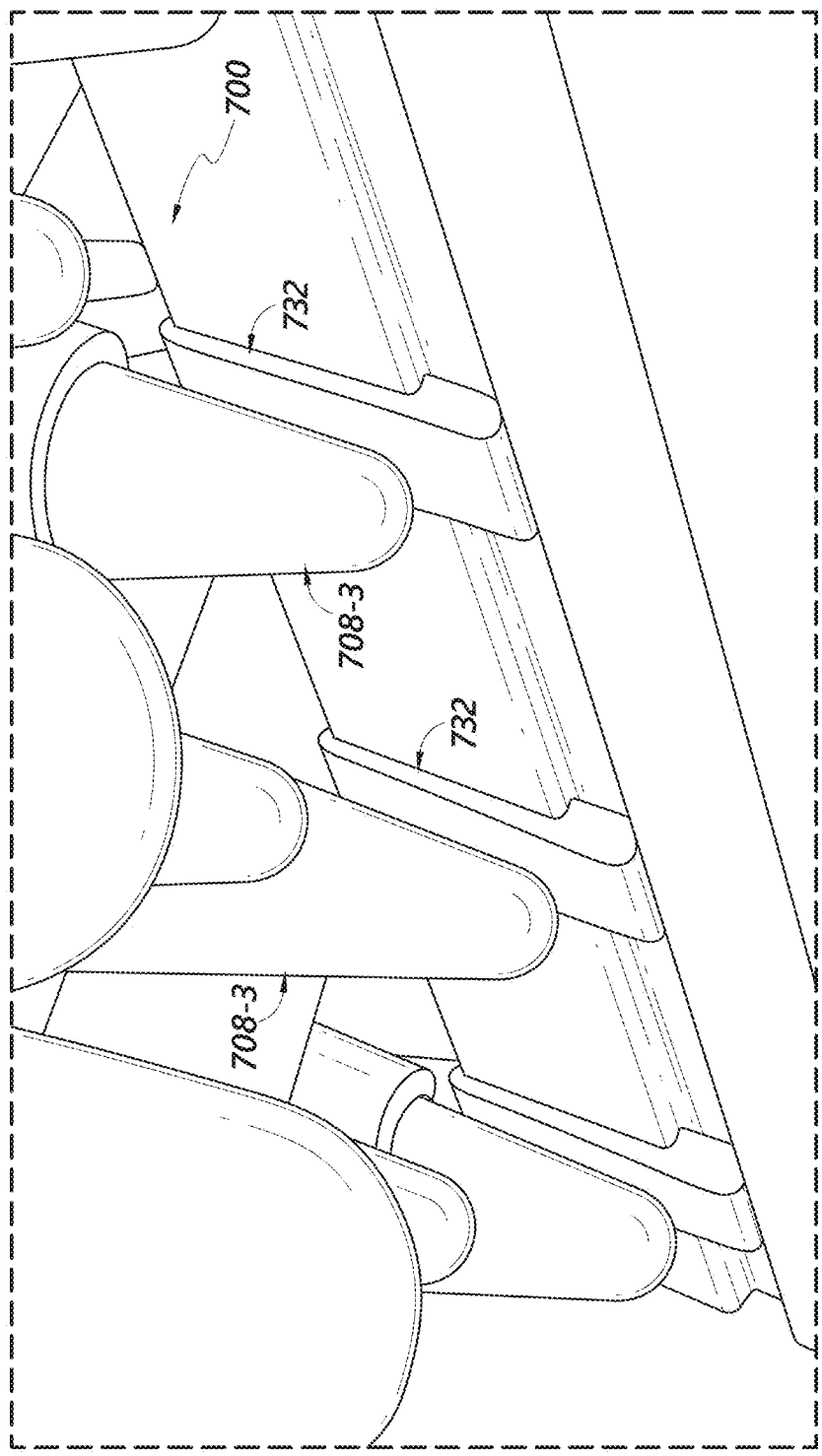
Figure 7C:
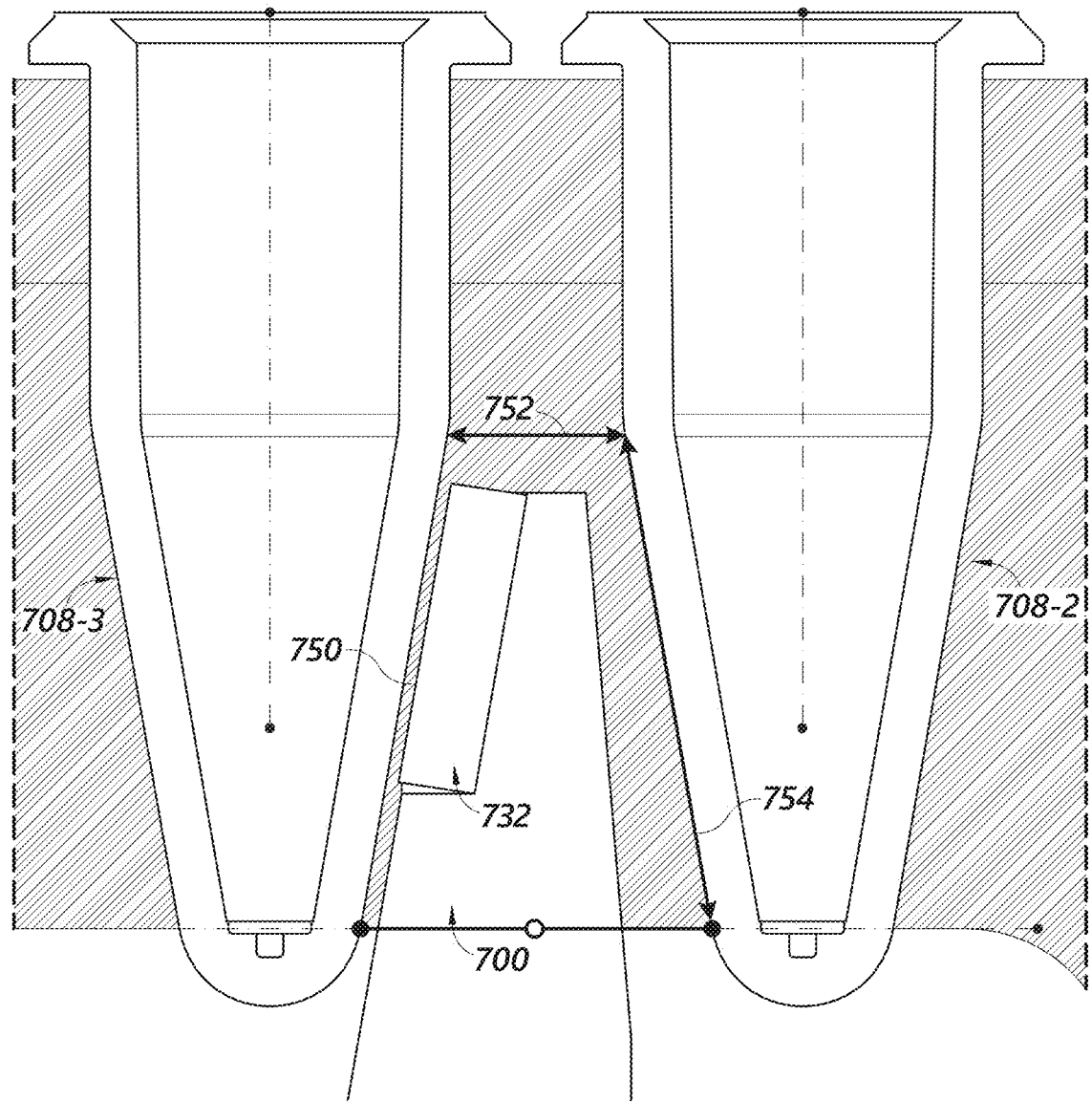
FIG. 7C illustrates a side profile view of the dimensions of an embodiment of a fixed magnet assembly that is positioned between certain components of a reagent holder, in accordance with embodiments disclosed herein.

FIGS. 7A and 7B illustrate two perspective views of an embodiment of a fixed magnet assembly according to the disclosed technology that can be implemented into an automated diagnostic or preparatory apparatus. FIG. 7C illustrates a side profile view of the dimensions of the fixed magnet assembly 700 in FIGS. 7A-7B relative to the dimensions of the snap-in containers of reagent holders received in a diagnostic or preparatory apparatus.

In particular, the magnets 732 of a fixed magnet assembly 700 are shown to be positioned in close proximity with the third snap-in containers 708-3 (e.g., third snap-in container, such as container 608-3 in FIGS. 6A-6E) of reagent holders received in a diagnostic or preparatory apparatus. In this non-limiting example, for each reagent holder, a magnet 732 is positioned behind the third snap-in container 708-3 (e.g., between the third snap-in container 708-3 and where the second snap-in container would reside, if shown). Furthermore, in this embodiment of the fixed magnet assembly 700, the magnets 732 are oriented at an angle that makes them parallel to the sloped wall of the snap-in containers 708-3 (e.g., resulting in magnetic forces that are normal to the sloped wall).

As shown in FIG. 7A, the fixed magnet assembly 700 (and its magnets 732) may be configured to fit in between the second snap-in container (not shown) and the third snap-in container (e.g., between containers 608-3 and 608-2 in FIG. 6E) once the fixed magnet assembly 700 is installed and a rack with loaded reagent holders is received in the receiving bay of the diagnostic or preparatory apparatus. The fixed magnet assembly 700 may be configured to fit in the very small volume between the snap-in containers, despite variations in dimensions across diagnostic or preparatory apparatus and the differences in the exact placement of each fixed magnet assembly 700 within the receiving bays of diagnostic or preparatory apparatuses. In one non-limiting example, the fixed magnet assembly 700 can be positioned so that the magnets are as little as 0.01 inches distance away from the sloped wall of the containers, and the fixed magnet assembly 700 may have dimensions that enable it to be positioned in the space between containers. For instance, the fixed magnet assembly 700 may have a width that ranges from between 0.15-0.3 inches and a height below 0.4 inches. The ability to fit the fixed magnet assembly 700 into such a small volume may advantageously allow for existing diagnostic or preparatory apparatuses to be retrofitted with the fixed magnet assembly 700 without having to re-design reagent holders or the snap-in containers, while also enabling the magnets 732 of the fixed magnet assembly 700 to effectively and consistently apply a magnetic force to the snap-in containers 708-3.

This advantageous aspect of the fixed magnet assembly 700 is better visualized in FIG. 7C, which shows a side profile of the fixed magnet assembly 700 positioned between the third snap-in container 708-3 and second snap container 708-2. In some embodiments, the distance 750 between the sloped wall of the third snap-in container 708-3 and a magnet 732 of the fixed magnet assembly 700 may be 0.011 inches or less, the horizontal distance 752 between the walls of the third snap-in container 708-3 and the second snap-in container 708-2 of a reagent strip may be 0.152 inches or less, and the length 754 of the sloped wall of one of the snap-in containers may be approximately 0.407 inches. The fixed magnet assembly 700 may be sized and shaped to fit within this space between the third snap-in container 708-3 and second snap-in container 708-2 of a reagent strip when the reagent strip is loaded into a rack received in the receiving bay of the diagnostic or preparatory apparatus.

Although the example fixed magnet assemblies 700 in FIGS. 7A and 7B are shown to be configured to exert a magnetic force on the third snap-in container, it will be understood that they can be suitably positioned to exert a magnetic force on any other snap-in container, depending on the particular assay or process that is implemented and which container is likely to include carryover particles.

It should be noted that the magnets 732 of the embodiment of the fixed magnet assembly 700 shown in FIGS. 7A and 7B can be thought of as arranged along a single linear axis (e.g., an axis that is perpendicular to the longitudinal axis of the reagent holders, as well as perpendicular to a processing axis of the reagent holders). Thus, despite the magnets 732 of the fixed magnet assembly 700 being arranged in a different manner than the magnets 632 shown in FIG. 6B, the second magnet axis 614 shown in FIGS. 6A and 6B would still be applicable if adjusted to run between the second and third snap-in containers (the magnets 732 would reside on that axis, similarly to the magnets 622 on the first magnet axis 612, and exert a magnetic force on the third snap-in containers that would be best represented as a vertical vector in FIG. 6B).

Figure 8A:
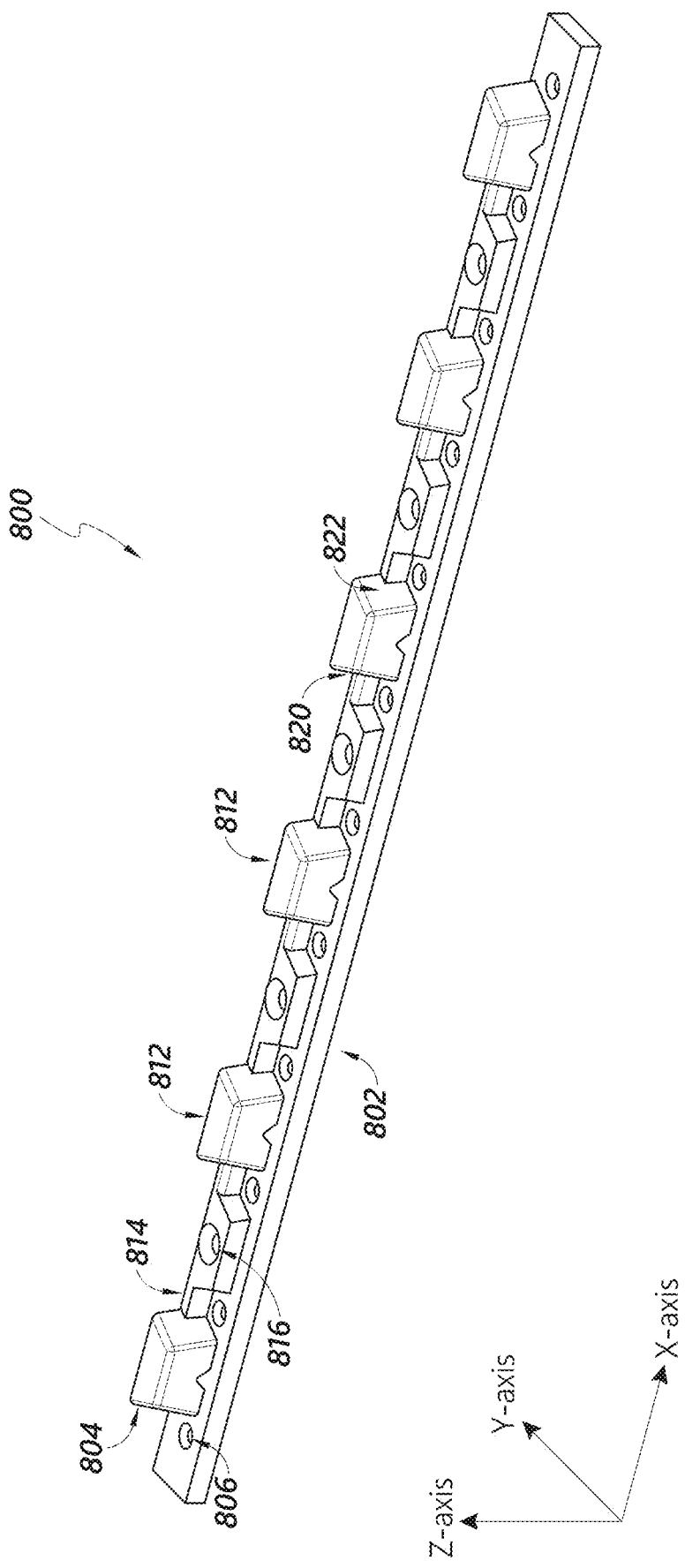
FIG. 8A illustrates an isometric view of an embodiment of a fixed magnet assembly that can be implemented into an automated diagnostic or preparatory apparatus, in accordance with embodiments disclosed herein.
Figure 8B:
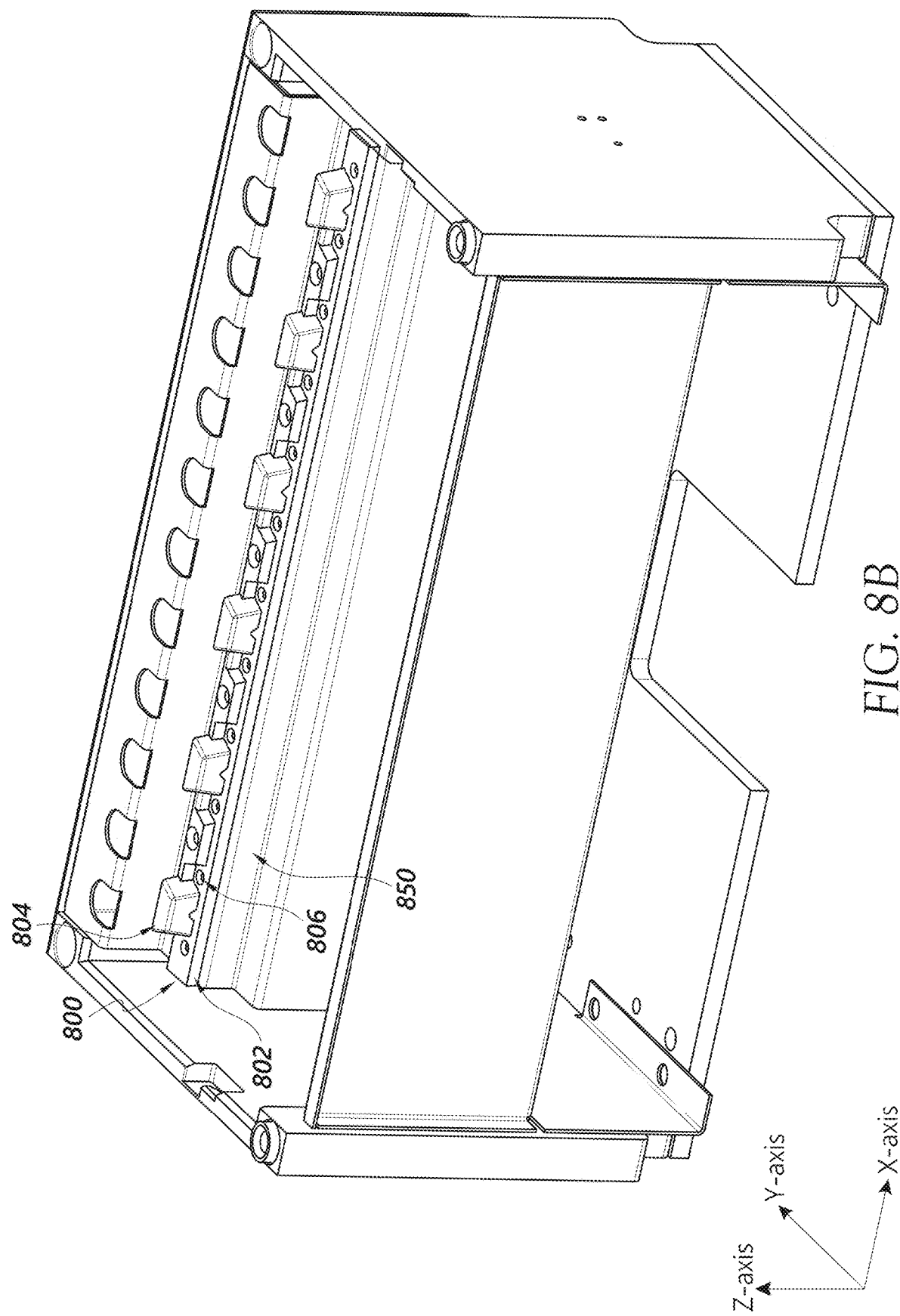
FIG. 8B illustrates an isometric view of an embodiment of a fixed magnet assembly affixed to a cover of an automated diagnostic or preparatory apparatus, in accordance with embodiments disclosed herein.

FIG. 8A illustrates an isometric view of an embodiment of a fixed magnet assembly that can be implemented according to the disclosed technology into an automated diagnostic or preparatory apparatus. More specifically, FIG. 8A shows an embodiment of a fixed magnet assembly 800 having fixed height when implemented into the diagnostic or preparatory apparatus. FIG. 8B illustrates the fixed magnet assembly of FIG. 8A implemented in a receiving bay of a diagnostic or preparatory apparatus, such as within the receiving bay 500 described with reference to FIGS. 5A-5B.

The fixed magnet assembly 800 may include a support plate 802, which may have dimensions suited to the particular diagnostic or preparatory apparatus in which the fixed magnet assembly 800 is implemented. In some embodiments, the support plate 802 may be a machined aluminum plate. The support plate 802 may include a set of recesses or holes 806, each of which is configured to receive the bottom end of a container (e.g., mixing tube), such as container 708-3 shown in FIGS. 7A-7B or container 608-3 shown in FIGS. 6A-6E. For instance, the indicated positions of the containers 608-3 shown in the conceptual view of FIG. 6B may coincide with the positions of the holes 806 on the support plate 802.

The fixed magnet assembly 800 may also include a magnet holder 804, which may similarly have dimensions suited to the particular diagnostic or preparatory apparatus in which the fixed magnet assembly 800 is implemented. In some embodiments, the magnet holder 804 may be made of a material that is chemically resistant to cleaning agents. The magnet holder 804 may include a set of magnet housings 812 and connectors 814. The magnet housings 812 and the connectors 814 can be integrally formed as a single, monolithic piece. In another example, the magnet housings 812 and the connectors 814 are coupled to form the magnet holder 804. Other configurations can be suitably implemented. In some embodiments, each magnet housing 812 may have a trapezoidal shape when viewed from top-down. In this example, each magnet housing 812 houses two magnets (not shown) that are located adjacent to a first face 820 and a second face 822 of the magnet housing 812, respectively. This arrangement may be similar to how FIG. 6B shows the pair of magnets 632 are arranged within the housing 630.

In one non-limiting example, the fixed magnet assembly 800 is a single, monolithic piece that includes a plurality of magnet housings 812 separated by connectors 814. In some cases, the fixed magnetic assembly is a unitary structure that includes a plurality of magnet housings 812. A unitary fixed magnet assembly 800 can be formed, for example, of a magnetic material. In another non-limiting example, a unitary fixed magnet assembly 800 is formed of one or more non-magnetic materials, and a magnetic material is coupled to interior walls of the housing adjacent to the first face 820 and the second face 822 of each magnet housing 812. Other configurations are possible.

The magnet holder 804 may have mounting holes 816 (e.g., in the connectors 814) for attaching the magnet holder 804 to the support plate 802. For instance, fasteners (e.g., screws) can be inserted into the mounting holes 816 to affix the magnet holder 804 to the support plate 802 and form the fixed magnet assembly 800. The support plate 802 of the fixed magnet assembly 800 can then be installed in (for example, affixed to) the diagnostic or preparatory apparatus using any suitable mechanism. In some embodiments, the fixed height (e.g., the up/down position) of the magnet holder 804 relative to the support plate 802 and the rest of the diagnostic or preparatory apparatus may be adjusted by adding a shim of a desired height measured in the z-direction between the magnet holder 804 and the supporting plate 802. Installation of the fixed magnet assembly 800 can include selecting one of a plurality of shims of different heights from an installation kit, installing the selected shim in a receiving bay, and installing the fixed magnet assembly 800 over the shim in the z-direction. This can be particularly advantageous when a fixed magnet assembly is retrofitted into existing preparatory and diagnostic apparatuses in the field, in view of very slight differences in the dimensions and tight tolerances associated with receiving bays and racks implemented in the apparatuses.

Thus, the mixing tubes (e.g., container 608-3 or container 708-3) of the reagent holders may be received in the holes 806 of the support plate 802, resulting in each mixing tube being in close proximity with a magnet in an adjacent magnet housing 812 (e.g., a magnet located behind either a first face 820 or second face 822 of the adjacent magnet housing 812). In some embodiments, the first face 820 and the second face 822 of each magnet housing 812 may be oriented at an angle that makes them parallel to the sloped wall of the mixing tubes (e.g., container 608-3 or container 708-3) when the mixing tubes are disposed in the holes 806. Thus, the magnet located behind each first face 820 or second face 822 of the magnet housings 812 may also be oriented so as to be parallel to the sloped wall of the adjacent mixing tube, resulting in magnetic forces that are normal to the sloped wall of the mixing tube.

The shape and dimensions of the magnet housings 812 and the shape and dimensions of the connectors 814 that connect the magnet housings 812 can be advantageously tailored, such that they do not interfere with a skirt or flange of the receptacles of the reagent holder (e.g., receptacles 250) that receive the second snap-in container or the third snap-in container (e.g., containers 608-2 and 608-3, respectively), when the fixed magnet assembly 800 is installed in the diagnostic or preparatory apparatus and a rack containing the reagent holder is loaded into a receiving bay of the diagnostic or preparatory apparatus. For example, the connectors 814 may have a selected depth (measured in the y-direction) and height (measured in the z-direction) in the portions near the holes 806, such that the connectors 814 fit between the very small space between the second snap-in container and the third snap-in container of a reagent holder housed in a rack inserted into the receiving bay. This allows a magnetic force to be applied by the magnet housings 812 to the third snap-in container without physically interfering with the second snap-in container, which would otherwise be pushed through its receptacle and out the top of the reagent holder when the rack housing the reagent holder is inserted in the receiving bay if the dimensions of the magnet housings 812 and connectors 814 were not configured properly.

As in the illustrated embodiment, the fixed magnet assembly 800 can advantageously include magnet housings 812 that are configured to apply a magnetic force to the snap-in containers of two different reagent holders simultaneously (e.g., as with the magnet housing 630 in FIG. 6B). More specifically, a magnet housing 812 of the fixed magnet assembly 800 may include two magnets (not shown), one of which may apply a magnetic force to one side of a snap-in container of a reagent holder, and the other of which may apply a magnetic force to an opposing side of another snap-in container of a different reagent holder. In other words, the magnets in a magnet housing 812 may apply magnetic force to opposite sides of the snap-in tubes of adjacent reagent holders; adjacent magnets in the fixed magnet assembly 800 apply magnetic force to opposite sides of snap-in tubes of adjacent reagent holders. Although magnetic force is applied to different sides of snap-in containers depending on which magnet is in close proximity to the snap-in containers (as shown in FIG. 6B), the problem of magnetic extraction particle carry-over is effectively and consistently addressed for each of the reagent holders. This implementation may avoid having to place the magnets in a very tight space (e.g., between the third snap-in container and the second snap-in container of a reagent holder, as in the example of FIGS. 7A-7B). Instead, the magnets can be arranged at an oblique angle relative to the processing axis of each reagent holder, rather than being arranged on the processing axis. An example of this is shown by the arrangement of each pair of magnets 632 in the magnet housings 630 shown in FIG. 6B.

In some embodiments, the fixed magnet assembly 800 may be implemented in a particular diagnostic or preparatory apparatus by affixing the support plate 802 to a cover 850 of the apparatus using a fastener, such as using very high bond tape. This approach may allow the fixed magnet assembly 800 to be inexpensively and quickly implemented into a particular apparatus on-site (e.g., at the location of the diagnostic or preparatory apparatus), but there may be unknown component variation among different apparatuses and also variation among all the potential personnel installing the fixed magnet assembly 800 into different apparatuses. FIG. 8B illustrates the same fixed magnet assembly 800 shown in FIG. 8A (including the support plate 802 and the magnet holder 804) affixed to the cover 850 of a diagnostic or preparatory apparatus.

More specifically, FIG. 8B shows how the fixed magnet assembly 800 can be implemented within a receiving bay of a diagnostic or preparatory apparatus, such as the receiving bay 500 of the diagnostic or preparatory apparatus shown in FIGS. 5A-5B, so that when the receiving bay receives a rack with reagent holders inserted into the rack, the process tubes of those reagent holders are received in the holes 806 of the support plate 802 of the fixed magnet assembly 800. Furthermore, the one or more movable magnets of a magnetic separator (not shown in this figure, but described above with reference to FIGS. 3A-3C) can apply a magnetic force to each process tube of the reagent holders in the rack. In addition, with the fixed magnet assembly 800 installed in this position, a constant, consistent magnetic force from the magnets of the fixed magnet assembly 800 (e.g., the magnets in the magnet housings 812) is also applied to each third snap-in container of the reagent holders in the rack.

Figure 9:
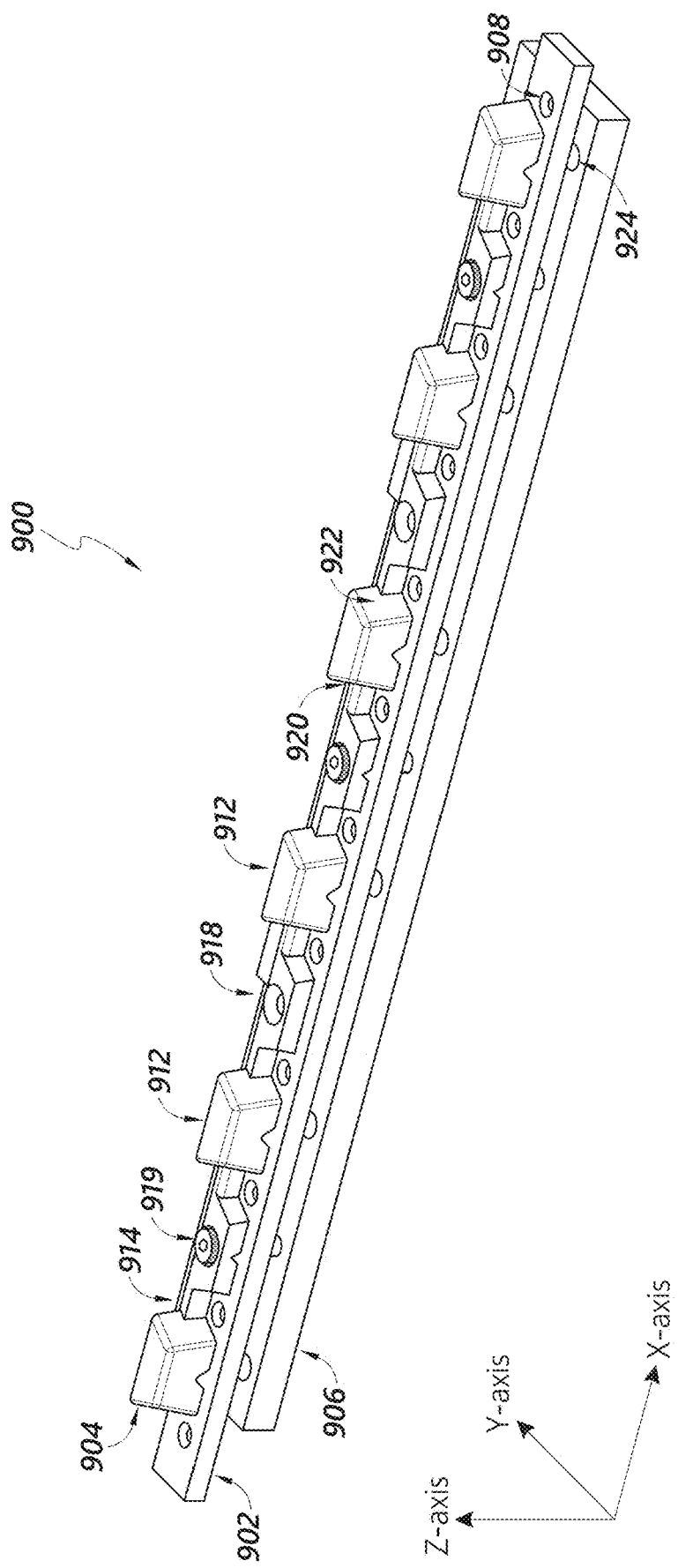
FIG. 9 illustrates an isometric view of an embodiment of a fixed magnet assembly that can be implemented into an automated diagnostic or preparatory apparatus, in accordance with embodiments disclosed herein.

FIG. 9 illustrates an isometric view of an embodiment of a fixed magnet assembly according to the disclosed technology that can be implemented into an automated diagnostic or preparatory apparatus. More specifically, FIG. 9 shows an embodiment of a fixed magnet assembly 900 that is compliant in the z-direction (e.g., can move upward or downward in the z-direction when implemented in in the receiving bay of the diagnostic or preparatory apparatus).

The fixed magnet assembly 900 may include a support plate 902, which may have dimensions suited to the particular diagnostic or preparatory apparatus in which the fixed magnet assembly 900 is implemented. In some embodiments, the support plate 902 may be a machined aluminum plate. The support plate 902 may include a set of recesses or holes 908, each of which is configured to receive the bottom end of a container (e.g., mixing tube), such as container 708-3 shown in FIGS. 7A-7B or container 608-3 shown in FIGS. 6A-6E. For instance, the indicated positions of the containers 608-3 shown in the conceptual view of FIG. 6B may coincide with the positions of holes 908 on the support plate 902.

The fixed magnet assembly 900 may also include a magnet holder 904, which may similarly have dimensions suited to the particular diagnostic or preparatory apparatus in which the fixed magnet assembly 900 is implemented. In some embodiments, the magnet holder 904 may be made of a material that is chemically resistant to cleaning agents. The magnet holder 904 may include a set of magnet housings 912 and connectors 914. In some embodiments, each magnet housing 912 may have a trapezoidal shape when viewed from top-down. In this example, each magnet housing 912 houses two magnets (not shown) that are located adjacent to a first face 920 and a second face 922 of the magnet housing 912, respectively. This arrangement may be similar to how FIG. 6B shows the pair of magnets 632 are arranged within the housing 630.

The fixed magnet assembly 900 includes a mounting plate 906 positioned below the support plate 902. The fixed magnet assembly includes a set of springs 924 (not visible in this view), with one end of each spring attached to the mounting plate 906 and an opposite end of each spring attached to the magnet holder 904 and/or the support plate 902. Other biasing mechanisms, in addition to or as an alternative to springs 924, can be suitable implemented. The springs 924 exert a biasing force against the support plate 902 in order to create a desired spacing between the mounting plate 906 and the support plate 902 when the springs are in an uncompressed state. To assemble the fixed magnet assembly 900 of this non-limiting embodiment, the magnet holder 904 is affixed to the support plate 902. In some embodiments, the magnet holder 904 can be mechanically coupled to the support plate 902 using fasteners 919, which may be received in mounting holes 918 of the magnet holder 904 and corresponding mounting holes of the support plate 902 (not shown). Next, the support plate 902 is affixed to the mounting plate 906. The support plate 902 can be affixed using springs 924 that are coupled to the support plate 902 and the mounting plate 906, which allow the support plate 902 to move up and down in the z-axis (e.g. by compressing or uncompressing the springs 924) relative to the mounting plate 906. In some embodiments, the support plate 902 may additionally be mechanically coupled to the mounting plate 906 via fasteners 919. The fasteners 919 may be inserted through mounting holes in the magnet holder 904 (e.g., mounting holes 918) and corresponding mounting holes of the support plate 902 (not shown) to affix the support plate 902 to the mounting plate 906. In some embodiments, the fasteners 919 may be screws or shoulder bolts, and they may limit the maximum spacing between the mounting plate 906 and the support plate 902. The fasteners 919 may place an upward limit to the upward movement of the support plate 902 in the z-direction away from the mounting plate 906, but do not limit downward movement of the support plate 902 in the z-direction toward the mounting plate 906. In some embodiments, the fasteners 919 may additionally restrict the movement of the support plate 902 in the x-axis and y-axis. The fixed magnet assembly 900 can then be affixed to the receiving bay of a diagnostic or preparatory apparatus, such as by affixing the mounting plate 906 to the cover of the diagnostic and preparatory apparatus using a fastener, such as a very high bond tape or fasteners received in the mounting plate 906. Other fasteners can be suitably implemented in accordance with the disclosed technology.

Advantageously, the support plate 902 of the installed fixed magnet assembly 900 can move upward or downward in the z-direction in the receiving bay before and during insertion of a rack in the receiving bay, because the springs 924 allow movement of the support plate 902 in the z-direction relative to the mounting plate 906 fixed to the cover. This feature may allow for the mixing tubes (e.g., container 608-3 or container 708-3) of the reagent holders to be properly positioned relative to the magnets in the magnet holder 904 without requiring that exact magnet positioning (e.g., via designing, building, and positioning the fixed magnet assembly with very tight tolerances) be accurately and consistently reproduced across each of a plurality of apparatuses in which a fixed magnet assembly is installed. For example, as a rack is inserted into the receiving bay, a bottom surface of the rack can contact a top surface of the magnet holder 904. In one non-limiting example, this contact takes place between a bottom surface of the rack and a top surface of one or more magnet housings 912. This contact can cause the magnet holder 904 and the support plate 902 to lower in the z-direction, thereby compressing the springs 924 located between the support plate 902 and the mounting plate 906. As the rack continues to be inserted into the receiving bay, the magnet holder 904 and the support plate 902 continue to lower in the z-direction until they reach a position that precisely positions the magnet housings 912 relative to the mixing tubes of the reagent holders, as well as precisely positions the mixing tubes of the reagent holders in the holes 908 of the support plate 902. In one non-limiting embodiment, as the springs 924 are compressed, the support plate 902 lowers relative to the mounting plate 906 until it reaches a point where the rack has reached its lowermost position within the receiving bay, at which point the bottom portions of the mixing tubes of the reagent holders will be reliably and accurately disposed in the holes 908 of the support plate 902. This arrangement results in each mixing tube being in close proximity with a magnet in an adjacent magnet housing 912 (e.g., behind either a first face 920 or second face 922 of the adjacent magnet housing 912), independent of specific dimensional variations in the rack that is used to insert the holders into the receiving bay and independent of specific dimensional variations in the receiving bay that receives the holders. Accordingly, this arrangement for providing magnetic energy to the mixing tube of a plurality of holders using a support plate 902 that is adjustable in the z-direction can be reliably and accurately reproduced across many different apparatuses, independent of variations in the dimensions and tolerances between the receiving bay and the rack of the apparatus.

In some embodiments, the first face 920 and the second face 922 of each magnet housing 912 may be oriented at an angle that makes them parallel to the sloped wall of the mixing tubes (e.g., container 608-3 or container 708-3) when the mixing tubes are disposed in the holes 908. Thus, the magnet located adjacent to each first face 920 or second face 922 inside the magnet housings 812 may also be oriented so as to be parallel to the sloped wall of the adjacent mixing tube, resulting in magnetic forces that are normal to the sloped wall of the mixing tube.

Advantageously, embodiments of the fixed magnet assembly 900 according to the disclosed technology can allow the fixed magnet assembly 900 to be implemented into a particular diagnostic and preparatory apparatus on-site (e.g., at the location of the diagnostic and preparatory apparatus) using nominal magnet positioning.

Figure 10A:
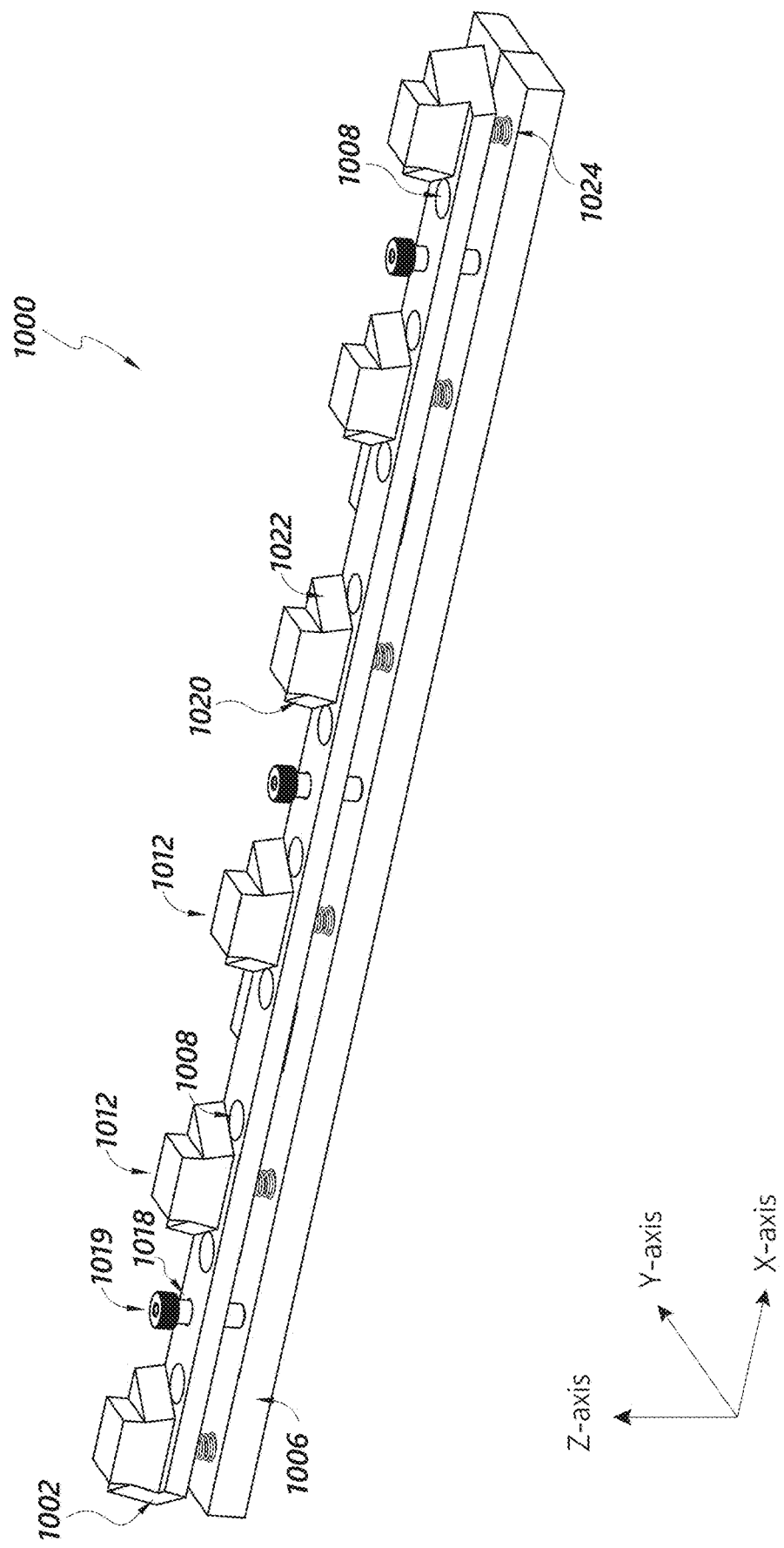
FIG. 10A illustrates an isometric view of an embodiment of a fixed magnet assembly that can be implemented into a diagnostic and preparatory apparatus, in accordance with embodiments disclosed herein.
Figure 10B:
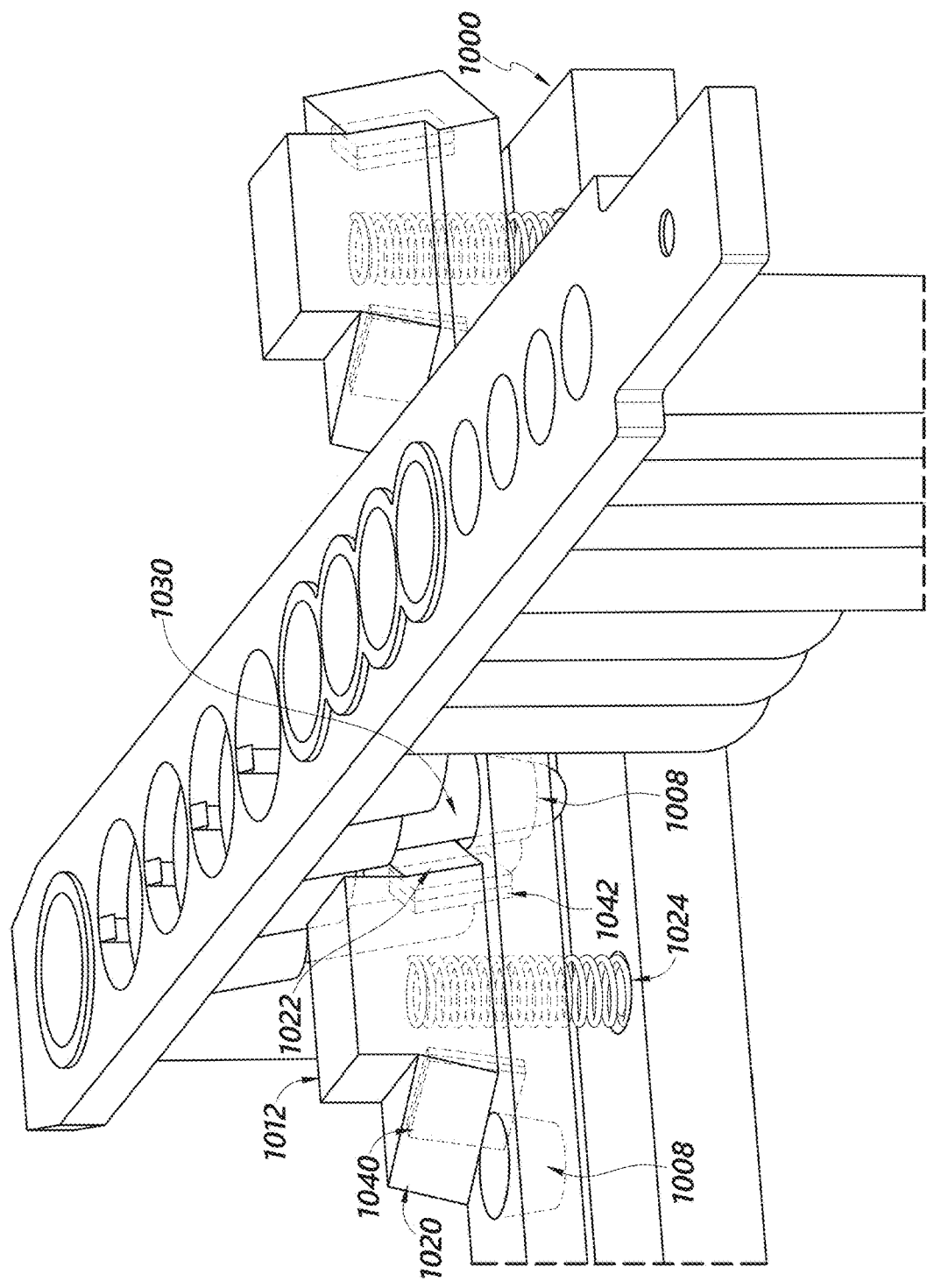
FIG. 10B illustrates a transparent perspective view of a reagent holder interacting with an embodiment of fixed magnet assembly, in accordance with embodiments disclosed herein.

FIG. 10A illustrates an isometric view of an embodiment of a fixed magnet assembly that can be implemented accordingly to the disclosed technology into an automated diagnostic or preparatory apparatus. More specifically, FIG. 10A shows an embodiment of a fixed magnet assembly 1000 that is compliant in the z-direction (e.g., can move upward or downward in the z-direction when implemented in the receiving bay of the diagnostic or preparatory apparatus). FIG. 10B illustrates a transparent perspective view of a reagent holder interacting with the fixed magnet assembly 1000 of FIG. 10A, in order to demonstrate how a third snap-in container 1030 of the reagent holder may be seated in a hole 1008 of the support plate 1002 of the fixed magnet assembly 1000, once the fixed magnet assembly 1000 is installed and a rack containing the reagent holder is loaded into the receiving bay of the diagnostic or preparatory apparatus.

The fixed magnet assembly 1000 may include a support plate 1002, which may have dimensions suited to the particular diagnostic or preparatory apparatus in which the fixed magnet assembly 1000 is implemented. In some embodiments, the support plate 1002 may be a machined aluminum plate. The support plate 1002 may include a set of recesses or holes 1008, each of which is configured to receive the bottom end of a container (e.g., mixing tube), such as container 708-3 shown in FIGS. 7A-7B or container 608-3 shown in FIGS. 6A-6E. For instance, the indicated positions of the containers 608-3 shown in the conceptual view of FIG. 6B may coincide with the position of holes 1008 on the support plate 1002.

The fixed magnet assembly 1000 may also include a set of magnet housings 1012. In some embodiments, the magnet housings 1012 may be made of a material that is chemically resistant to cleaning agents. The magnet housings 1012 may have a trapezoidal shape when viewed from top-down. In this example, each magnet housing 1012 houses two magnets (not shown in FIG. 10A but visible in FIG. 10B) that are located adjacent to a first face 1020 and a second face 1022 of the magnet housing 1012, respectively. This arrangement may be similar to how FIG. 6B shows the pair of magnets 632 are arranged within the housing 630.

The fixed magnet assembly 1000 includes a mounting plate 1006 positioned below the support plate 1002. The fixed magnet assembly 1000 includes a set of springs 1024 with one end of each spring attached to the mounting plate 1006 and an opposite end of each spring attached to the magnet housings 1012 and/or the support plate 1002. Other biasing mechanisms, in addition to or as an alternative to springs 1024, can be suitably implemented. There may be spacing between the support plate 1002 and the mounting plate 1006 when the springs 1024 are in an uncompressed state.

The springs 1024 exert a biasing force against the support plate 1002 in order to create a desired spacing between the mounting plate 1006 and the support plate 1002 when the springs are in an uncompressed state. In some embodiments, the support plate 1002 may additionally be mechanically coupled to the mounting plate 1006 via fasteners 1019. The maximum spacing between the mounting plate 1006 and the support plate 1002 may be limited by fasteners 1019 (e.g., screws or shoulder bolts) inserted through mounting holes 1018 in the support plate 1002. These fasteners 1019 are inserted into the mounting holes 1018 to affix the support plate 1002 to the mounting plate 1006 to form the fixed magnet assembly 1000. In this example, the heads of the fasteners 1019 inserted in the mounting holes 1018 place an upward limit to the upward movement of the support plate 1002 in the z-direction away from the mounting plate 1006, but do not limit downward movement of the support plate 1002 in the z-direction toward the mounting plate 1006. In some embodiments, the fasteners 1019 may additionally restrict the movement of the support plate 1002 in the x-axis and y-axis. The fixed magnet assembly 1000 can then be affixed to the diagnostic or preparatory apparatus, such as by affixing the mounting plate 1006 to the cover of the diagnostic and preparatory apparatus using a fastener, such as a very high bond tape or other suitable fastener.

Advantageously, the spring-mounted support plate 1002 of the installed fixed magnet assembly 1000 can move upward or downward in the z-direction in the receiving bay before and during insertion of a rack in the receiving bay, because the springs 1024 allow movement of the support plate 1002 in the z-direction relative to the mounting plate 1006 fixed to the cover. This feature may allow for the mixing tubes (e.g., container 608-3 or container 708-3) of the reagent holders to be accurately and consistently positioned relative to the magnets in the magnet housings 1012 without requiring that exact magnet positioning be accurately and consistently reproduced across each of a plurality of apparatuses in which a fixed magnet assembly is installed. For example, the mixing tubes of the reagent holders may be received in the holes 1008 of the support plate 1002, and the mixing tubes (or another portion of the rack in contact with the complaint support plate 1002) may press down in the z-direction on the support plate 1002, compressing the springs 1024 located between the support plate 1002 and the mounting plate 1006. As the springs 1024 are compressed, the support plate 1002 lowers relative to the mounting plate 1006 until it reaches a point where the rack has reached its lowermost position within the receiving bay, at which point the bottom portions of the mixing tubes of the reagent holders will be reliably and accurately disposed in the holes 1008 of the support plate 1002. This arrangement results in each mixing tube being in close proximity with a magnet in an adjacent magnet housing 1012 (e.g., behind either a first face 1020 or second face 1022 of the adjacent magnet housing 1012), independent of specific dimensional variations in the rack that is used to insert the holders into the receiving bay and independent of specific dimensional variations in the receiving bay that receives the holders. Accordingly, this arrangement for providing magnetic energy to the mixing tube of a plurality of holders using a support plate 1002 that is adjustable in the z-direction can be reliably and accurately reproduced across many different apparatuses, independent of variations in the dimensions and tolerances between the receiving bay and the rack of the apparatus.

In some embodiments, the first face 1020 and the second face 1022 of each magnet housing 1012 may be oriented at an angle that makes them parallel to the sloped wall of the mixing tubes (e.g., container 608-3 or container 708-3) when the mixing tubes are disposed in the holes 1008. Thus, the magnet located adjacent to each first face 1020 or second face 1022 inside the magnet housings 1012 may also be oriented so as to be parallel to the sloped wall of the adjacent mixing tube, resulting in magnetic forces that are normal to the sloped wall of the mixing tube.

This can be more easily understood from FIG. 10B, which illustrates a transparent view of the fixed magnet assembly 1000 to more easily demonstrate features of the disclosed technology. Embodiments of the fixed magnet assembly, the mixing tube, and the holder need not be transparent. A mixing tube 1030 of a holder (e.g., a container in the third position from the process tube at the distal end of the holder) is shown seated in a hole 1008 of the fixed magnet assembly 1000. In this position, the mixing tube 1030 is positioned in close proximity to a magnet housing 1012 having a first face 1020 and a second face 1022. It can be seen from FIG. 10B that a magnet 1040 is positioned behind the first face 1020 and a magnet 1042 is positioned behind the second face 1022. The magnet 1042 is in close proximity to (within about 2 mm of) the mixing tube 1030 when the mixing tube 1030 is seated in the hole 1008 of the fixed magnet assembly 1000, and it can be seen that the magnet 1042 has a sloped orientation at an angle that matches the sloped wall of the mixing tube 1030.

Advantageously, the magnet housing 1012 is dimensioned such that it does not interfere with the second snap-in container (not shown, but analogous to container 608-2 shown in FIG. 6E) of the reagent holder. Furthermore, the magnet housing 1012 may also be advantageously dimensioned to not interfere with the skirt or flange of either the second or third receptacle that receives the second snap-in container or third snap-in container 1030, respectively.

Figure 11:
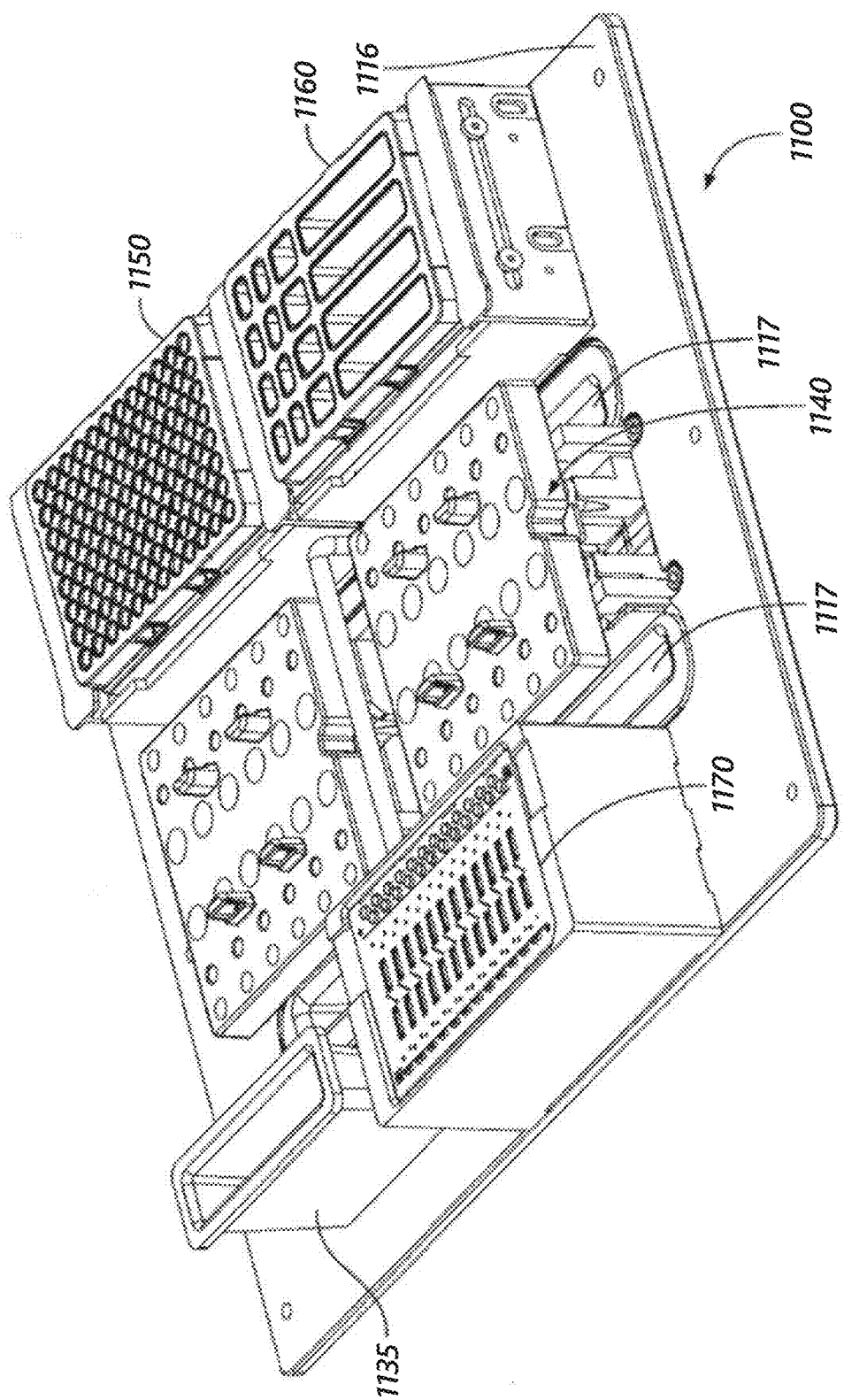
FIG. 11 illustrates an isometric view of the internals of some embodiments of an automated diagnostic or preparatory apparatus, in accordance with embodiments disclosed herein.

It will be understood that embodiments of the disclosed technology are not limited to applying a fixed magnetic force to a holder as described above with reference to FIGS. 2A-10B. Similarly, it will be understood that embodiments of the disclosed technology are not limited to applying a fixed magnetic force to a holder in an automated diagnostic or preparatory apparatus discussed above with reference to FIG. 1B. The disclosed technology can be advantageously implemented in any apparatus that receives a holder for processing and manipulating magnet substrates within a container of the holder. A non-limiting example automated apparatus configured to apply a fixed magnetic force to a non-limiting example holder in accordance with the disclosed technology will now be described with reference to FIGS. 11-15D to further illustrate certain advantageous features of the disclosed technology. FIG. 11 is an isometric view of the internals 1100 of some embodiments of a diagnostic or preparatory apparatus.

This illustrated embodiment of a diagnostic or preparatory apparatus may be similarly used to extract polynucleotides from samples and prepare them in PCR-ready form. This diagnostic or preparatory apparatus may be similar to the one disclosed in PCT Application No. WO2017/184244, filed on Feb. 17, 2017 (entitled "Automated Diagnostic Analyzer and Method for its Operation"), the disclosure of which is hereby incorporated here by reference in its entirety.

Notably, this embodiment of the diagnostic or preparatory apparatus may not use reagent holders containing pre-packaged reagents used in sample preparation, such as reagent holders in the form shown in FIGS. 2A-2C that are loaded into racks to be received by the diagnostic or preparatory apparatus. Instead, this diagnostic or preparatory apparatus may receive processing plates 1140 that do not include pre-packaged reagents, and the reagents for sample preparation may be stored separately at a different location on a processing deck 1116. The processing plates 1140 are described in more detail in connection to FIGS. 12A-12B.

For instance, there may be a dry reagent plate 1150 that includes a plurality of dry reagent compartments that are sealed by a penetrable membrane placed over each of the dry reagent compartments. In some embodiments, there may be 96 total dry reagent compartments in the dry reagent plate 1150, and each reagent compartment within the same plate 1150 is loaded with the same reagent so that the reagent plate is assay specific. However, multiple dry reagent plates 1150 can be used, depending on the assay or procedure, and separate reagent plates each with reagents specific to that assay can be utilized. For instance, to prepare a sample into PCR-ready form, there may be a first dry reagent plate (e.g., an extraction reagent plate) containing lysis buffer and magnetic particles (e.g., extraction beads) and a second dry reagent plate (e.g., an amplification reagent plate) containing master mix reagent. In other embodiments, different reagents can be combined on a single dry reagent plate 1150 (e.g., the extraction reagent plate and amplification reagent plate can be combined).

The apparatus may also include a liquid reagent plate 1160. The liquid reagent plate 1160 may include a plurality of reagent compartments organized in four processing rows, and each processing row may include four compartments where each compartment holds a reagent for a sample processing step. For example, each processing row may include a first compartment for a reconstitution buffer, a second compartment for a wash buffer, a third compartment for an elution buffer, and a fourth compartment for a neutralization buffer. These compartments can be arranged in the order in which they are used. However, they could be in other arrangements. In addition, each compartment holds enough reagent to process a full batch of samples, for example a batch of 24 total samples. A penetrable membrane (not shown) is placed over each of these compartments and is sealed to the liquid reagent plate 1160 so that if the membrane is penetrated to obtain access to one compartment, the remaining compartments remain sealed. This allows liquid reagent plate 1160 to be stored until needed for another batch of samples.

In some embodiments, the processing plates 1140 may have holes in which pipette tips may be parked, and there may be elongate openings 1117 on the processing deck 1116 that allows the reusable pipette tips parked in the processing plates 2040 to extend therethrough. In some embodiments, the processing deck 1116 may include a pipette tip chute 1135, in which used pipette tips may be disposed. In some embodiments, the internals 1100 of the diagnostic or preparatory apparatus may include a bay configured to receive an amplification cartridge 1170 that includes microfluidic channels and amplification chambers for performing amplification of a processed sample.

Figure 12A:
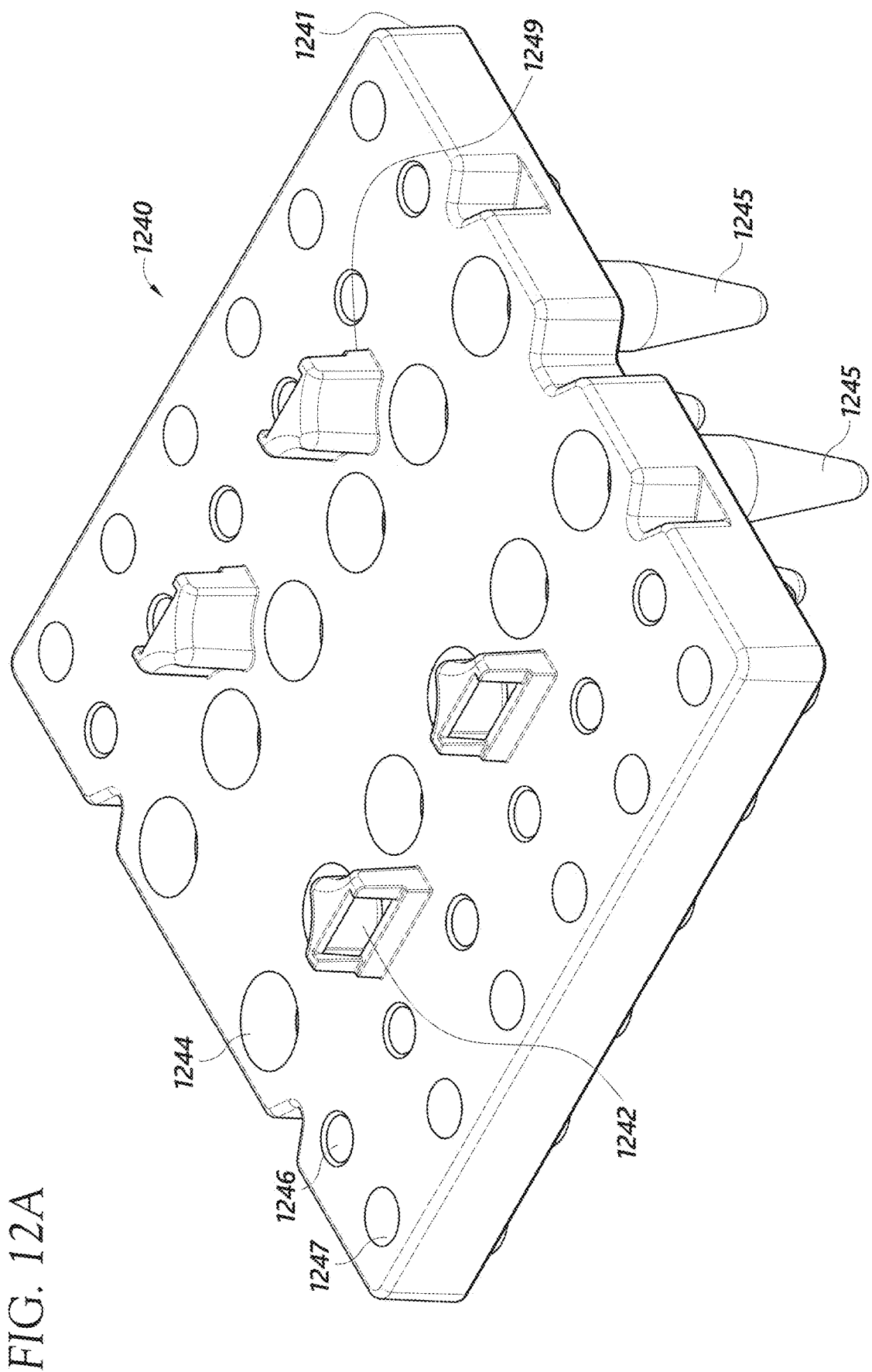
FIG. 12A illustrates an isometric view of a processing plate used in some embodiments of a diagnostic or preparatory apparatus, in accordance with embodiments disclosed herein.
Figure 12B:
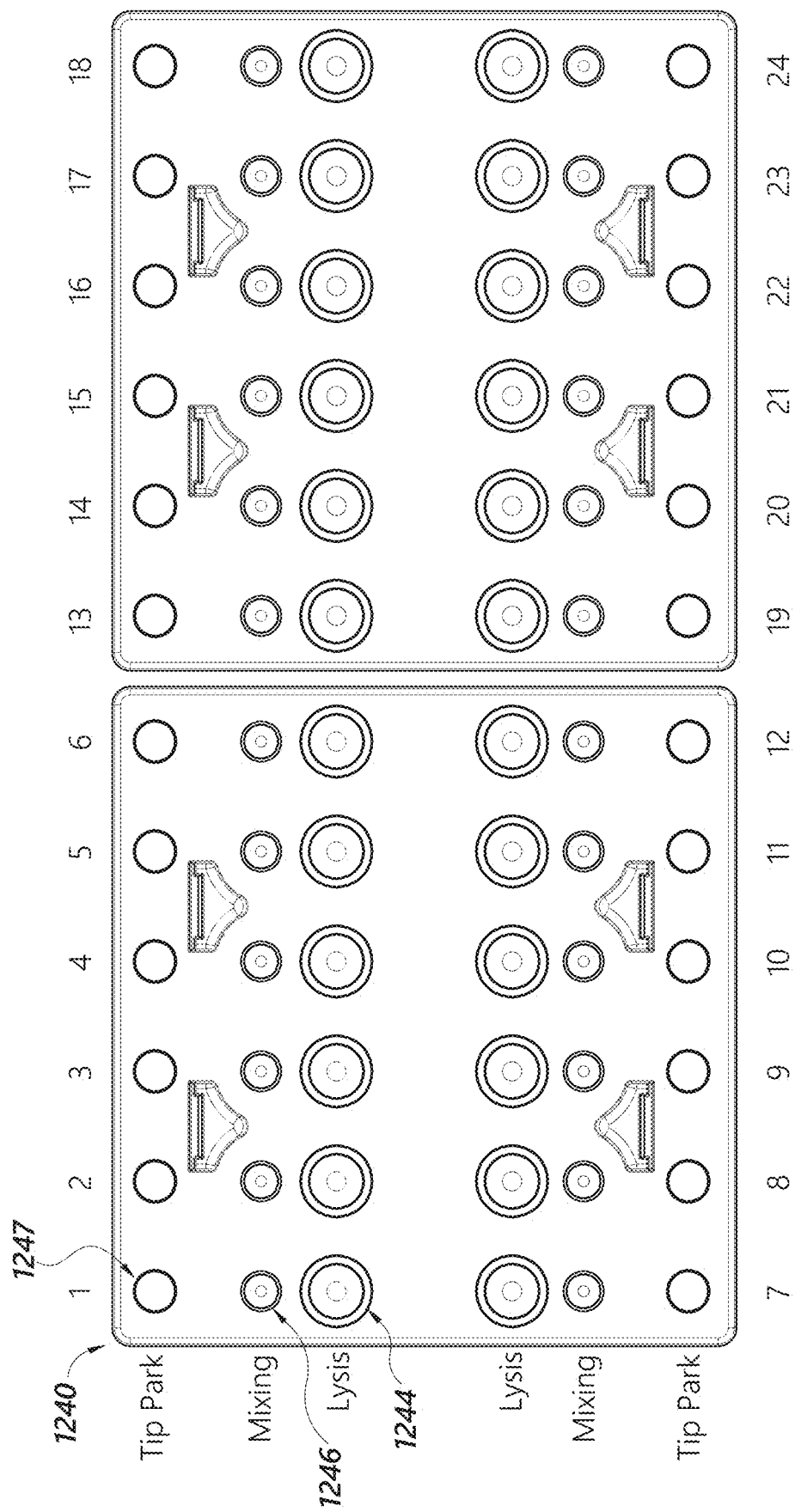
FIG. 12B illustrates a top-down view of an arrangement of two processing plates receiving in the receiving bay of some embodiments of a diagnostic or preparatory apparatus, in accordance with embodiments disclosed herein.

FIG. 12A is an isometric view of an example processing plate 1240 used in some embodiments of a diagnostic or preparatory apparatus describe with reference to FIG. 11. FIG. 12B is a top-down view of an arrangement of two processing plates 1240 when inserted for use into a receiving bay of some embodiments of the diagnostic or preparatory apparatus. This arrangement of the two processing plates 1240 may allow for 24 samples to be processes (12 from each processing plate 1240). FIGS. 12A and 12B are described together. The processing plate 1240 may the same or substantially similar to the processing plate 1140 described above with reference to FIG. 11. It will be understood that the disclosed technology is not limited to the specific features of the example processing plate 1240 and other suitably-configured processing plates can be implemented in the disclosed technology.

The processing plate 1240 may include a plate body 1241, which may partially define a plurality of process tubes 1244, mixing tubes 1246, and pipette tip holding stations 1247. The plate body 1241 may have a circular opening for each of the process tubes 1244, mixing tubes 1246, and pipette tip holding stations 1247. The process tubes 1244 may have a tube body 1245 that extends from the bottom of the plate body 1241, and the tube body 1245 may have a conical surface of revolution. The mixing tubes 1246 may also have a tube body (not shown, but visible in FIG. 13B) that extends from the bottom of the plate body 1241, which may also have a conical surface of revolution. The pipette tip holding stations 1247 may have a sleeve (not shown, but visible in FIG. 13B) that extends from the bottom of the plate body 1241. The sleeve may keep a pipette tip parked in the pipette tip holding station 1247 stable when disposed therein, even if the processing plate 1240 is moved.

In some embodiments, the process tubes 1244 may be alternatively referred to as extraction tubes or lysis tubes. In some embodiments, the mixing tubes 1246 may be alternatively referred to as mixing wells. The process tubes 1244 may be located closer to the middle of the plate body 1241 than the mixing tubes 1246, and the mixing tubes 1246 may be located closer to the middle of the plate body 1241 than the pipette tip holding stations 1247. Other configurations can be suitably implemented in the disclosed technology.

In some embodiments, the processing plate 1240 may include two rows of process tubes 1244, mixing tubes 1246, and pipette tip holders 1247 that are arranged parallel to each other. In the illustrated embodiment, the processing plate 1240 includes two rows of 6 process tubes 1244, two rows of 6 mixing tubes 1246, and two rows of 6 pipette tip holding stations 1247. However, more or less is contemplated (e.g., the processing plate 1240 can include two rows of 12 process tubes 1244, mixing tubes 1246 and pipette tip holding stations 1247 or even a single row of such). The processing of a single sample may involve one of the process tubes 1244 and its corresponding mixing tube 1246 and pipette tip holding station 1247 that are aligned with it in the same column. Thus, a single processing plate 1240 may allow 12 samples to be processed therein.

In some embodiments, the processing plate 1240 may include engagement members 1249 on the top surface of the processing plate 1240. The engagement members 1249 may include engagement notches 1242. The engagement members 1249 and the engagement notches 1242 may allow the processing plate 1240 to be grasped and moved by features (e.g., a robotic arm) of the diagnostic or preparatory apparatus for sample processing.

Figure 13A:
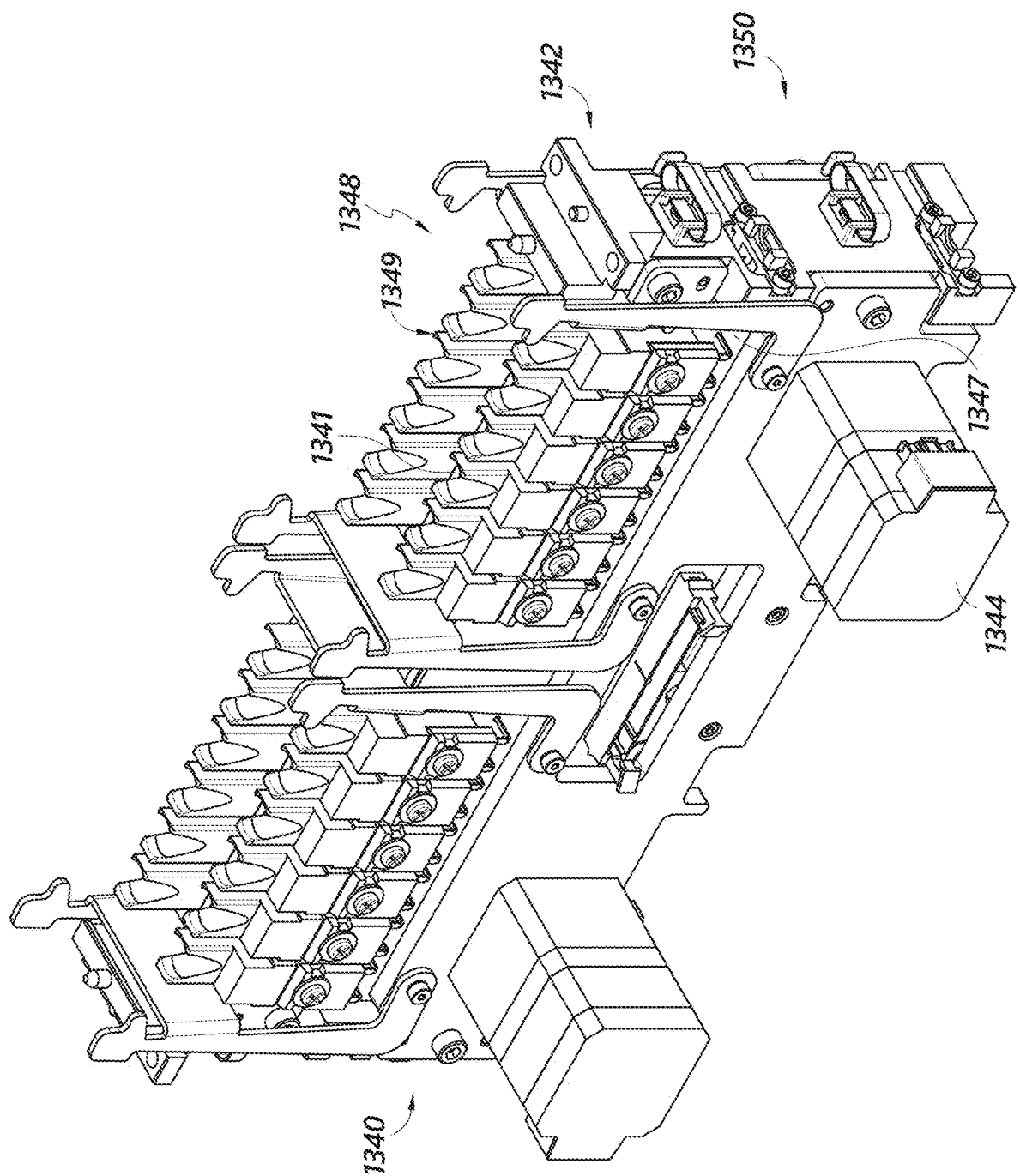
FIG. 13A illustrates an isometric view of the internals of some embodiments of a diagnostic or preparatory apparatus, in accordance with embodiments disclosed herein.
Figure 13B:
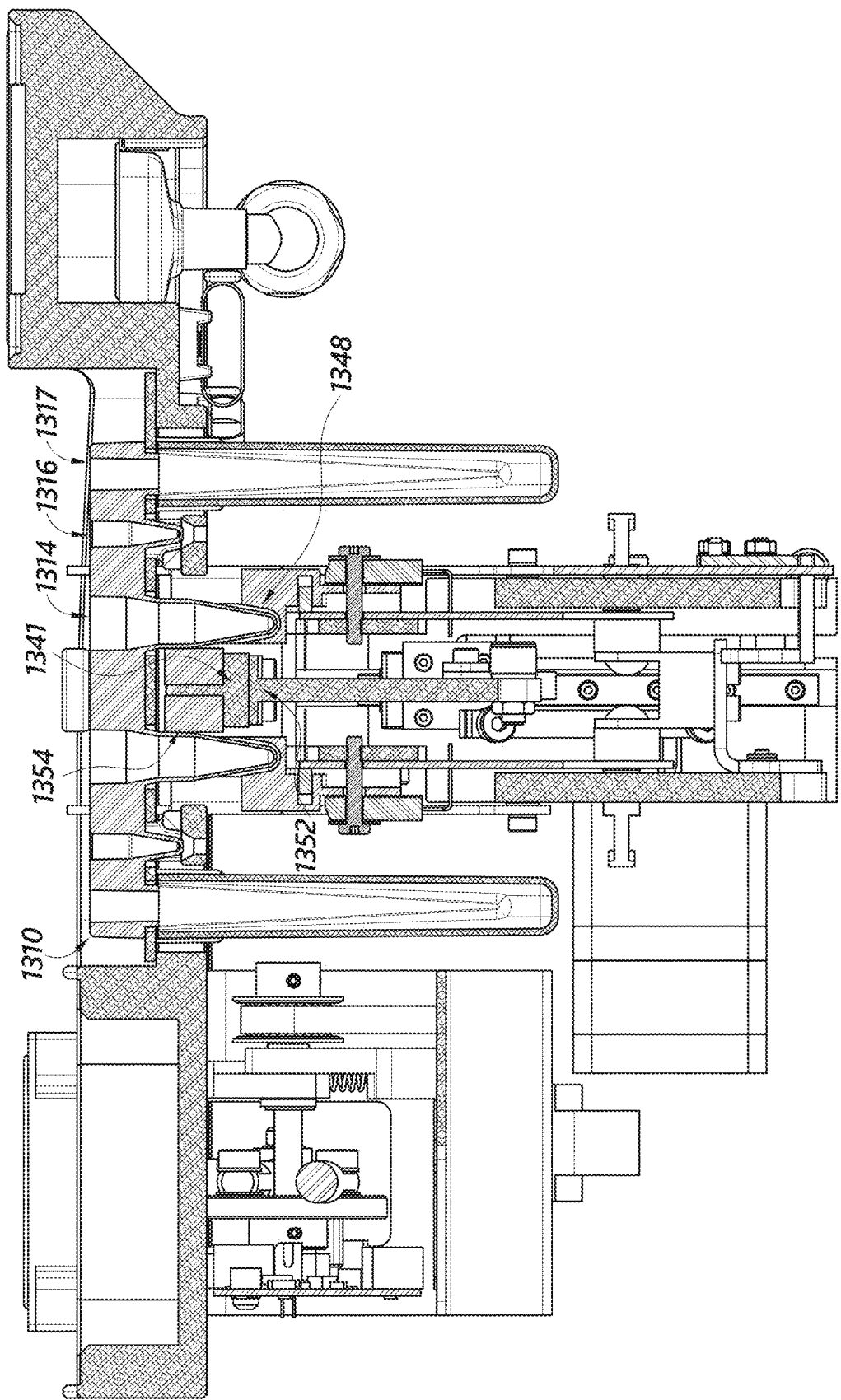
FIG. 13B illustrates a side profile view of a processing plate and the internals of some embodiments of a diagnostic or preparatory apparatus, in accordance with embodiments disclosed herein.
Figure 14A:
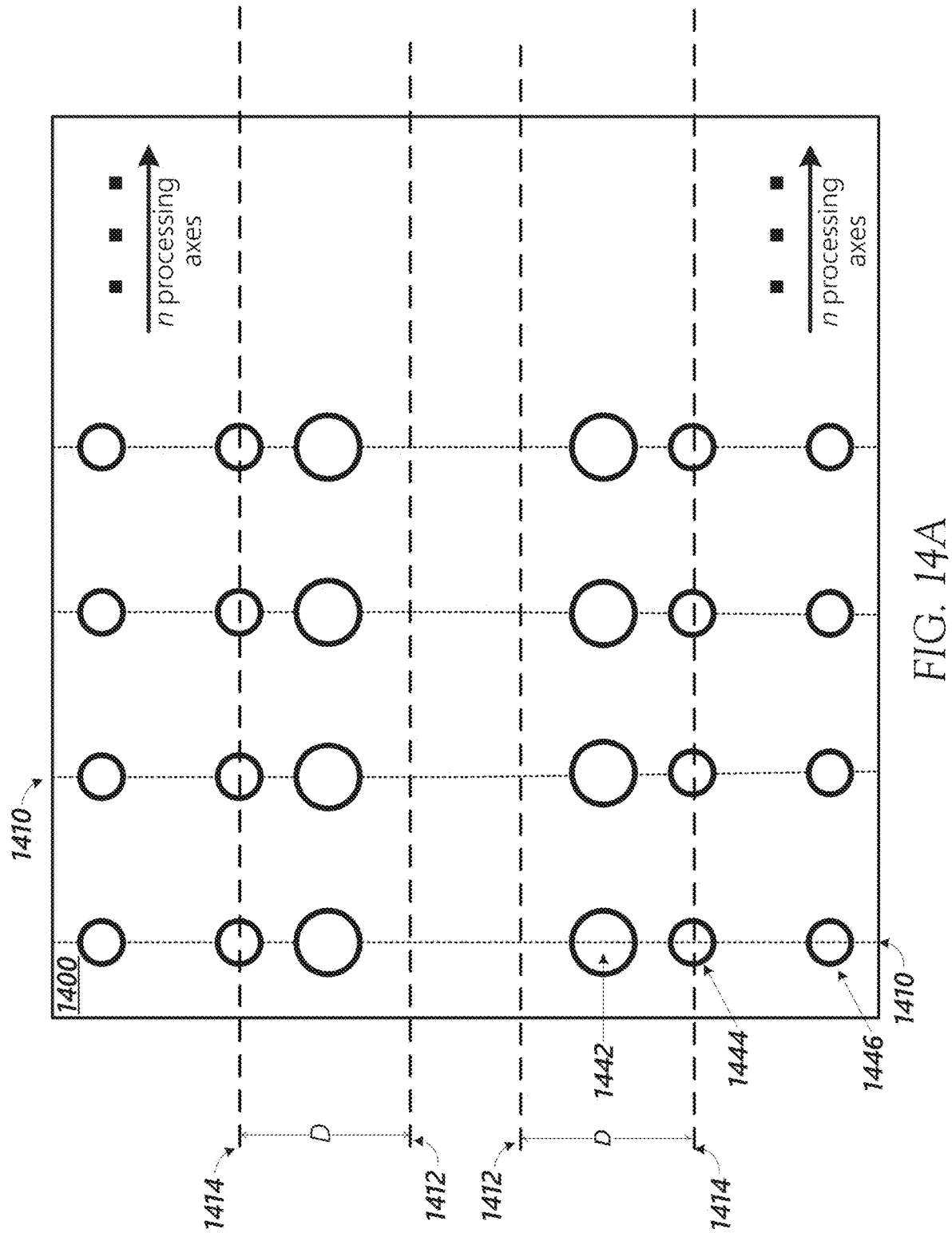
FIG. 14A illustrates a top-down conceptual view of a processing plate used in some embodiments of a diagnostic or preparatory apparatus, in accordance with embodiments disclosed herein.
Figure 14B:
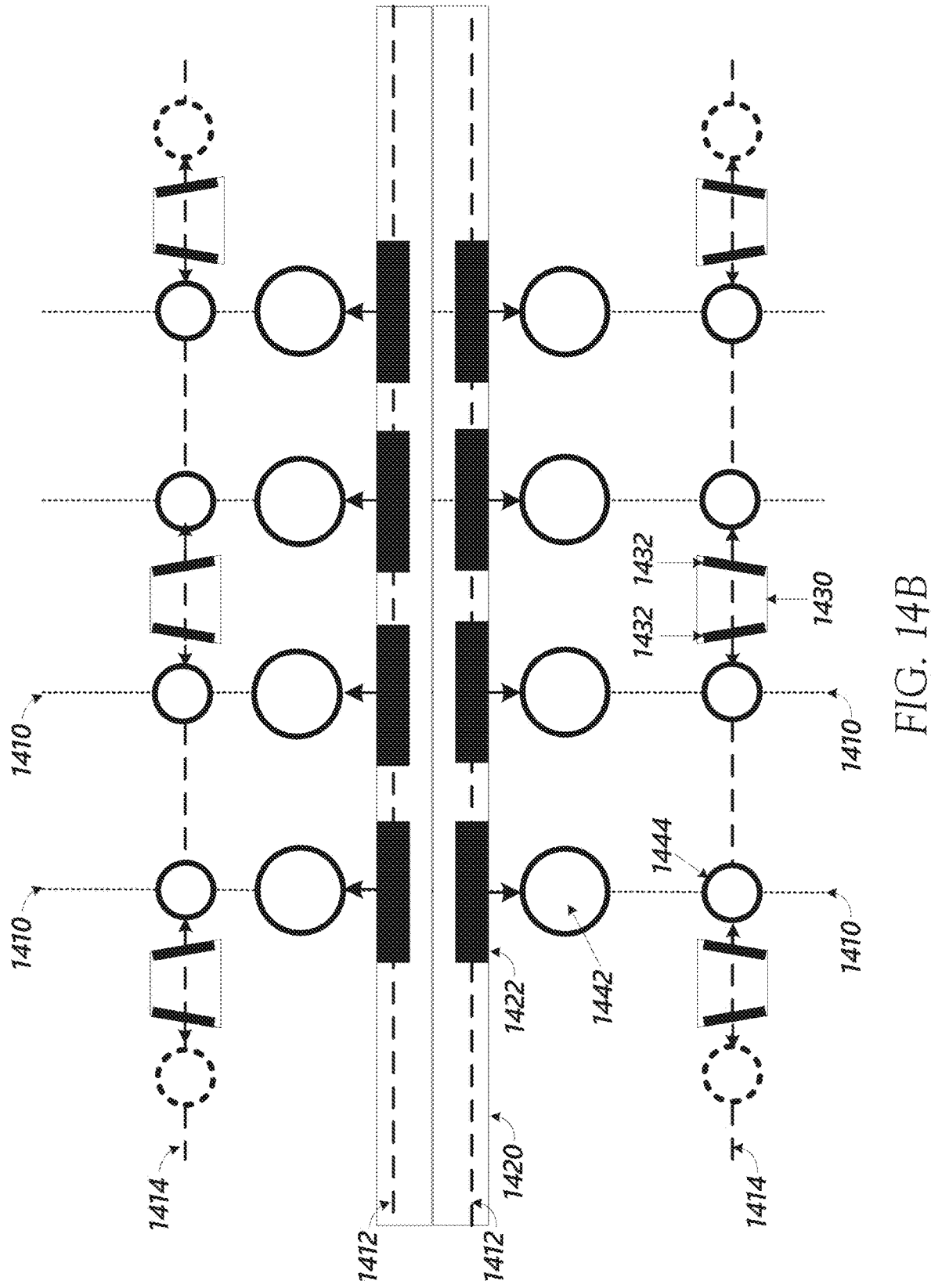
FIG. 14B illustrates a top-down conceptual view of the positions of certain components of a processing plate relative to magnets in some embodiments of a diagnostic or preparatory apparatus, in accordance with embodiments disclosed herein.
Figure 14C:
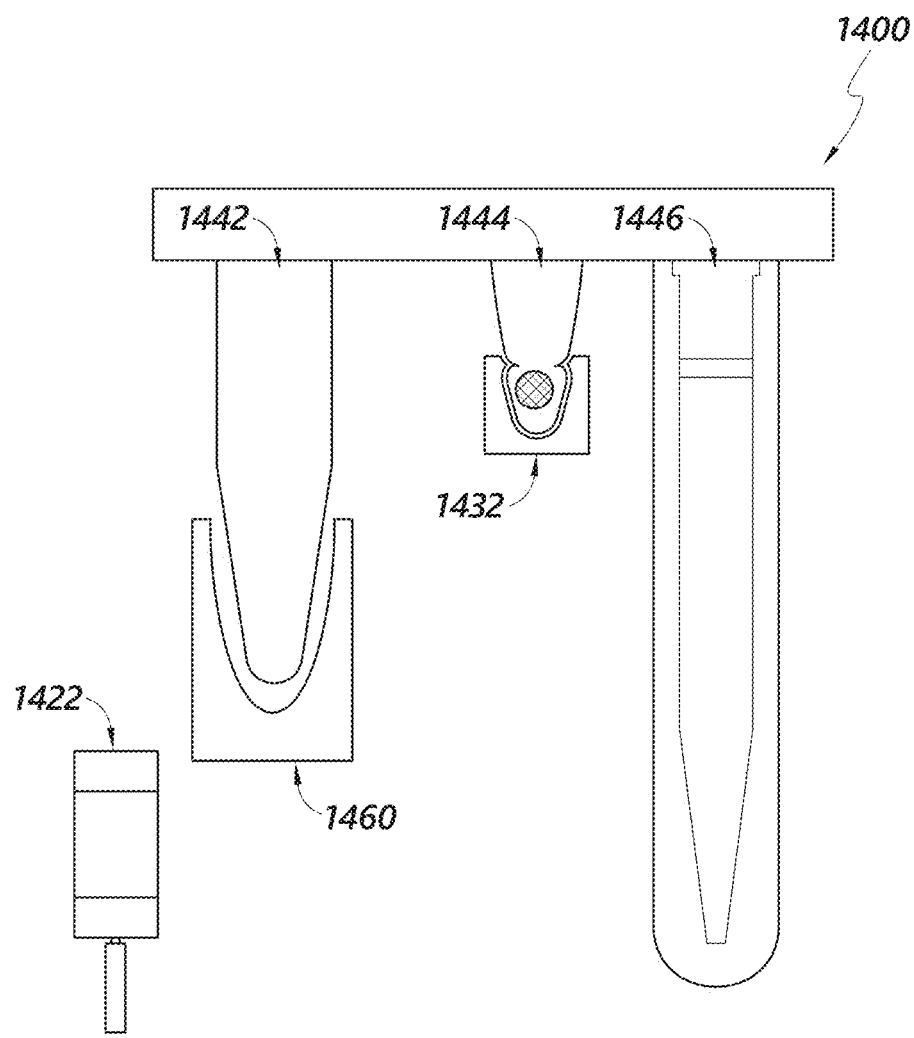
FIG. 14C illustrates a side profile conceptual view of the positions of certain components of a processing plate relative to magnets in some embodiments of a diagnostic or preparatory apparatus, in accordance with embodiments disclosed herein.
Figure 15A:
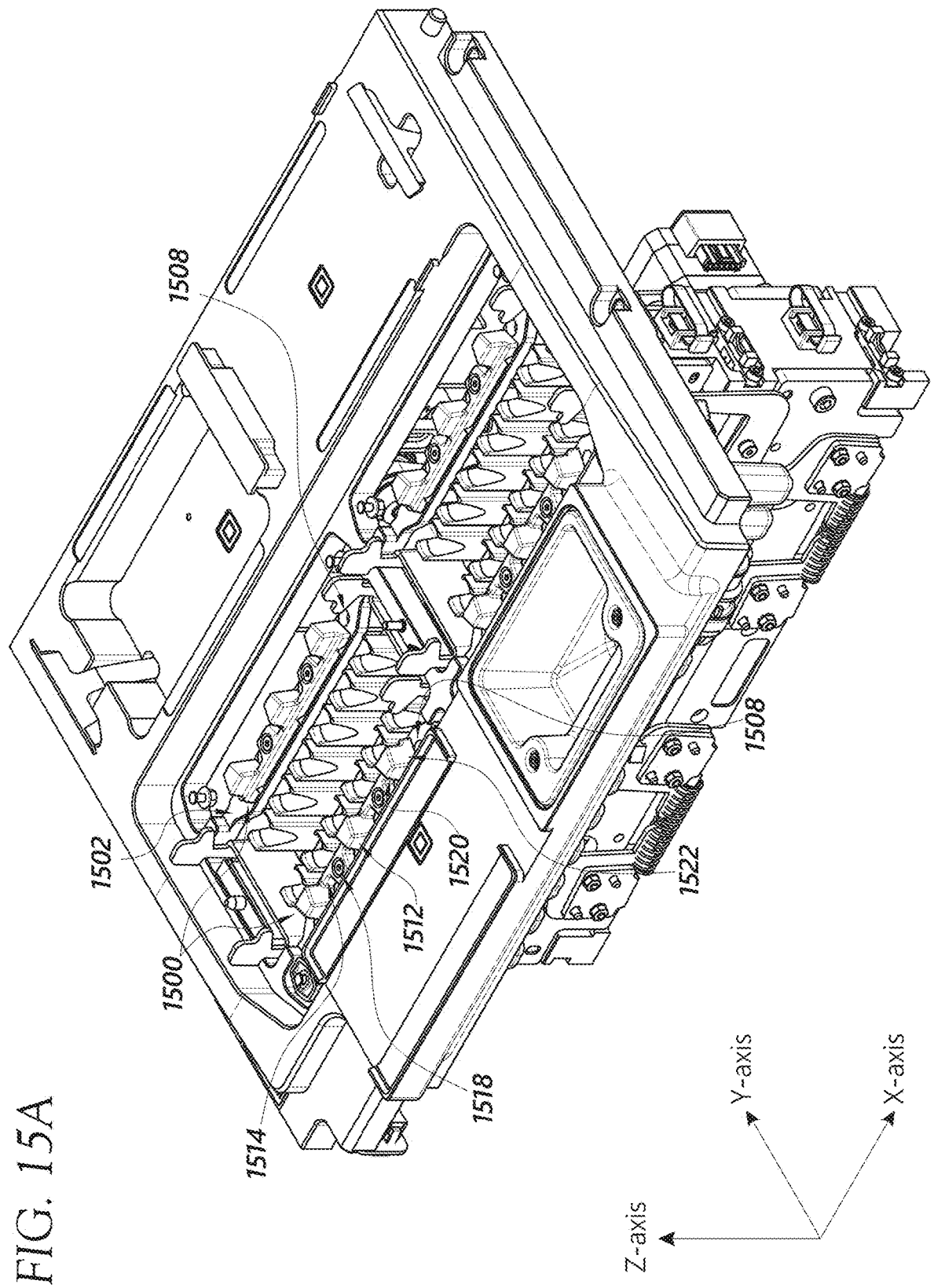
FIGS. 15A-15D illustrate isometric views of a fixed magnet assembly used in some embodiments of a diagnostic or preparatory apparatus, in accordance with embodiments disclosed herein.
Figure 15B:
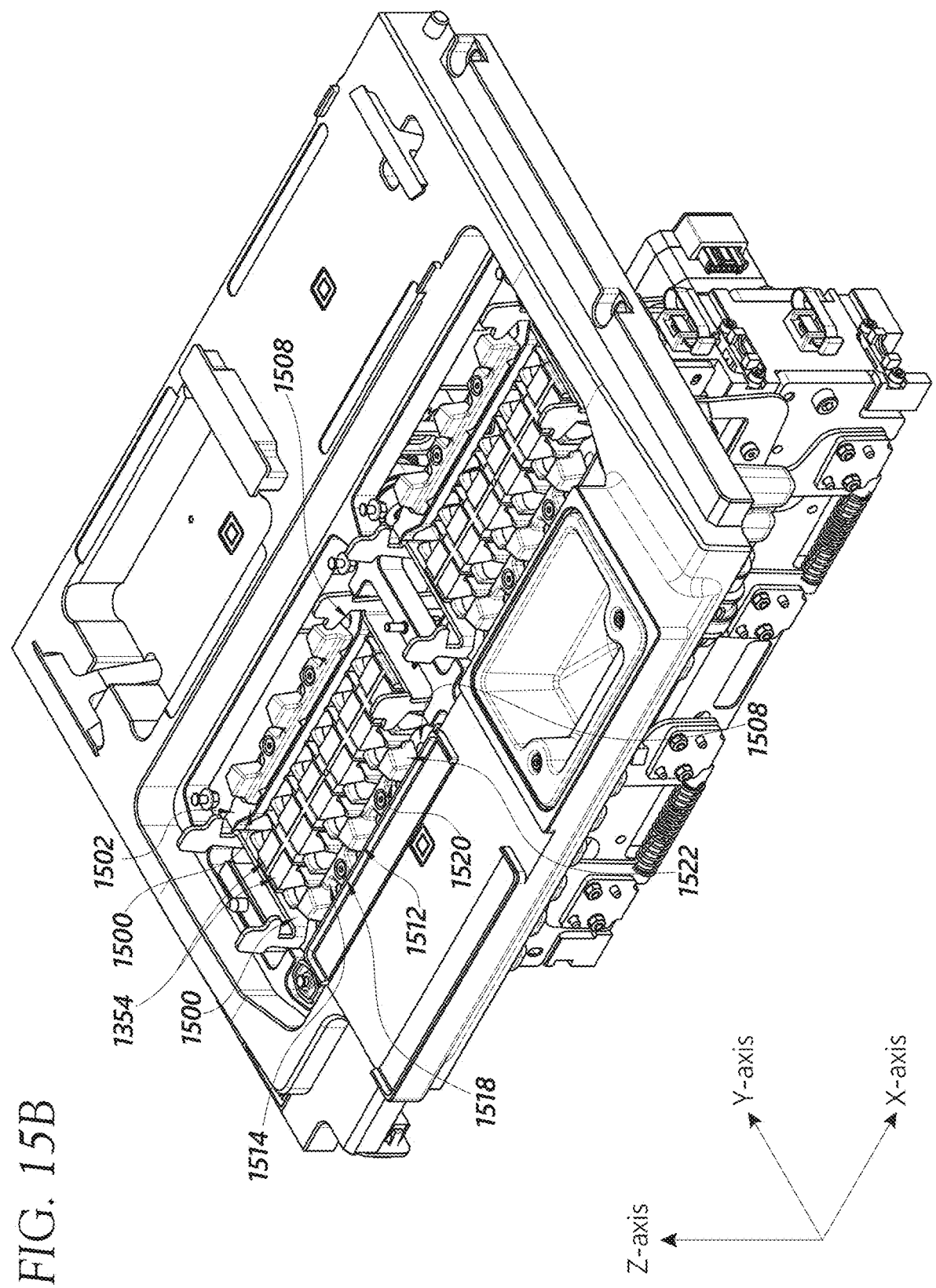
Figure 15C:
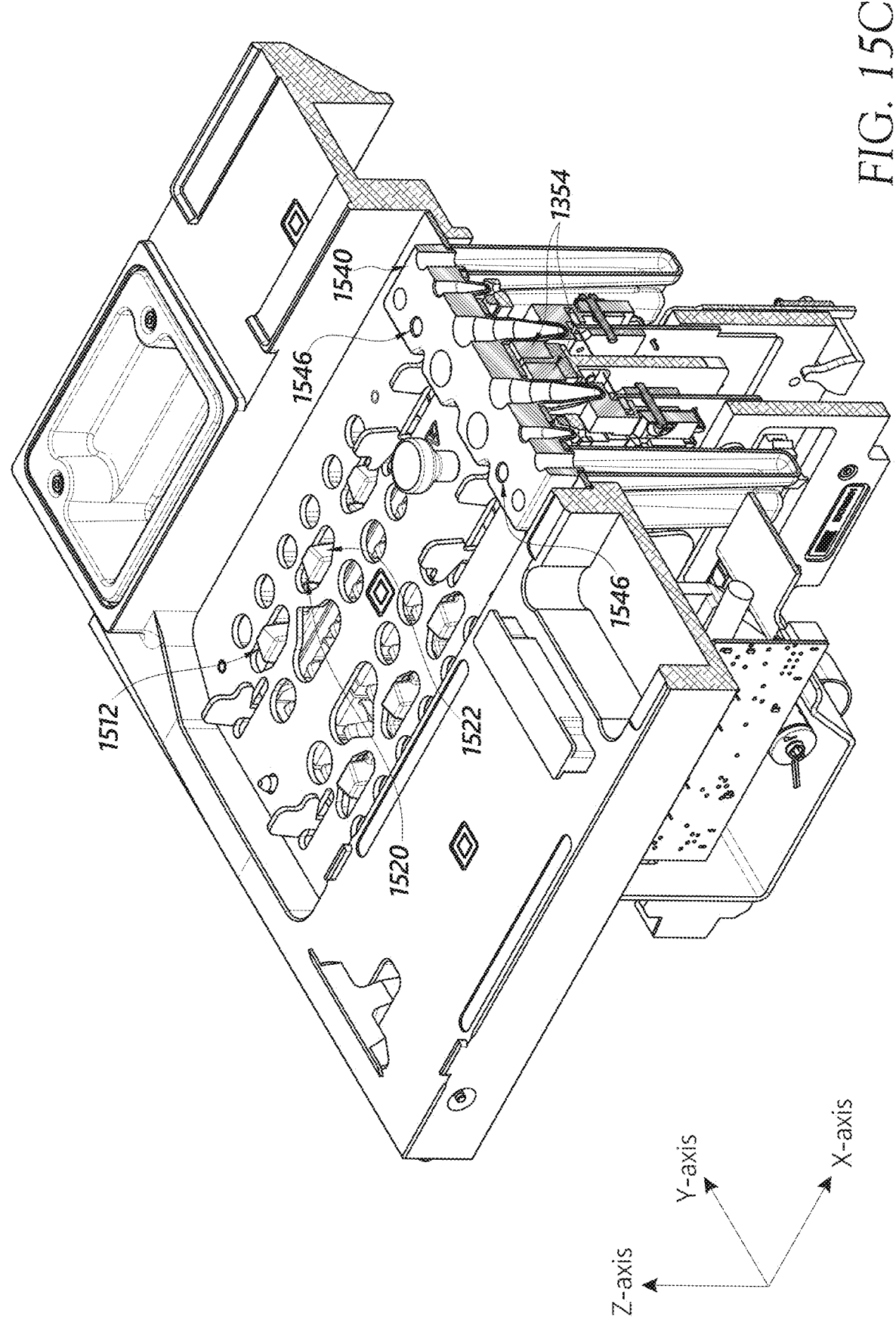
Figure 15D:
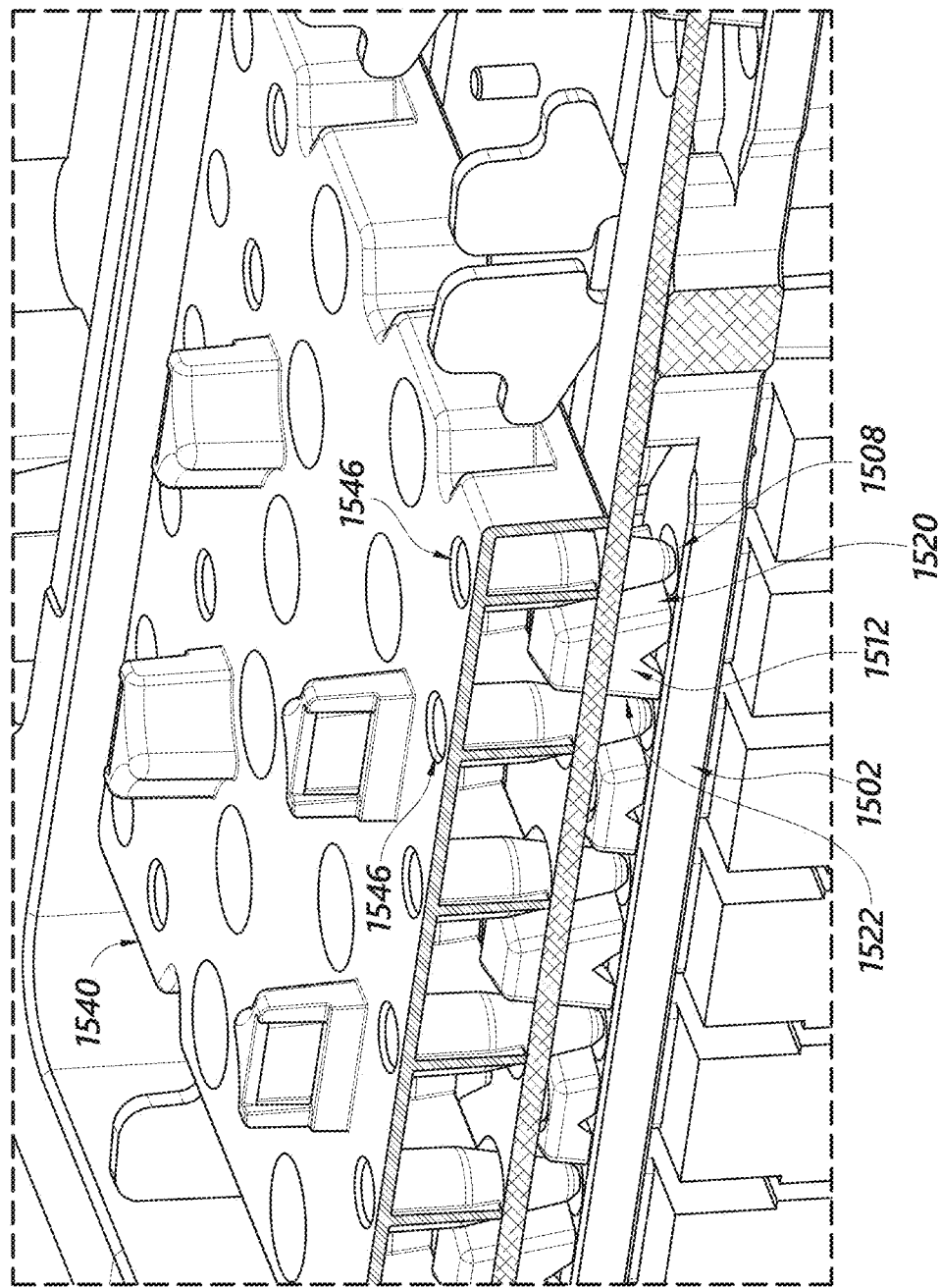

FIG. 13A is an isometric view of the internals of some embodiments of a diagnostic or preparatory apparatus. FIG. 13B is a side profile view of the internals of some embodiments of a diagnostic or preparatory apparatus, with a processing plate in position for sample processing. FIGS. 13A and 13B are described together.

As can be seen in FIG. 13A, a first extractor 1340 and a second extractor 1350 are visible as part of a single assembly, which may include, among other things, a housing 1342, printed circuit boards 1347 ("PCB"), a motor 1344, a number of heater assemblies 1348, and a number of magnetic separators 1341. There may be any number of heating assemblies 1348 and magnetic separators 1341. In some embodiments, the heater assemblies 1348 and the magnetic separators 1341 can be controlled by electronic circuitry such as on the PCBs 1347 (e.g., to cause the heater assemblies 1348 to apply heat independently to the process tubes of the processing plate(s)). It can also be configured to cause the magnetic separators 1341 to move up and down relative to the process tubes of the processing plate(s).

Similarly to the heater assembly 300 shown in FIGS. 3A-3C, a heater assembly 1348 may comprise one or more independently-controllable heater units, each of which comprises a heat block 1349. The heat blocks 1349 may be fashioned from a single piece of metal or other material, or may be made separately from one another and mounted independently of one another or connected to one another in some way. Thus, a heater assembly 1348 may include a collection of heater units but does not require the heater units or their respective heat blocks 1349 to be attached directly or indirectly to one another. Each of the heat blocks 1349 may be configured to align with and to deliver heat to a process tube 1314 of a processing plate 1310 (similar to a process tube 1244 of the processing plate 1240 shown in FIG. 12A), and the heater assembly 1348 can be configured so that each heater unit independently heats each of the one or more process tubes 1314 of the processing plate 1310, for example by permitting each of the one or more heat blocks 1349 to be independently controllable, as further described herein. There may be any number of independently-controllable heater units in one of the heater assemblies 1348. In various embodiments, there may be 2, 3, 4, 5, 6, 8, 10, 12, 16, 20, 24, 25, 30, 32, 36, 40, 48, or 50 independently-controllable heater units in a heater assembly 1348. There may be any number of heating assemblies 1348 used in the diagnostic or preparatory apparatus.

Similarly to the magnetic separator 370 shown in FIGS. 3A-3C, a magnetic separator 1341 may be configured to move one or more magnets 1354 relative to the one or more process tubes 1314 of processing plate 1310 (similar to process tubes 1244 of the processing plate 1240). The magnetic separator 1341 may move magnets 13541350 into close proximity to the process tubes 1314 (e.g., with each magnet 1354 of the magnetic separator 1341 having a face less than 2 mm, between 2 mm and 1 mm, or less than 1 mm away from the exterior surface of an adjacent process tube without being in contact with the process tube) in order to separate magnetic particles in the process tubes.

Structurally, a magnetic separator 1341 may include: one or more magnets 1354 affixed to a supporting member 1352; a motorized mechanism configured to move the supporting member 1352 in such a manner that the one or more magnets 1354 move backwards and forwards along a fixed axis (e.g., see motor 1344), and during at least a portion of the motion, the one or more magnets 1354 maintain close proximity to one or more process tubes 1314 which contain the magnetic particles in solution; and control circuitry to control the motorized mechanism (e.g., PCB 1347). The magnetic separators 1341 may operate together with the heater assemblies 1348 to permit successive heating and separation operations to be performed on liquid materials in the one or more process tubes 1314 without transporting either the liquid materials or the process tubes to different locations to perform either heating or separation. Such operation is also advantageous because it means that the functions of heating and separation which, although independent of one another, are both utilized in sample preparation, may be performed with a compact and efficient apparatus.

In the illustrated embodiment, there are four heating assemblies 1348, with each heating assembly 1348 having 6 independently-controllable heater units each comprising a heater block 1349. Up to two processing plates 1310 can be used at a time, and each processing plate 1310 involves the use of two heating assemblies 1348 with a magnetic separator 1341 between those two heating assemblies 1348. The magnetic separator 1341 may have two rows of 6 magnets (e.g., a row of 6 magnets on each side of the magnetic separator 1341), so as to form six pairs of adjacent magnets which face the two heating assemblies 1348 straddling the magnetic separator 1341. This side-by-side pairing of magnets may enhance the magnetic attraction of magnetic extraction particles within a process tube 1314 of a processing plate 1310 over that of a single magnet. Each magnet in the magnetic separator 1341 may be positioned to be adjacent to a heat block 1349 of one of the two heating assemblies 1348 when the magnetic separator 1341 is in a raised position. Each of the 12 heat blocks 1349 among those two heating assemblies 1348 may be specifically positioned to receive one of the 12 process tubes 1314 of the processing plate 1310 (e.g., the two rows of 6 process tubes 1244 shown in FIG. 12A). When motor 1344 is operated, the rows of magnets in the magnetic separator 1341 may be moved up into a space between the two rows of heat blocks 1349 to be in close proximity to the process tubes 1314 disposed therein.

As described earlier, in some cases, the magnetic separators 1341 can be integrated with the heater assemblies 1348 (e.g., one of the magnetic separators 1341 and the two heating assemblies 1348 straddling it), and they may be collectively referred to as an integrated magnetic separator and heater assembly. Additionally, although not shown in FIGS. 13A and 13B, an enclosure can cover the internals of the diagnostic or preparatory apparatus (including the magnetic separators 1341 and heater assemblies 1348) for protection of sub-assemblies and aesthetics.

FIG. 14A illustrates a top-down conceptual view of a processing plate used in some embodiments of a diagnostic or preparatory apparatus. More specifically, FIG. 14A shows an example processing plate 1400 (similar to the processing plate 1240 shown in FIGS. 12A and 12B) that can be used with some embodiments of an automated diagnostic or preparatory apparatus (e.g., the ones described in FIGS. 11, 13A, and 13B). The processing plate 1400 may have two rows of process tubes 1442, two rows of mixing tubes 1444, and two rows of pipette tip holding stations 1446.

Each process tube 1442 may be associated with a mixing tube 1444 and a pipette tip holding station 1446, and they may be aligned along a processing axis 1410, with the diagnostic or preparatory apparatus configured to perform processing and operations (e.g., the transfer of liquids) along each processing axis 1410. Accordingly, a total of n processing axes 1410 may be conceptualized—one for each process tube 1442 in the processing plate 1400.

When the processing plate 1400 is in use by the automated diagnostic or preparatory apparatus, a magnetic separator (e.g., magnetic separator 1341) having two rows of magnets may be positioned between the two rows of process tubes 1442. This can be seen in FIG. 13B. Each row of magnets of the magnetic separator may be aligned on a common axis (e.g., the common axis that passes through the midpoint of the magnets in that row), which may be referred to as a first magnet axis. Thus, a magnetic separator having two rows of magnets may have a first magnet axis for each of the two rows, which are represented by the first magnet axes 1412 in FIG. 14A. Each first magnet axis 1412 may run horizontally, parallel to the adjacent row of process tubes 1442. Each first magnet axis 1412 may be positioned, such that, when the magnetic separator is raised, the magnets of the magnetic separator that are aligned on that first magnet axis 1412 come into close proximity with the process tubes 1442 in the adjacent row of process tubes 1442 (e.g., within 2 mm of each process tube 1442 in the row).

In some embodiments, two separate fixed magnet assemblies may be implemented into the automated diagnostic or preparatory apparatus. Each fixed magnet assembly may include a set of magnets in a row, which may be aligned on a common axis (e.g., the common axis that passes through the midpoint of all the magnets). This common axis associated with a fixed magnet assembly may be referred to as a second magnet axis. The second magnet axes for both fixed magnet assemblies are represented by the second magnet axes 1414 in FIG. 14A. The two fixed magnet assemblies can be positioned so that each of the second magnet axes 1414 is close to one of the two rows of mixing tubes 1444, such that the magnets of a fixed magnet assembly are in close enough proximity to the adjacent row of mixing tubes 1444 to exert a magnetic force on any magnetic extraction particles contained in those mixing tubes 1444. The magnetic force can be of a sufficient strength to hold magnetic extraction particles in solution in the mixing tubes 1444 against an interior wall of the mixing tubes 1444, for example while the solution is being transferred out of the mixing tubes 1444 during a pipetting operation. With two separate fixed magnet assemblies, each second magnet axis 1414 may run horizontally through one of the two rows of mixing tubes 1444. Alternatively, a second magnet axis 1414 can run behind or in front of a row of mixing tubes 1444, in either case in close enough proximity to impart a magnetic force on the contents of the mixing tubes 1444 and capture any magnetic extraction particles contained therein. Additionally, each second magnet axis 1414 may be spaced far enough apart from the closest first magnet axis 1414 such that the magnets of the fixed magnet assembly do not interfere with the magnets of the magnetic separator. For example, each first magnet axis 1412 can be spatially separated from a corresponding second magnet axis 1414 a distance "D" such that the one or more magnets aligned along the first magnet axis 1412 do not exert a magnetic force on contents of the mixing tubes 1444, and one or more magnets aligned along the second magnet axis 1414 do not exert a magnetic force on contents of the process tubes 1442.

The first magnet axes 1412 and the second magnet axes 1414 are further shown in FIG. 14B, which may provide additional context for understanding the first magnet axes 1412 and the second magnet axes 1414. FIG. 14B illustrates a top-down conceptual view of the positions of certain components of a processing plate relative to magnets in some embodiments of a diagnostic or preparatory apparatus, in accordance with one configuration of a fixed magnet assembly.

More specifically, FIG. 14B shows the positions of two rows of process tubes 1442 and mixing tubes 1444 of a processing plate, along with the processing axis 1410 associated with each of the process tubes 1442. A magnetic separator 1420 having two rows of magnets 1422 is located between the two rows of process tubes 1442. It can be seen that there are two different first magnet axes 1412, which correspond to each of the two rows of magnets 1422 of the magnetic separator 1420. In this example implementation, the magnets 1422 are in one-to-one correspondence with the process tubes 1442. In practice, when the magnetic separator 1420 is raised to bring the magnets 1422 into close proximity to the process tubes 1422, the magnets 1422 exert a magnetic force (shown as vertical vectors in FIG. 14B) on the contents of the process tubes 1442.

Also shown in FIG. 14B are the magnets 1432 of two separate fixed magnet assemblies according to the disclosed technology. In some embodiments, the magnets 1432 of a fixed magnet assembly can be arranged in pairs. Each pair of magnets 1432 can be located within a housing 1430. A fixed magnet assembly may include multiple housings 1430. The pairs of magnets 1432 can be positioned within the diagnostic or preparatory apparatus, such that each pair of magnets 1432 is located between two adjacent mixing tubes 1444 of a processing plate (in the manner shown in the figure) when the processing plate is in the receiving bay of the diagnostic or preparatory apparatus. There may be a magnet 1432 for each mixing tube 1444 in the processing plate, and when the processing plate is in the receiving bay of the diagnostic or preparatory apparatus, each magnet 1432 may be in close proximity with an adjacent mixing tube 1444. All of the magnets 1432 of a fixed magnet assembly may be aligned on (or substantially aligned on) a second magnet axis 1414. With two separate fixed magnet assemblies, there are two separate second magnet axes 1414, each of which corresponds to the row of magnets 1432 in one of the two fixed magnet assemblies. In this example implementation, the magnets 1432 are in one-to-one correspondence with the mixing tubes 1444, and each of the magnets 1432 may exert a magnetic force (shown as horizontal vectors in FIG. 14B) on the contents of an adjacent mixing tube 1444.

FIG. 14C illustrates a side profile conceptual view of the positions of certain components of a processing plate relative to magnets in some embodiments of a diagnostic or preparatory apparatus, in accordance with embodiments disclosed herein.

More specifically, FIG. 14C shows a process tube 1442, a mixing tube 1444, and a pipette tip holding station 1446 associated with one processing axis 1410 of a processing plate 1400. The process tube 1442 may be used during sample preparation for cell lysis and extraction of nucleic acids, such as DNA or RNA of a patient, and DNA or RNA of a pathogen. The process tube 1442 may be positioned in a location such that the process tube 1442 disposed within a heater block 1460 of a heater assembly (e.g., heater assembly 1348 shown in FIG. 13A) when the processing plate 1400 is in the receiving bay of the diagnostic or preparatory apparatus. A first magnet 1422 of the magnetic separator may be raised to be in close proximity to the process tube 1442 in order to exert a magnetic force on the contents of the process tube 14442. The mixing tube 1444 may be positioned in a location that is in close proximity to a second magnet 1432 of a fixed magnet assembly, such that the second magnet 1432 exerts a magnetic force on the contents of the mixing tube 1444.

Preparation of a sample with this added fixed magnet assembly may proceed as follows. In some embodiments, the diagnostic or preparatory apparatus may pierce the extraction tube of an extraction plate (e.g., sealed dry reagent compartments of a dry reagent plate 1150) containing extraction reagent, which can include magnetic extraction particles, a lyophilized extraction reagent (e.g., dried lysis reagent), and internal controls. The magnetic particles may be configured to bind to specific molecules (e.g., DNA/RNA) in the sample. The diagnostic or preparatory apparatus may also pierce the relevant reagent compartments of a liquid reagent plate 1160. The diagnostic or preparatory apparatus may then transfer some raw sample into the process tube 1442. The amount of raw sample transferred may depend on the type of assay or procedure. The diagnostic or preparatory apparatus may move some of the extraction reagent (e.g., an extraction buffer) from the extraction tube of the extraction plate into the process tube 1442.

The contents of process tube 1442, which is disposed in the heater block 1460 of a heater unit, are then heated by the heater block 1460. The temperature and duration of the heating is determined by the type of assay or procedure. The heating and lysis reagent causes the cells from the sample to break open, and some of the target nucleic acid (for example, DNA or RNA) contained in the cells and the internal controls may attach or bind to the magnetic particles (e.g., magnetic binding particles or beads).

The first magnet 1422 of the magnetic separator may be raised until it is in close proximity to the process tube 1442. The magnet 1422 may exert a magnetic force on the magnetic particles in the process tube 1442, drawing the magnetic particles and the attached nucleic acid to the side of the process tube 1442. The diagnostic or preparatory apparatus may extract the liquid from the process tube 1442 while the magnet 1422 is still drawing the magnetic particles and attached nucleic acid to the side of the process tube 1442. Ideally under normal operating, this liquid should not contain the magnetic particles and attached nucleic acid, which are held against the inner side wall of the process tube 1442 as the liquid is extracted. The diagnostic or preparatory apparatus may dispense of the extracted liquid.

The first magnet 1422 of the magnetic separator may be lowered, thereby removing the magnetic force holding the magnetic particles and the attached nucleic acid to the side of the process tube 1442. The diagnostic or preparatory apparatus can transfer wash buffer into the process tube 1442 (e.g., from a reagent compartment of a liquid reagent plate 1160) to be mixed in with the magnetic particles bound to nucleic acid in the process tube 1442. Afterwards, the first magnet 1422 of the magnetic separator may be raised again until it is in close proximity to the process tube 1442. The magnet 1422 may exert a magnetic force on the magnetic particles in the process tube 1442, again drawing the magnetic particles and the attached nucleic acid to the side of the process tube 1442.

With the magnetic particles moved to the side of the process tube 1442, the liquid contents (e.g. primarily the added wash buffer) can be extracted from the process tube 1442 and disposed of. Ideally under normal operating conditions, this extracted liquid should not contain the magnetic particles and attached nucleic acids, which are held against the inner side wall of the process tube 1442 as the liquid is extracted. Afterwards, the first magnet 1422 of the magnetic separator may be lowered, thereby removing the magnetic force holding the magnetic particles and the attached nucleic acid to the side of the process tube 1442.

An elution or release buffer (e.g., from a reagent compartment of a liquid reagent plate 1160) can be added to the process tube 1442, which contains the magnetic particles and attached nucleic acid. The release buffer may cause the magnetic particles to separate from the nucleic acid and internal controls. The diagnostic or preparatory apparatus can transfer neutralizing buffer (e.g., from a reagent compartment of a liquid reagent plate 1160) to the mixing tube 1444, which is empty up to this point. At this point, the process tube 1442 will contain the magnetic particles, the separated nucleic acid (e.g., DNA/RNA), and internal controls. The mixing tube 1444 contains neutralizing buffer.

The heater block 1460 is activated a second time to heat the contents of the process tube 1442. The temperature and duration of the heating will be dependent on the assay or procedure performed. The first magnet 1422 of the magnetic separator may be raised yet again, until it is in close proximity to the process tube 1442. The first magnet 1422 may exert a magnetic force on the magnetic particles in the process tube 1442, drawing the magnetic particles to the inner side wall of the process tube 1442 (but not the nucleic acid, e.g., DNA/RNA molecules, which are no longer attached to the magnetic particles). While the magnetic particles are drawn to and held against the inner side wall of the process tube 1442 by the first magnet 1422, the liquid contents (e.g. the nucleic acid mixture with the added release buffer) are extracted from the process tube 1442 without extracting the magnetic particles. The nucleic acid mixture can be transferred to the mixing tube 1444 that contains the neutralizing buffer. The neutralizing buffer is configured to lower the pH of the nucleic acid mixture to a neutral pH. The first magnet 1422 of the magnetic separator may be lowered.

In some embodiments, a dry reagent compartment of an amplification reagent plate, which contains PCR master mix reagent containing probes and primers used in PCR amplification, may be accessed. The PCR master mix reagent may be in the form of a lyophilized bead. The diagnostic or preparatory apparatus may transfer the contents of the mixing tube 1444 into the compartment of the amplification reagent plate containing the PCR master mix reagent, and the neutralized nucleic acid mixture from the mixing tube 1444 may dissolve the PCR master mix pellet. However, as the contents are extracted from the mixing tube 1444, the second magnet 1432 of the fixed magnet assembly may exert a magnetic force on the contents of the mixing tube 1444. In particular, there may be some magnetic particles (e.g., beads) that were transferred into the mixing tube 1444 from the process tube 1442 despite efforts to prevent this from occurring (e.g., using the first magnet 1422 to keep the magnetic particles in the process tube 1422). The second magnet 1432 may be used as part of an additional filtering step to remove any leftover magnetic particles, carried over from the process tube 1422 (e.g., "carryover" magnetic particles), from the neutralized nucleic acid mixture as it is extracted from mixing tube 1444.

The resulting mixed solution in the dry reagent compartment of the amplification reagent plate, which contains rehydrated PCR master mix reagent and the neutralized nucleic acid mixture, can be transferred to a device, including a storage device where the sample is stored or a microfluidic cartridge where it is amplified (e.g., the microfluidic cartridge 1170 shown in FIG. 11).

FIGS. 15A-15D illustrate isometric views of a fixed magnet assembly according to the disclosed technology used in some embodiments of a diagnostic or preparatory apparatus.

An embodiment of a fixed magnet assembly 1500 is shown that can be implemented for the embodiments of the diagnostic or preparatory apparatus shown and described in FIGS. 11, 13-13B, and 14A-14C. Four separate fixed magnet assemblies 1500 can be installed as shown, each of which may include a support plate 1502, which may have dimensions suited to the particular diagnostic or preparatory apparatus in which the fixed magnet assembly 1500 is implemented. In some embodiments, the support plate 1502 may be a machined aluminum plate. The support plate 1502 may include a set of recesses or holes 1508, each of which is configured to receive the bottom end of a mixing tube 1546 (similar to the mixing tube 1316 shown in FIG. 13B or the mixing tube 1444 shown in FIG. 14A-14C) of a processing plate 1540.

The fixed magnet assembly 1500 may also include a set of magnet housings 1512. The magnet housings 1512 can be integrally formed as a single, monolithic piece. The magnet holder 1500 may include a set of magnet housings 1512 and connectors 1514. The magnet housings 1512 and the connectors 1514 can be integrally formed as a single, monolithic piece. In another example, the magnet housings 1512 and the connectors 1514 are coupled to form the magnet holder 1500. Other configurations can be suitably implemented. In some embodiments, each magnet housing 1512 may have a trapezoidal shape when viewed from top-down. In this example, each magnet housing 1512 houses two magnets (not shown) that are located adjacent to a first face 1520 and a second face 1522 of the magnet housing 1512, respectively. This arrangement may be similar to how FIG. 14B shows the pair of magnets 1432 are arranged within the housing 1430. The fixed magnet assembly 1500 may include mounting holes 1518 for attaching the magnet housings 1512 to the support plate 1502. For instance, fasteners (e.g., screws) can be inserted into the mounting holes 1518 to affix the magnet housings 1512 to the support plate 1502 and form the fixed magnet assembly 1500. The support plate 1502 of the fixed magnet assembly 1500 can then be installed in (for example, affixed to) the diagnostic or preparatory apparatus using any suitable mechanism.

In one non-limiting example, the fixed magnet assembly 1500 is a single, monolithic piece that includes a plurality of magnet housings 1512 separated by connectors 1514. In some cases, the fixed magnetic assembly is a unitary structure that includes a plurality of magnet housings 1512. A unitary fixed magnet assembly 1500 can be formed, for example, of a magnetic material. In another non-limiting example, a unitary fixed magnet assembly 1500 is formed of one or more non-magnetic materials, and a magnetic material is coupled to interior walls of the housing adjacent to the first face 1520 and the second face 1522 of each magnet housing 1512. Other configurations are possible.

In some embodiments, the magnet housings 1512 of each fixed magnet assembly 1500 may have a fixed height (e.g., up/down position) relative to the support plate 1502 and the rest of the diagnostic or preparatory apparatus. This fixed height may be adjusted by adding a shim of a desired height measured in the z-direction between the magnet housings 1512 and the supporting plate 1502. Installation of the fixed magnet assembly 1500 can include selecting one of a plurality of shims of different heights from an installation kit, installing the selected shim in a receiving bay, and installing the fixed magnet assembly 1500 over the shim in the z-direction. This can be particularly advantageous when a fixed magnet assembly is retrofitted into existing preparatory and diagnostic apparatuses in the field, in view of very slight differences in the dimensions and tight tolerances associated with receiving bays and racks implemented in the apparatuses. In some other embodiments, the spring-based mechanism shown in FIGS. 9 and 10A-10B can be used for the fixed magnet assembly 1500 to allow for the support plate 1502 of the installed fixed magnet assembly 1500 to move upward or downward in the z-direction.

Thus, the mixing tubes 1546 of the processing plate 1540 may be received in the holes 1508 of the support plate 1502, resulting in each mixing tube 1546 being in close proximity with a magnet in an adjacent magnet housing 1512 (e.g., a magnet located behind either a first face 1520 or second face 1522 of the adjacent magnet housing 1512). In some embodiments, the first face 1520 and the second face 1522 of each magnet housing 1512 may be oriented at an angle that makes them parallel to the sloped wall of the mixing tubes 1546 when the mixing tubes are disposed in the holes 1508.

Figure 16A:
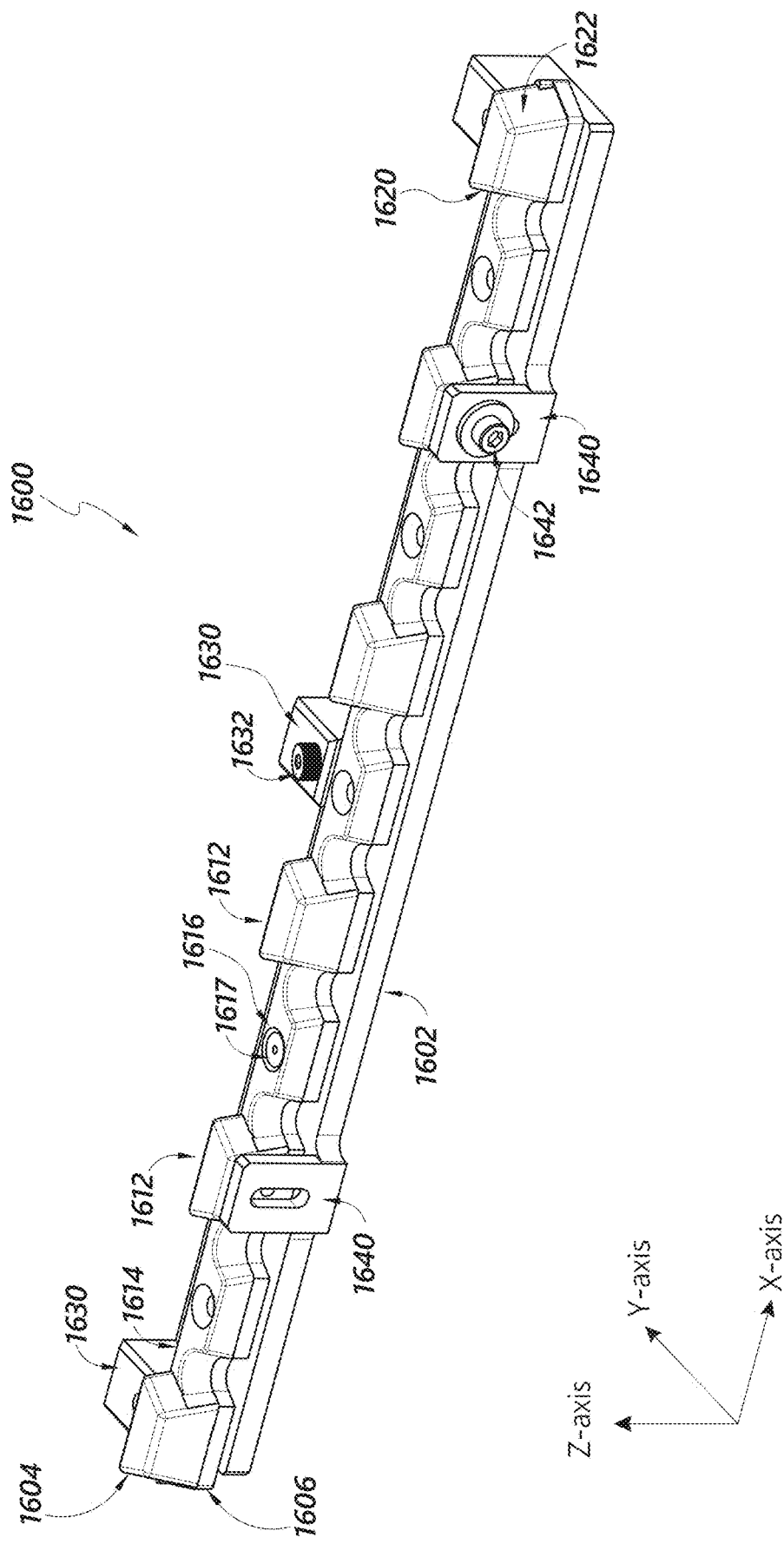
FIGS. 16A-16C illustrate isometric views of an embodiment of a fixed magnet assembly used with an automated diagnostic or preparatory apparatus, in accordance with embodiments disclosed herein.
Figure 16B:
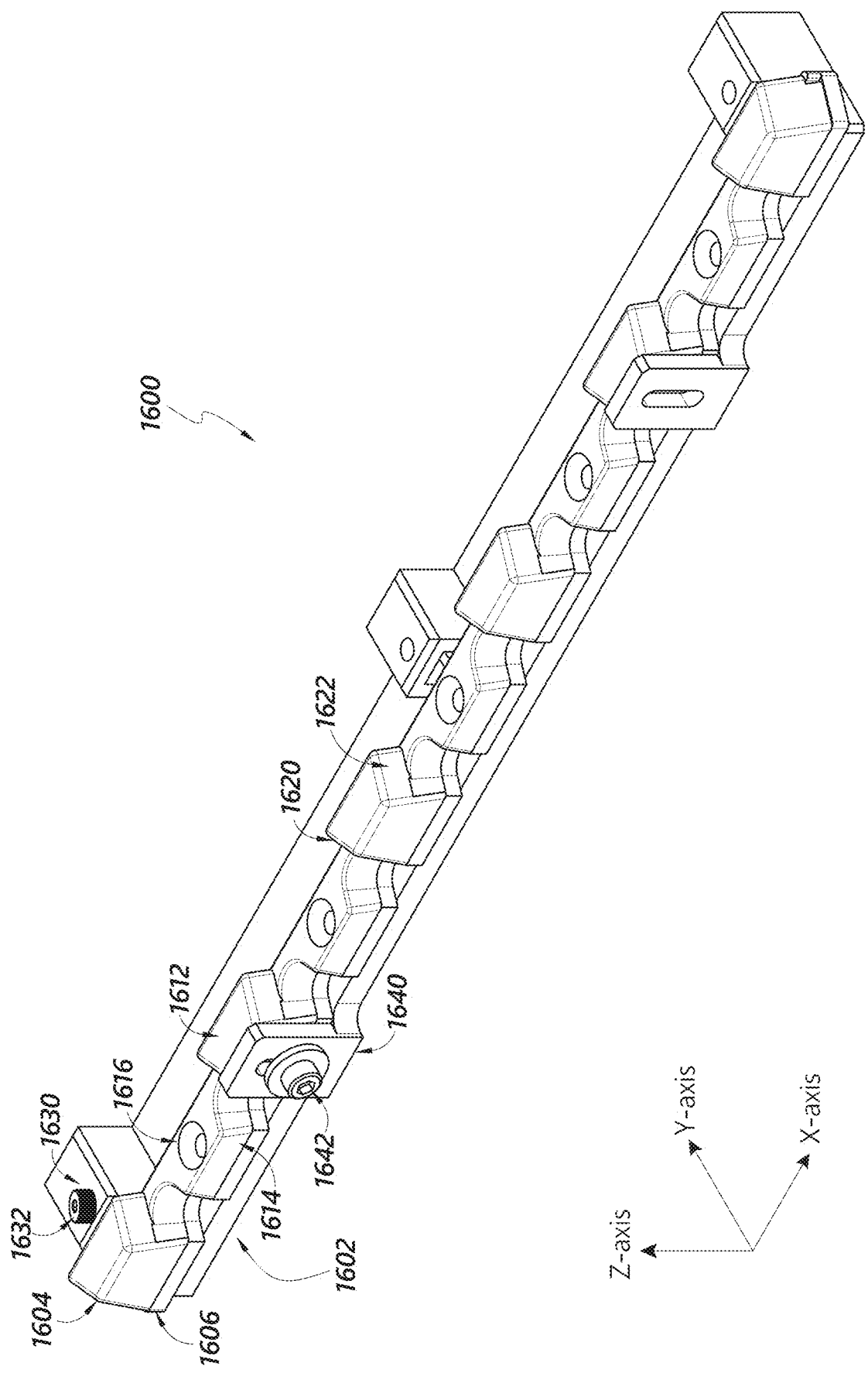
Figure 16C:
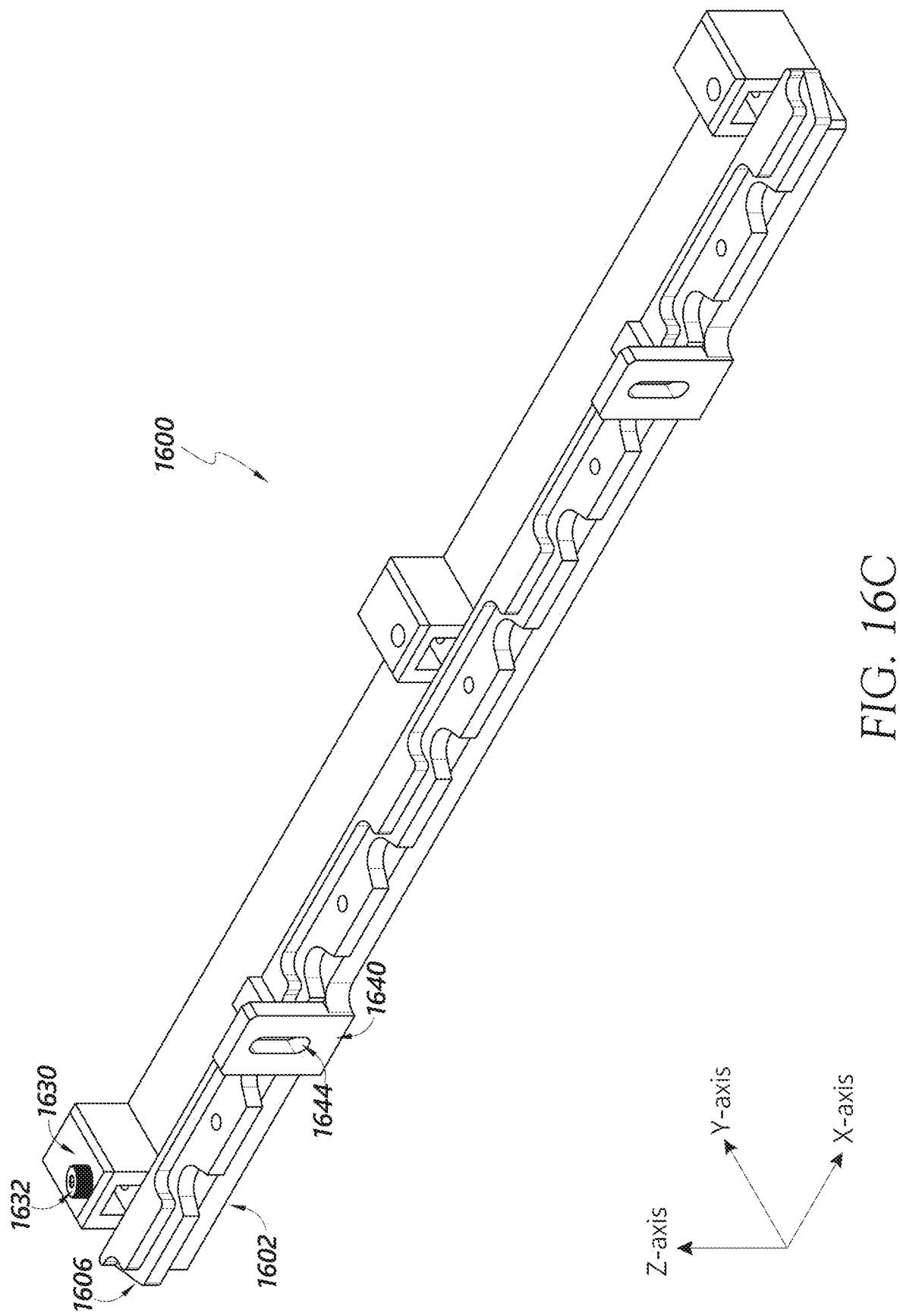
Figure 16D:
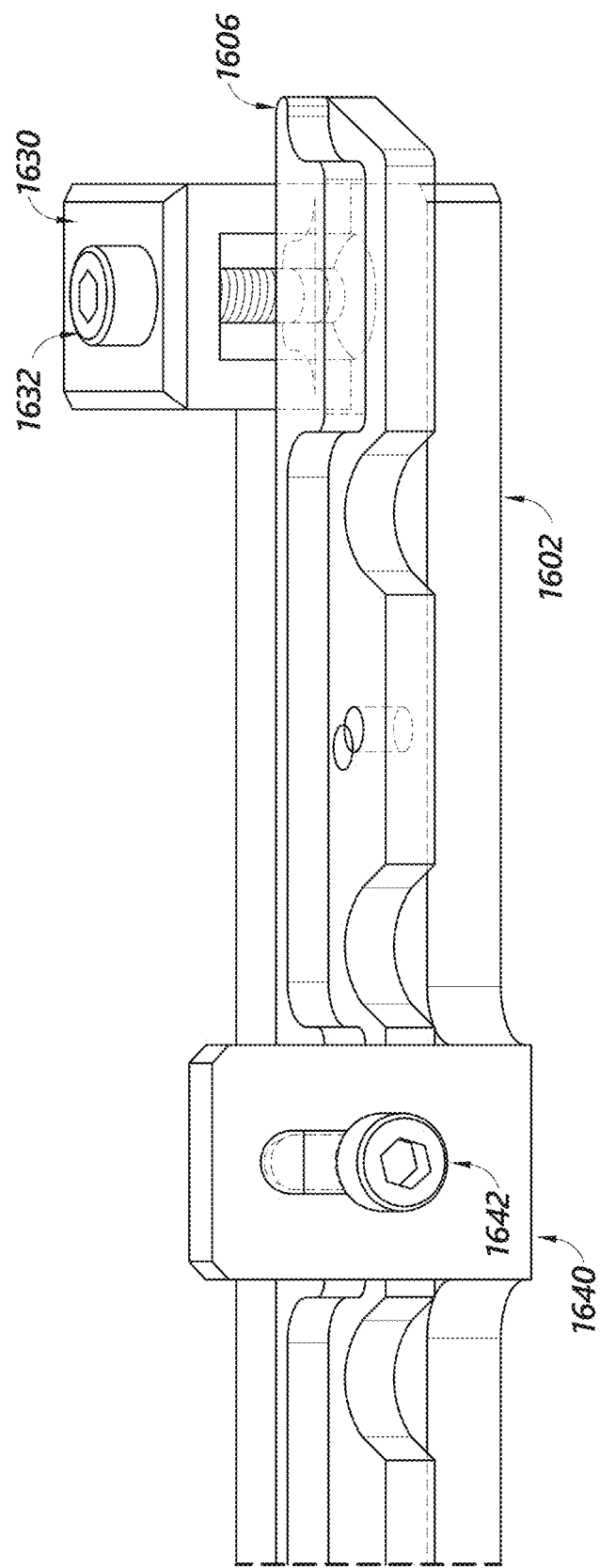
FIG. 16D illustrates a perspective view of a fastening mechanism used in an embodiment of a fixed magnet assembly, in accordance with embodiments disclosed herein.
Figure 16E:
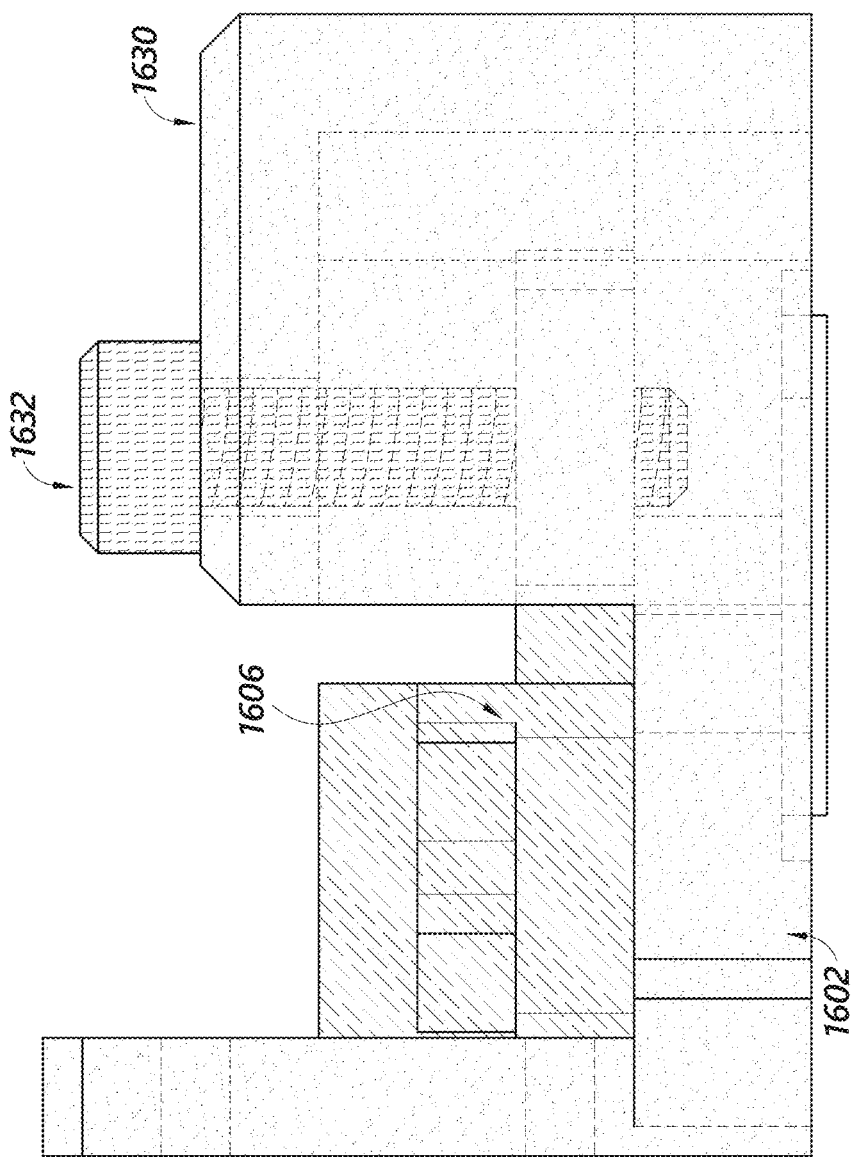
FIG. 16E illustrates a side cutaway view of a fastening mechanism used in an embodiment of a fixed magnet assembly, in accordance with embodiments disclosed herein.
Figure 16F:
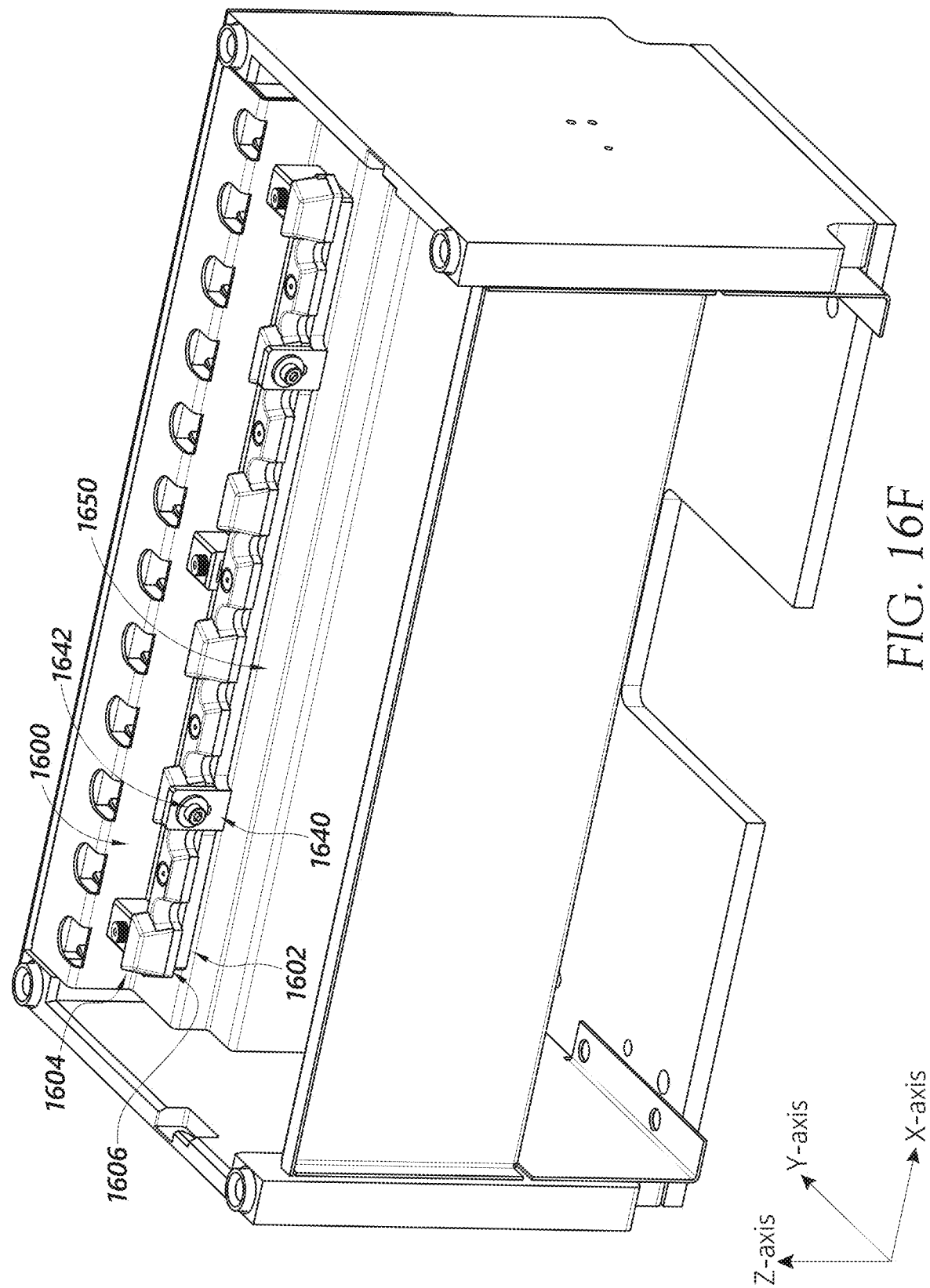
FIG. 16F illustrates an isometric view of an embodiment of a fixed magnet assembly affixed to a cover of an automated diagnostic or preparatory apparatus, in accordance with embodiments disclosed herein.

FIGS. 16A-16B illustrate isometric views of an embodiment of another fixed magnet assembly that can be implemented according to the disclosed technology into an automated diagnostic or preparatory apparatus. More specifically, FIGS. 16A-16B show an embodiment of a fixed magnet assembly 1600 with user-adjustable height. FIG. 16C illustrates the fixed magnet assembly of FIGS. 16A-16B with the magnet housings 1612 and connectors 1614 omitted for illustrative purposes only. FIG. 16D illustrates a perspective view of the fastening mechanism implemented by the fixed magnet assembly of FIGS. 16A-16C, while FIG. 16E illustrates a side cutaway view of that fastening mechanism. FIG. 16F illustrates an isometric view of the fixed magnet assembly of FIGS. 16A-16C implemented in a receiving bay of a diagnostic or preparatory apparatus, such as within the receiving bay 500 described with reference to FIGS. 5A-5B.

The fixed magnet assembly 1600 may include a mounting plate 1602, a support plate 1606, and a magnet holder 1604. The mounting plate 1602 may have dimensions suited to the particular diagnostic or preparatory apparatus in which the fixed magnet assembly 1600 is implemented. In some embodiments, the mounting plate 1602 may be a machined aluminum plate. In some embodiments, the mounting plate 1602 may include a plurality of mounting brackets 1640 on one side. For instance, in the embodiment illustrated in the figures, there are two mounting brackets 1640 disposed on a front side of the mounting plate 1602, which extend upwards from the mounting plate 1602 (e.g., in the z-axis). Each mounting bracket 1640 may have a vertical slot 1644, through which a fastener 1642 can be disposed. The fastener 1642 may be disposed through the vertical slot 1644 and into a corresponding recess (not shown) in the support plate 1606, which is configured to receive the fastener 1642. In some cases, the fasteners 1642 may be screws and tightening the fasteners 1642 may sandwich the mounting brackets 1640 between the fasteners 1642 and the support plate 1606, thereby mounting the support plate 1606 to the mounting brackets 1640 in order to resist re-positioning of the support plate 1606. In some embodiments, the mounting plate 1602 may also include fastener housings 1630, and a fastener 1632 may be disposed in each fastener housing 1630. In the embodiment illustrated in the figures, there are three fastener housings 1630 spaced along the length of the mounting plate 1602, with two of the fastener housings 1630 at each longitudinal end of the mounting plate 1602. It will be understood that other numbers, spacings, and configurations of the fastener housings 1630 are possible. Each fastener 1632 may be disposed through a recess in a fastener housing 1630 and also disposed through a corresponding recess in the support plate 1606 (as shown in FIG. 16E). In some cases, the fasteners 1632 may be screws and tightening the fasteners 1632 may thread them deeper through those recesses of the support plate 1606 to raise the support plate 1606 relative to the mounting plate 1602.

As will be described in further detail herein, the mounting brackets 1640 (and their vertical slots 1644), fasteners 1642, fastener housings 1630, and the fasteners 1632 may be some of the components that are configured to work together to enable the user to adjust the height of the support plate 1606 and/or the magnet holder 1604 of the fixed magnet assembly 1600 (relative to the mounting plate 1602). Once the mounting plate 1602 is fixed in place, the support plate 1606 and/or the magnet holder 1604 may be able to move up and down (e.g., along the z-axis) within a limited range, relative to the stationary mounting plate 1602, through the user-adjustable height feature. In some embodiments, the support plate 1606 may be the component that moves up and down (e.g., along the z-axis) relative to the mounting plate 1602 when using the user-adjustable height feature, such as when the fasteners 1632 (disposed in the fastener housings 1630) are turned clockwise and/or counter-clockwise.

The support plate 1606 may sit on top of the mounting plate 1602, sandwiched between the mounting plate 1602 and the magnet holder 1604. The magnet holder 1604 may include a set of magnet housings 1612 and connectors 1614. The magnet housings 1612 and the connectors 1614 can be integrally formed as a single, monolithic piece, or the magnet housings 1612 and the connectors 1614 may be coupled to form the magnet holder 1604. Other configurations can be suitably implemented. The dimensions of the support plate 1606 and the magnet holder 1604 may be suited to the particular diagnostic or preparatory apparatus in which the fixed magnet assembly 1600 is implemented. In some embodiments, the magnet holder 1604 may be made of a material that is chemically resistant to cleaning agents. In some embodiments, each magnet housing 1612 may have a trapezoidal shape when viewed from top-down. In this example, each magnet housing 1612 may house two magnets (not shown) that are located adjacent to a first face 1620 and a second face 1622 of the magnet housing 1612, respectively. This arrangement may be similar to how FIG. 6B shows the pair of magnets 632 are arranged within the housing 630.

In one non-limiting example, the fixed magnet assembly 1600 is a single, monolithic piece that includes a plurality of magnet housings 1612 separated by connectors 1614. In some cases, the fixed magnetic assembly is a unitary structure that includes a plurality of magnet housings 1612. A unitary fixed magnet assembly 1600 can be formed, for example, of a magnetic material. In another non-limiting example, a unitary fixed magnet assembly 1600 is formed of one or more non-magnetic materials, and a magnetic material is coupled to interior walls of the magnet housings 1612, adjacent to the first face 1620 and the second face 1622 of each magnet housing 1612. Other configurations are possible.

The magnet holder 1604 may have mounting holes 1616 (e.g., in the connectors 1614) for mechanically coupling the magnet holder 1604 to the mounting plate 1602. For instance, in some embodiments, fasteners 1617 (e.g., screws or shoulder bolts) can be inserted into the mounting holes 1616 (and also inserted through corresponding mounting holes in the support plate 1606, which are not shown) to mechanically couple the magnet holder 1604 to the support plate 1606 and/or the mounting plate 1602. In some embodiments, the fasteners 1617 may limit the maximum spacing between the support plate 1606 and the mounting plate 1602. The fasteners 1617 may place an upward limit to the upward movement of the support plate 1606 in the z-direction away from the mounting plate 1602, but do not limit downward movement of the support plate 1606 in the z-direction toward the mounting plate 1602. In some embodiments, the fasteners 1617 may additionally restrict the movement of the support plate 1606 in the x-axis and y-axis. With these fasteners 1617 in place, the magnet holder 1604 may be affixed to the support plate 1606, such that the two may move together as a single unit. These fasteners 1617 inserted through the mounting holes 1616 should not be mistaken for the fasteners 1632 disposed in the fastener housings 1630, which may serve a different purpose (e.g., enabling a user to adjust the height of the fixed magnet assembly 1600, such as the position of the magnet holder 1604 and support plate 1606 relative to the mounting plate 1602 on the z-axis). With the magnet holder 1604, support plate 1606, and the mounting plate 1602 mechanically coupled together, the mounting plate 1602 of the fixed magnet assembly 1600 can then be installed in (for example, affixed to) the diagnostic or preparatory apparatus using any suitable mechanism. In some embodiments, the fixed magnet assembly 1600 may be implemented in a particular diagnostic or preparatory apparatus by affixing the mounting plate 1602 to a cover 1650 of the apparatus using a fastener, such as using very high bond tape.

In some embodiments, the fixed height (e.g., the up/down position) of the magnet holder 1604 and/or the support plate 1606, relative to the mounting plate 1602 and the rest of the diagnostic or preparatory apparatus, may be adjusted by a user, such as by using the following technique or procedure. First, the fasteners 1642 in the mounting brackets 1640 can be loosened (e.g., by turning the fasteners 1642 counter-clockwise). The fasteners 1642 may serve to lock-in the height once the correct height is determined (e.g., by tightly fastening the magnet holder 1604 to the mounting brackets 1640); loosening the fasteners 1642 allows the height to be adjusted. The fasteners 1642 can remain loose during height adjustment, after which they can be tightened to ensure that the support plate 1606 remains at the correct position.

After loosening the fasteners 1642, the fasteners 1632 in the fastener housings 130 can be individually adjusted or adjusted in-sync, in order to adjust the height of the support plate 1606. For instance, in some cases, each of the fasteners 1632 may be a jack screw which is disposed through a recess of a fastener housing 1630 and threaded through a recess of the support plate 1606. Thus, the support plate 1606 may move up and down, accordingly, as the jack screw is threaded further into, or out of, the support plate 1606. For instance, turning the jack screw in a clockwise direction may thread the jack screw further into the support plate 1606 and bring that portion of the support plate 1606 towards the fastener housing 130, thereby raising that portion of the support plate 1606. Turning the jack screw in a counter-clockwise direction may thread the jack screw out of the support plate 1606 and distance that portion of the support plate 1606 away from the fastener housing 130, thereby lowering that portion of the support plate 1606.

In some embodiments, when installing the fixed magnet assembly 1600 into a particular diagnostics or preparatory apparatus and performing the height adjustment, there may be an alignment fixture (e.g., a separate device not shown in the figures) that can be loaded into the same holes that containers of a rack would occupy when the rack is placed in a receiving bay of the apparatus. The alignment fixture can be used as a guide during the height adjustment in order to determine when the support plate 1606 and/or the magnet holder 1604 are at the correct height for that particular diagnostics or preparatory apparatus. Advantageously, the above-described height adjustment can be a one-time height adjustment that is performed once and it is not repeated once the system is placed back into operational use.

Once the support plate 1606 and/or the magnet holder 1604 are adjusted to be at the desired heights, the fasteners 1642 can be tightened in order to maintain those heights. In some embodiments, there may be an additional fixture (e.g., another separate device not shown in the figures) that enables the adjusted height of the support plate 1606 and/or the magnet holder 1604 to be checked in order to confirm they are within +/−1 mm of the nominal position expected, which can inform if the heights need to be re-adjusted during this installation procedure. This particular configuration of the fixed magnet assembly 1600 may allow the fixed magnet assembly 1600 to be inexpensively and quickly implemented into a particular apparatus on-site (e.g., at the location of the diagnostic or preparatory apparatus), despite any unknown component variation that may exist among different apparatuses. FIG. 16F illustrates the same fixed magnet assembly 1600 shown in FIGS. 16A-16C (including the mounting plate 1602 and the magnet holder 1604) affixed to the cover 1650 of a diagnostic or preparatory apparatus.

More specifically, FIG. 16F shows how the fixed magnet assembly 1600 can be implemented within a receiving bay of a diagnostic or preparatory apparatus, such as the receiving bay 500 of the diagnostic or preparatory apparatus shown in FIGS. 5A-5B, so that when the receiving bay receives a rack with reagent holders inserted into the rack, the process tubes of those reagent holders rest on the mounting plate 1602 of the fixed magnet assembly 1600 next to the magnets in the magnet holder 1604. Furthermore, the one or more movable magnets of a magnetic separator (not shown in this figure, but described above with reference to FIGS. 3A-3C) can apply a magnetic force to each process tube of the reagent holders in the rack. In addition, with the fixed magnet assembly 1600 installed in this position, a constant, consistent magnetic force from the magnets of the fixed magnet assembly 1600 (e.g., the magnets in the magnet holder 1604) is also applied to each third snap-in container of the reagent holders in the rack.

Figure 17A:
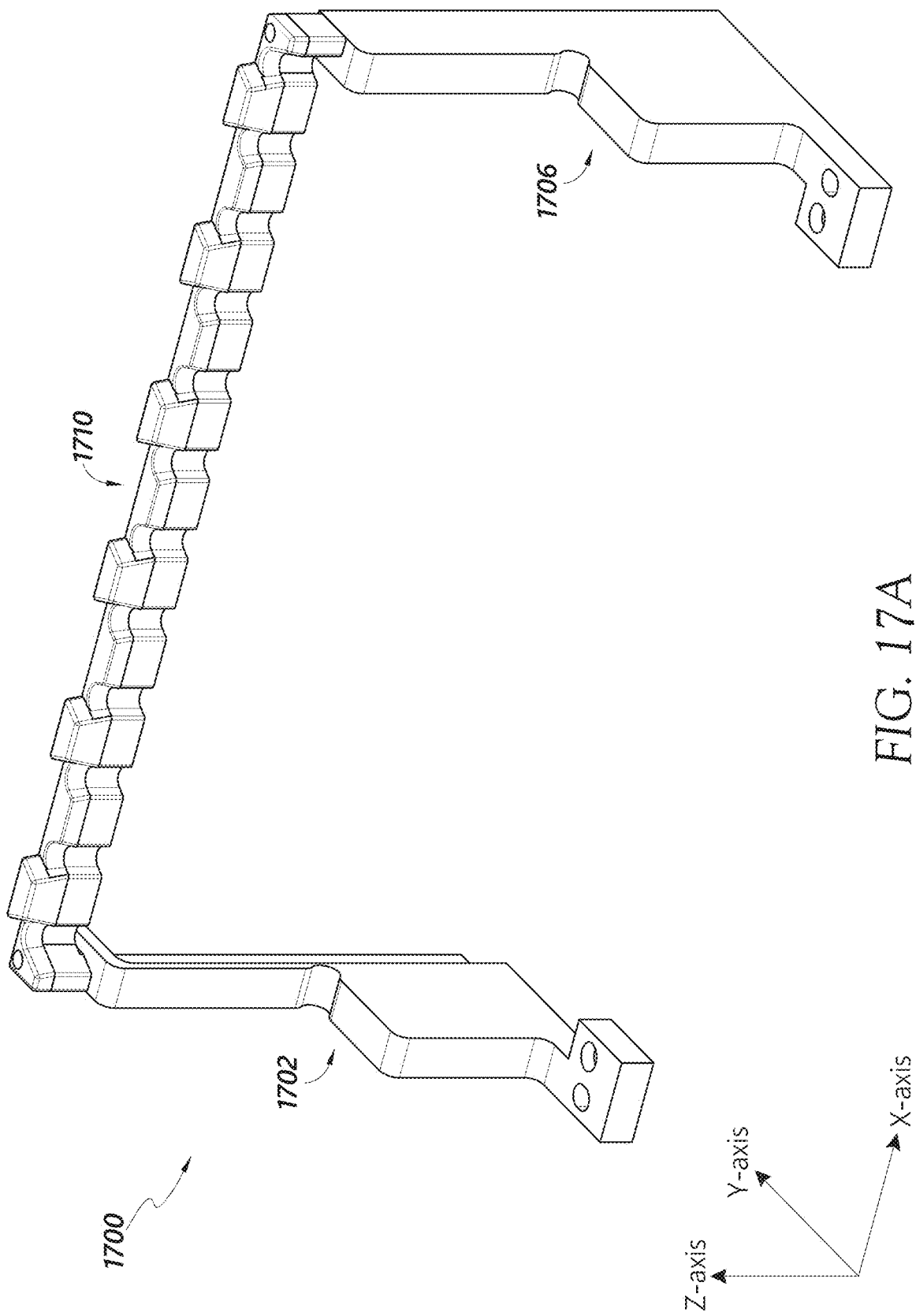
FIGS. 17A-17D illustrate isometric views of an embodiment of a bridge for installing a fixed magnet assembly within an automated diagnostic or preparatory apparatus, in accordance with embodiments disclosed herein.
Figure 17B:
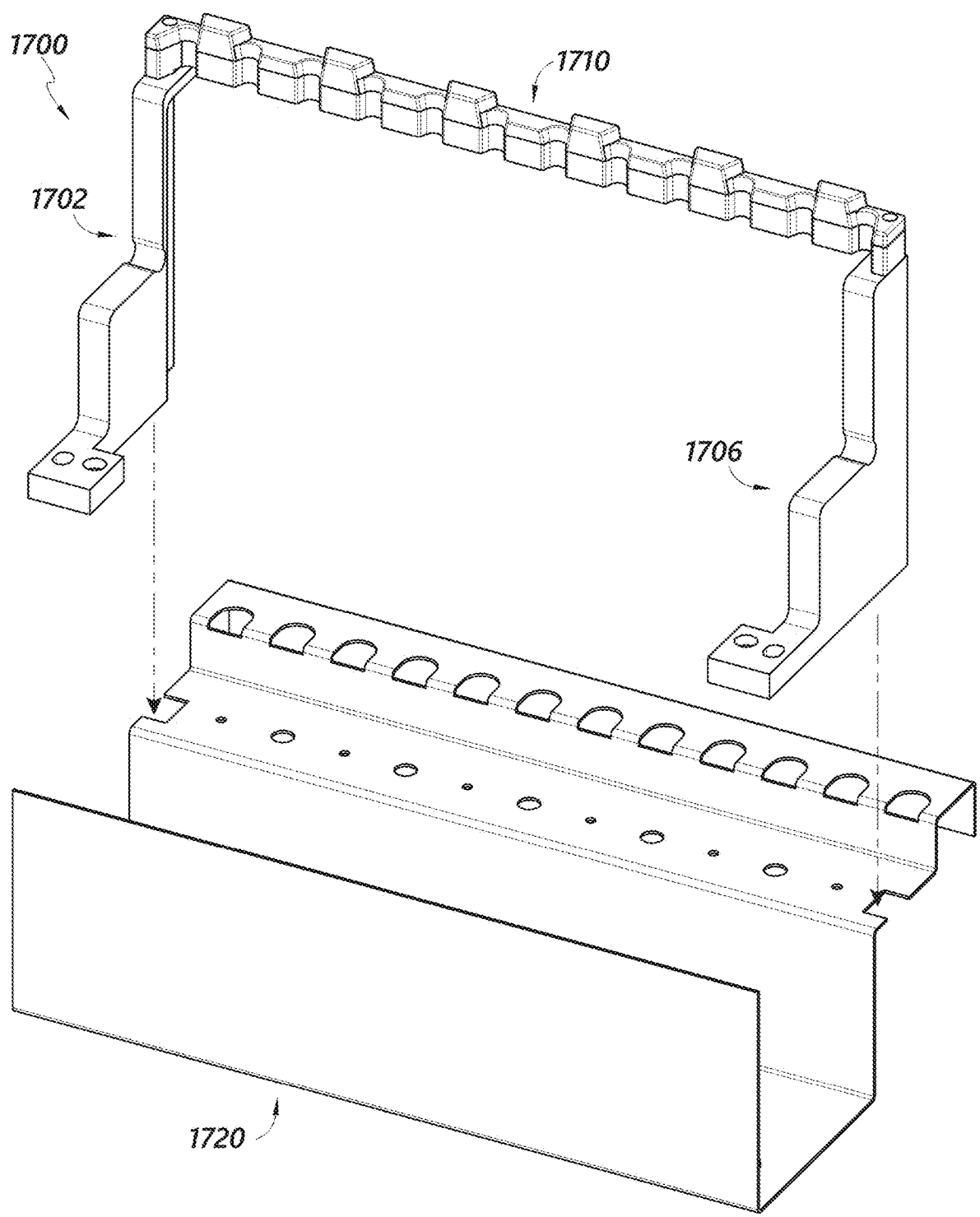
Figure 17C:
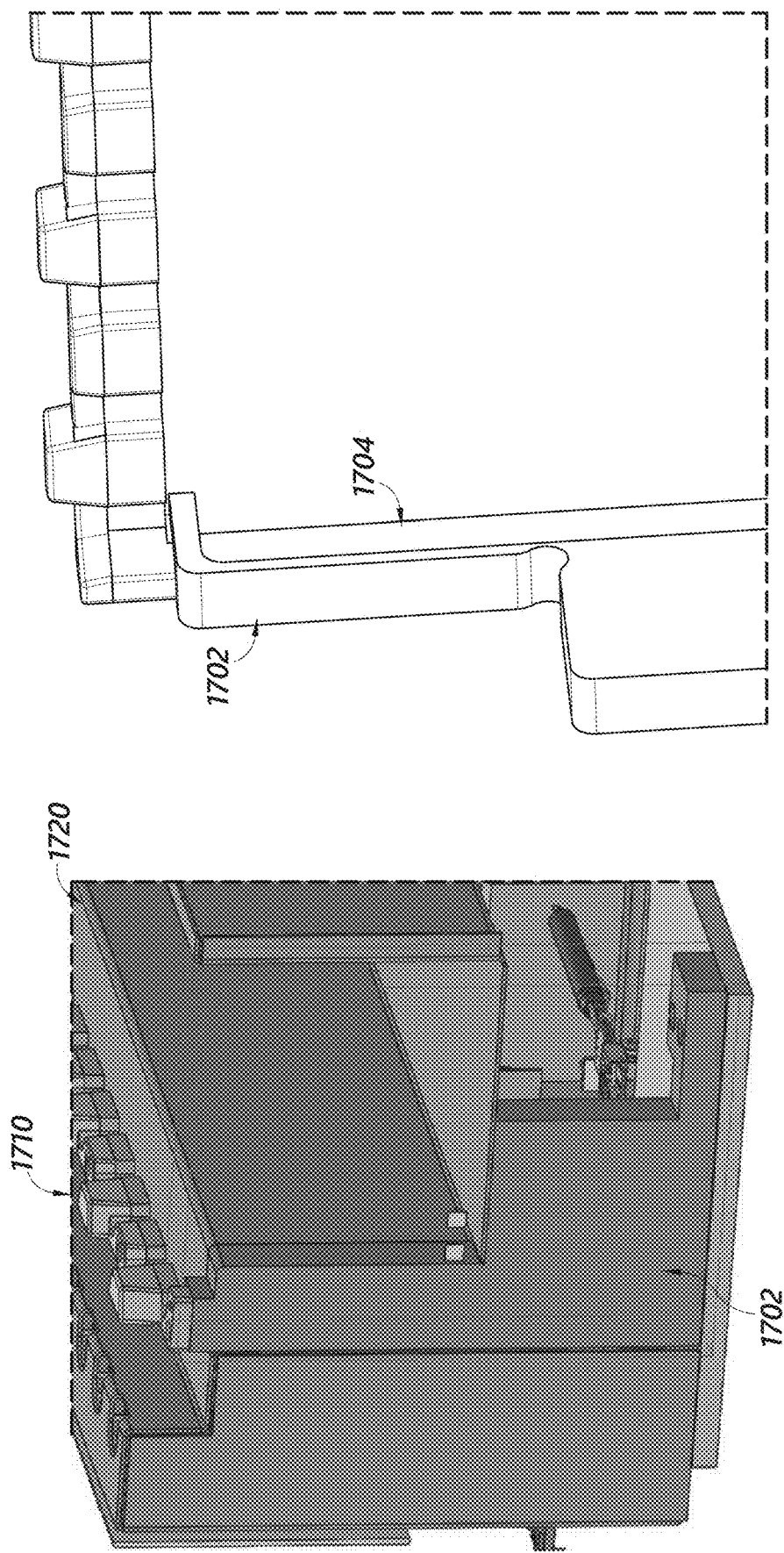
Figure 17D:
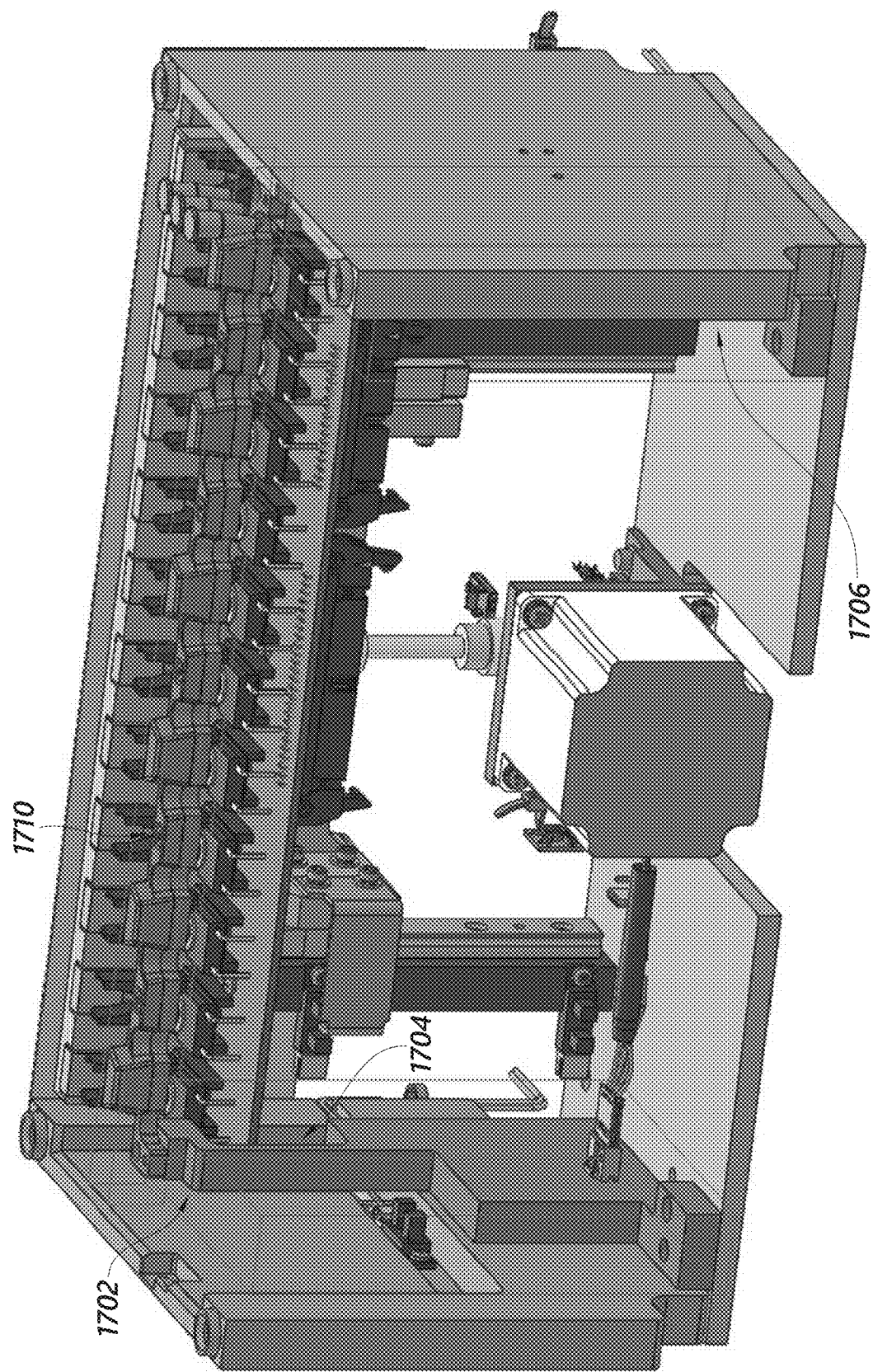

FIGS. 17A-17D illustrate isometric views of an example structure for installing and implementing a fixed magnet assembly 1710 into an automated diagnostic or preparatory apparatus. More specifically, FIG. 17A shows an embodiment of a bridge 1700 used to support the fixed magnet assembly 1710. FIGS. 17B-17D illustrate how the bridge 1700 and fixed magnet assembly 1710 of FIG. 17A can be installed and implemented within the receiving bay of an automated diagnostic or preparatory apparatus, according to this non-limiting embodiment. It will be understood that the present disclosure is not limited to installing a fixed magnet assembly in accordance with this embodiment, and other structures can be suitably implemented.

In one non-limiting example, the bridge 1700 may include multiple portions, such as a first bridge portion 1702 and a second bridge portion 1706, which can be used to support the fixed magnet assembly 1710. For instance, the first bridge portion 1702 may be configured to support a first end of the fixed magnet assembly 1710 and the second bridge portion 1706 may be configured to support an opposing second end of the fixed magnet assembly 1710, thereby forming a bridge.

In some embodiments, the bridge 1700 may have a first bridge portion 1702 and a second bridge portion 1706 that are mirror symmetrical. The first bridge portion 1702 and the second bridge portion 1706 may be configured to engage with slots on the opposing sides of a cover 1720 in the receiving bay of an automated diagnostic or preparatory apparatus, resulting in the bridge 1700 straddling the cover 1720 as shown in FIG. 17B.

This can be better seen in FIGS. 17C and 17D, which show the first bridge portion 1702 installed on one end of the cover 1720. The second bridge portion 1706 is not shown, but it would be on the opposing end of the cover 1720. The opposing ends of the fixed magnet assembly 1710 can be seated respectively on the first bridge portion 1702 and the second bridge portion 1706, which hold the fixed magnet assembly 1710 above the cover 1720 and position the fixed magnet assembly 1710 in the proper place to precisely exert magnetic force on the magnetic particles residing within the corresponding tubes of a rack that has been placed in the receiving bay.

In some embodiments, the first bridge portion 1702 and the second bridge portion 1706 may have recesses that allow the first bridge portion 1702 and the second bridge portion 1706 to fit cleanly on the ends of the cover 1720 without disturbing any components of the diagnostic or preparatory apparatus that may reside under the cover 1720. For example, FIGS. 17C and 17D show the first bridge portion 1702 having a recess 1704 shaped and sized to receive components (e.g., printed circuit boards) of the diagnostic or preparatory apparatus.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A system for analyzing nucleic acids, comprising:
 a receiving bay configured to receive a plurality of lysing tubes aligned along a lysing axis and a plurality of mixing tubes aligned along a mixing axis generally parallel to the lysing axis, the receiving bay comprising:
  one or more first magnets aligned along a first magnet axis generally parallel to the lysing and the mixing axes, the one or more first magnets configured to move between a position below the plurality of lysing tubes to a position adjacent to the plurality of lysing tubes when the plurality of lysing tubes are received in the receiving bay, the one or more first magnets configured to apply a first magnetic force to contents of the plurality of lysing tubes when the plurality of lysing tubes are received in the receiving bay and the one or more first magnets are positioned adjacent to the plurality of lysing tubes, and
  a plurality of second magnets enclosed within a plurality of housings aligned along a second magnet axis generally parallel to the first magnet axis, each housing of the plurality of housings enclosing two of the plurality of second magnets, the plurality of second magnets configured to remain stationary when the plurality of mixing tubes are received in the receiving bay, the plurality of second magnets configured to apply a second magnetic force to contents of the plurality of mixing tubes when the plurality of mixing tubes are received in the receiving bay.

2. The system of claim 1, wherein the plurality of second magnets are included in a fixed magnet assembly comprising:
 a mounting plate;
 a support plate having a height relative to the mounting plate; and
 a first plurality of fasteners mechanically coupling the support plate to the mounting plate, wherein the first plurality of fasteners enable the height of the support plate relative to the mounting plate to be user-adjustable.

3. The system of claim 1, wherein, when the plurality of lysing tubes and the plurality of mixing tubes are received in the receiving bay, the one or more first magnets are configured to apply the first magnetic force to contents of each of the plurality of lysing tubes along a direction that is generally perpendicular to the lysing axis, and the plurality of second magnets are configured to apply the second magnetic force to contents of each of the plurality of mixing tubes along a direction that is generally parallel to the mixing axis.

4. The system of claim 1, wherein, when the plurality of lysing tubes and the plurality of mixing tubes are received in the receiving bay, the one or more first magnets are configured to apply the first magnetic force to contents of each of the plurality of lysing tubes along a direction that is generally perpendicular to the lysing axis, and the plurality of second magnets are configured to apply the second magnetic force to contents of each of the plurality of mixing tubes along a direction that is generally perpendicular to the mixing axis.

5. The system of claim 1, wherein the receiving bay is further configured to receive a processing device comprising the plurality of lysing tubes and the plurality of mixing tubes, a lysing tube of the plurality of lysing tubes and a mixing tube of the plurality of mixing tubes aligned along each of a plurality of parallel processing axes, wherein the first magnet axis and the second magnet axis are generally perpendicular to the plurality of processing axes when the processing device is received in the receiving bay.

6. The system of claim 1, wherein the first magnet axis is spatially separate from the second magnet axis a distance such that the one or more first magnets do not exert the first magnetic force on contents of the plurality of mixing tubes when the plurality of mixing tubes are received in the receiving bay, and the plurality of second magnets do not exert the second magnetic force on contents of the plurality of lysing tubes when the plurality of lysing tubes are received in the receiving bay.

7. The system of claim 1, wherein, when the plurality of mixing tubes are received in the receiving bay, a first of the two magnets in each housing is configured to apply the second magnetic force to contents of a first mixing tube at a first position of the first mixing tube, and wherein a second of the two magnets in each housing is configured to apply the second magnetic force to contents of a second mixing tube that is adjacent to the first mixing tube, the second of the two magnets configured to apply the second magnetic force at a second position of the second mixing tube that is about 180° or less than 180° from a first position of the second mixing tube.

8. The system of claim 1, wherein, when the plurality of mixing tubes is received in the receiving bay, the ratio of mixing tubes to housings is two-to-one.

9. The system of claim 8, comprising a plurality of first magnets aligned along the first magnet axis, and wherein, when the plurality of lysing tubes is received in the receiving bay, the ratio of lysing tubes to first magnets is one-to-one.

10. The system of claim 1, wherein each housing comprises two faces that are each angled a different angle relative to the second magnet axis, and wherein each of the two second magnets is positioned adjacent to an interior wall of one angled face.

11. The system of claim 1, wherein the receiving bay further comprises a support plate positioned between the plurality of second magnets and a cover of the receiving bay.

12. The system of claim 11, wherein the support plate comprises a plurality of recesses each configured to receive a bottom portion of one mixing tube when the plurality of mixing tubes are received in the receiving bay.

13. The system of claim 11, wherein the plurality of housings are movable relative to the support plate when the plurality of mixing tubes are not received in the receiving bay.

14. The system of claim 1, wherein the plurality of housings are formed in a unitary structure.

15. The system of claim 1, wherein the plurality of housings are separated by a plurality of connectors.

16. The system of claim 1, further comprising the plurality of lysing tubes and the plurality of mixing tubes received in the receiving bay.

17. The system of claim 1, wherein, when the plurality of lysing tubes and the plurality of mixing tubes are received in the receiving bay:
   a lysing tube of the plurality of lysing tubes and a mixing tube of the plurality of mixing tubes are aligned along each of a plurality of parallel processing axes,
   the one or more first magnets are configured to apply the first magnetic force along the respective processing axis of each of the plurality of lysing tubes, and
   the plurality of second magnets are configured to apply the second magnetic force at a point offset from the respective processing axis of each of the plurality of mixing tubes.

* * * * *